United States Patent
Atala et al.

(10) Patent No.: US 9,248,015 B2
(45) Date of Patent: Feb. 2, 2016

(54) PRODUCTION OF TISSUE ENGINEERED HEART VALVES

(75) Inventors: Anthony Atala, Winston Salem, NC (US); James Yoo, Winston Salem, NC (US)

(73) Assignee: Wake Forest University Health Services, Winston-Salem, NC (US)

( * ) Notice: Subject to any disclaimer, the term of this patent is extended or adjusted under 35 U.S.C. 154(b) by 1041 days.

(21) Appl. No.: 11/373,066

(22) Filed: Mar. 10, 2006

(65) Prior Publication Data

US 2006/0253192 A1 Nov. 9, 2006

Related U.S. Application Data

(60) Provisional application No. 60/660,832, filed on Mar. 11, 2005, provisional application No. 60/686,316, filed on Jun. 1, 2005.

(51) Int. Cl.
| | | |
|---|---|---|
| A61F 2/24 | (2006.01) | |
| A61L 27/36 | (2006.01) | |
| A61L 27/38 | (2006.01) | |
| B82Y 5/00 | (2011.01) | |
| B82Y 10/00 | (2011.01) | |
| A61L 27/50 | (2006.01) | |

(52) U.S. Cl.
CPC ........... *A61F 2/2415* (2013.01); *A61L 27/3604* (2013.01); *A61L 27/3641* (2013.01); *A61L 27/383* (2013.01); *A61L 27/3808* (2013.01); *A61L 27/3826* (2013.01); *A61L 27/3839* (2013.01); *A61L 27/3886* (2013.01); *B82Y 5/00* (2013.01); *B82Y 10/00* (2013.01); *A61L 27/507* (2013.01)

(58) Field of Classification Search
CPC ............. A61F 2/2415; A61K 27/3886; A61K 27/3808; A61K 27/3826; B82Y 5/00; B82Y 10/00
See application file for complete search history.

(56) References Cited

U.S. PATENT DOCUMENTS

| | | | |
|---|---|---|---|
| 5,281,422 A | 1/1994 | Badylak et al. | |
| 5,645,532 A | 7/1997 | Horgan | |
| 5,698,271 A | 12/1997 | Liberti et al. | |
| 5,855,610 A | 1/1999 | Vacanti et al. | |
| 5,922,028 A | 7/1999 | Plouhar et al. | |
| 6,099,832 A * | 8/2000 | Mickle et al. | 424/93.21 |
| 6,143,293 A | 11/2000 | Weiss et al. | |
| 6,171,344 B1 | 1/2001 | Atala | |
| 6,428,802 B1 | 8/2002 | Atala | |
| 6,471,993 B1 * | 10/2002 | Shastri et al. | 424/486 |
| 6,530,956 B1 | 3/2003 | Mansmann | |
| 6,537,567 B1 | 3/2003 | Niklason et al. | |
| 6,592,623 B1 | 7/2003 | Bowlin et al. | |
| 6,596,296 B1 | 7/2003 | Nelson et al. | |
| 6,649,159 B2 | 11/2003 | Yang et al. | |
| 7,179,287 B2 * | 2/2007 | Wolfinbarger, Jr. | 623/1.41 |
| 7,531,503 B2 | 5/2009 | Atala et al. | |
| 7,622,299 B2 | 11/2009 | Sanders et al. | |
| 2002/0028243 A1 | 3/2002 | Masters | |
| 2002/0034476 A1 | 3/2002 | Lauffer et al. | |
| 2002/0081732 A1 | 6/2002 | Bowlin et al. | |
| 2002/0087174 A1 | 7/2002 | Capello | |
| 2002/0090725 A1 | 7/2002 | Simpson et al. | |
| 2003/0021821 A1 | 1/2003 | Fertala et al. | |
| 2003/0097180 A1 | 5/2003 | Tormala et al. | |
| 2003/0219417 A1 | 11/2003 | Wolfinbarger | |
| 2004/0005297 A1 | 1/2004 | Connelly et al. | |
| 2004/0009600 A1 | 1/2004 | Bowlin et al. | |
| 2004/0037813 A1 * | 2/2004 | Simpson et al. | 424/93.7 |
| 2004/0044403 A1 * | 3/2004 | Bischoff et al. | 623/1.41 |
| 2004/0093081 A1 | 5/2004 | Nilsson et al. | |
| 2004/0110439 A1 * | 6/2004 | Chaikof et al. | 442/123 |
| 2004/0117033 A1 | 6/2004 | Frondoza et al. | |
| 2004/0146546 A1 | 7/2004 | Gravett et al. | |
| 2004/0249464 A1 | 12/2004 | Bindseil et al. | |
| 2005/0095695 A1 | 5/2005 | Shindler et al. | |
| 2005/0142161 A1 | 6/2005 | Freeman et al. | |
| 2005/0266067 A1 | 12/2005 | Sengupta et al. | |
| 2006/0204441 A1 | 9/2006 | Atala et al. | |
| 2006/0204445 A1 | 9/2006 | Atala et al. | |
| 2006/0204539 A1 | 9/2006 | Atala et al. | |
| 2006/0240061 A1 | 10/2006 | Atala et al. | |
| 2006/0246584 A1 | 11/2006 | Covelli | |
| 2006/0253192 A1 | 11/2006 | Atala et al. | |

(Continued)

FOREIGN PATENT DOCUMENTS

| | | |
|---|---|---|
| DE | 2917037 B1 | 4/1980 |
| DE | 19919625 A1 | 11/2000 |

(Continued)

OTHER PUBLICATIONS

Ott, M. et al. "Sheer stress-conditioned, endothelial cell-seeded vascular grafts: Improved cell adherence in response to in vitro shear stress," *Surgery*, Mar. 1995, pp. 334-339.

Ballou et al., "Noninvasive Imaging of Quantum Dots in Mice", *Bioconjugate Chem.*, vol. 15, pp. 79-86, 2004.

Chen et al., "The Use of a PLGA Fiber/Collagen Composite Web as a Scaffold for Engineering of Articular Cartilage Tissue With Adjustable Thickness", *J. Biomed Mater Res A*, Dec. 15, 2003;67(4): 1170-80.

Hafemann et al., "Use of a Collagen/Elastin-Membrane for the Tissue Engineering of Dermis", *Burns*, vol. 25, pp. 373-384, 1999.

Hirsch et al., "Nanoshell-Mediated Near-Infrared Thermal Therapy of Tumors Under Magnetic Resonance Guidance", *PNAS*, vol. 100, pp. 13549-13554, 2003.

(Continued)

*Primary Examiner* — Marcia S Noble

(74) *Attorney, Agent, or Firm* — Thomas J. Engellenner; Reza Mollaaghababa; Pepper Hamilton LLP

(57) ABSTRACT

The invention is directed to methods for preparing artificial heart valves by preconditioning a matrix seeded with endothelial cells and smooth muscle cells differentiated from isolated progenitor cells. These cell seeded matrices are exposed to fluid conditions that mimic blood flow through the heart to produce tissue engineered heart valves that are analogous to native heart valves.

2 Claims, 24 Drawing Sheets

(56) References Cited

U.S. PATENT DOCUMENTS

| | | | |
|---|---|---|---|
| 2006/0257377 | A1 | 11/2006 | Atala et al. |
| 2007/0213801 | A1* | 9/2007 | Kutryk et al. ............. 623/1.11 |
| 2008/0003184 | A1 | 1/2008 | Uvdal et al. |
| 2008/0025956 | A1* | 1/2008 | Yoder et al. ............. 424/93.7 |
| 2010/0129450 | A1 | 5/2010 | Atala et al. |

FOREIGN PATENT DOCUMENTS

| | | | |
|---|---|---|---|
| DE | 20019928 U1 | | 2/2001 |
| EP | 1 405 649 A1 | | 4/2004 |
| EP | 1604697 A1 | | 12/2005 |
| JP | 2004-162244 A | | 6/2004 |
| WO | 9911191 A1 | | 3/1999 |
| WO | WO 99/48541 | | 9/1999 |
| WO | 0127365 A1 | | 4/2001 |
| WO | WO 0137884 | | 5/2001 |
| WO | 0180921 A2 | | 11/2001 |
| WO | WO 02/00149 | | 1/2002 |
| WO | 0230482 A1 | | 4/2002 |
| WO | WO 03/007790 A2 | | 1/2003 |
| WO | 200400915 A2 | | 12/2003 |
| WO | WO 2004/014304 | | 2/2004 |
| WO | WO 2004/044281 | | 5/2004 |
| WO | 2004-045425 A1 | | 6/2004 |
| WO | 2004098420 A2 | | 11/2004 |
| WO | WO 2005/020849 A2 | | 3/2005 |

OTHER PUBLICATIONS

Liao et al., "Hierarchically Biomimetic Bone Scaffold Materials: Nano-HA/Collagen/PLA Composite", *J. Biomed Mater Res B Appl Biomater* May 15, 2004;69(2): 158-65.

Klebe, Robert J., "Cytoscribing: A Method for Micropositioning Cells and the Construction of Two-and Three-Dimensional Synthetic Tissues," *Experimental Cell Research* 179 (1988), pp. 362-373.

International Search Report and Written Opinion, PCT/US2006/008962 issued Feb. 20, 2007.

Magarey, Aust. J. Exp. Biol. Med. Sci., vol. 35, pp. 347-352, 1957.

Japanese Office Action Appl. JP2008-501058 dated Feb. 14, 2012. (8 pages).

Huang, J Biomat Sci. Dec. 2001, pp. 979-993.

International Search Report and Written Opinion, PCT/US2006/008964, dated Feb. 5, 2007.

Gnasso, Atherosclerosis, 2001, 156:171-176.

Australian Search Report Appl. No. 2006223063 dated Oct. 19, 2010.

European Office Action Appl. 06738128.5 dated May 6, 2008.

European Office Action Appl. 06738128.5 dated Oct. 15, 2010.

Australian Office Action Appl. No. 2006223112 dated Sep. 30, 2010.

European Office Action Appl. 06738070.9 dated Sep. 4, 2008.

Japanese Office Action Appl. JP2008-501039 dated Apr. 5, 2011.

* cited by examiner

FIGURE 5A
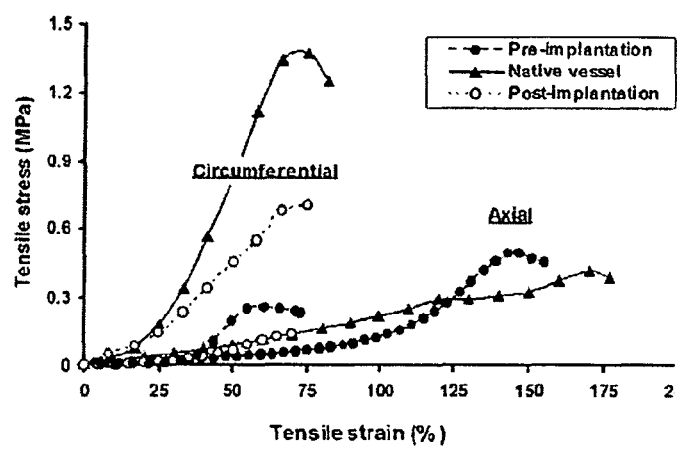
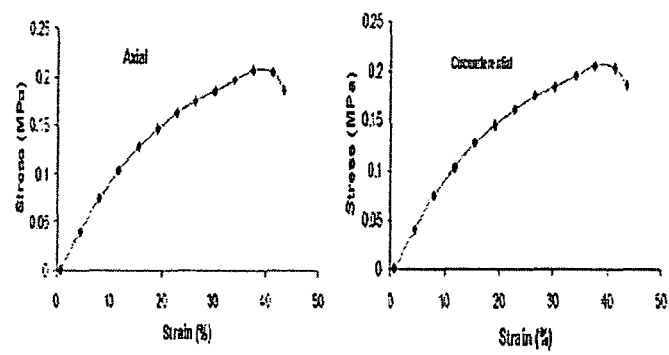
FIGURE 5B

FIGURE 6A
FIGURE 6B
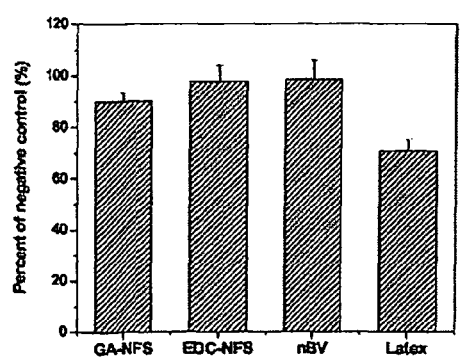
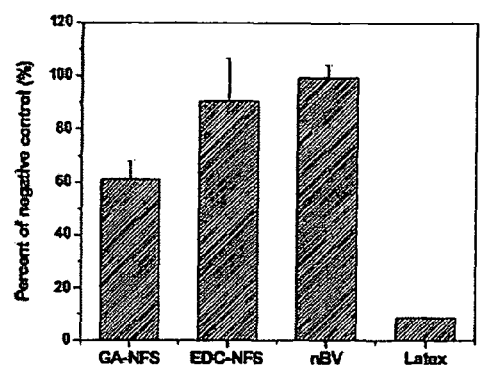

FIGURE 8A
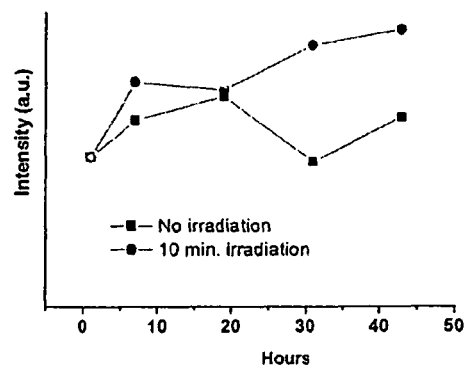
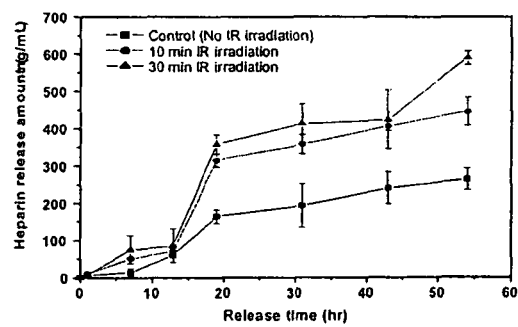
FIGURE 8B

FIGURE 11A
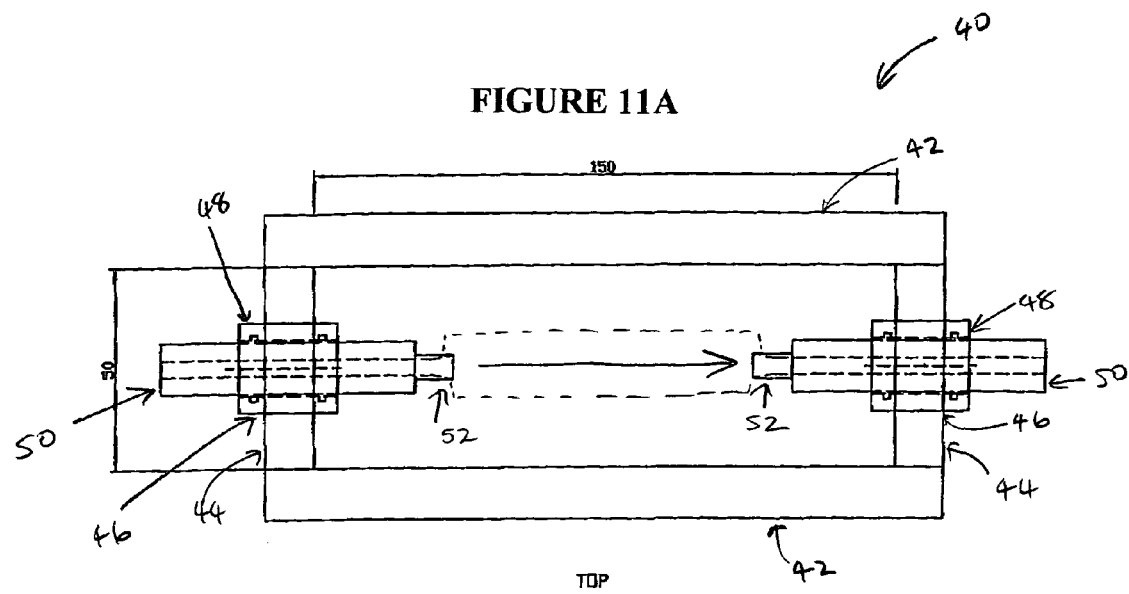
TOP
FIGURE 11B
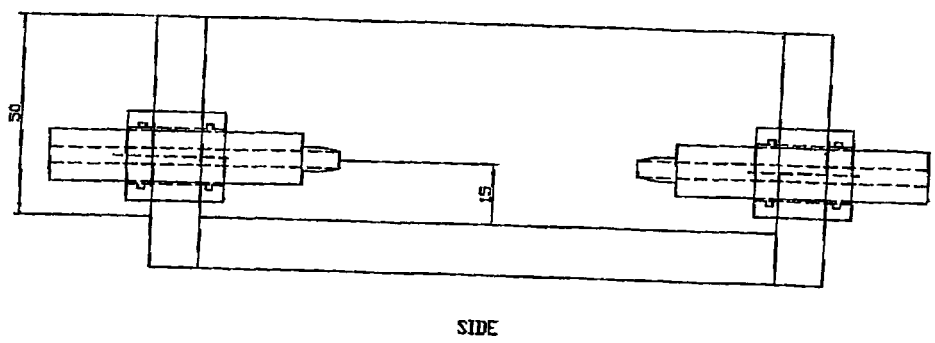
SIDE
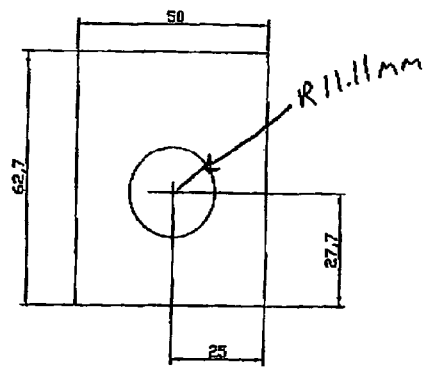
FIGURE 11C A. Normal mitral valve; B. Porcine replacement valve; C. Artificial replacement valve.

Endothelial Cell Seeding
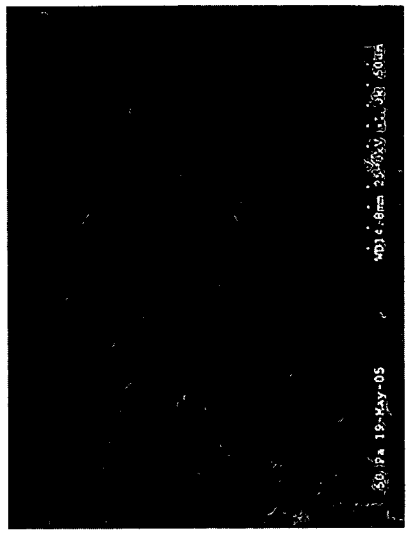
FIGURE 16B
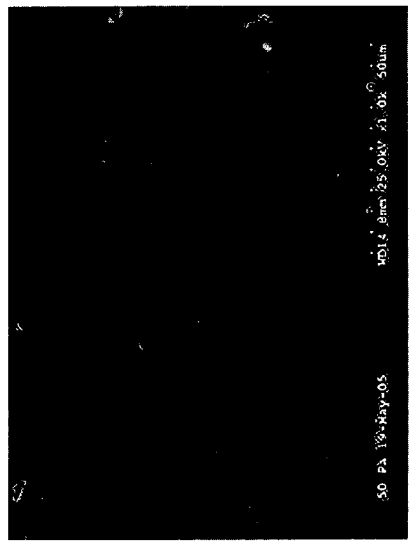
FIGURE 16A
FIGURE 16

Platelet deposition Assay
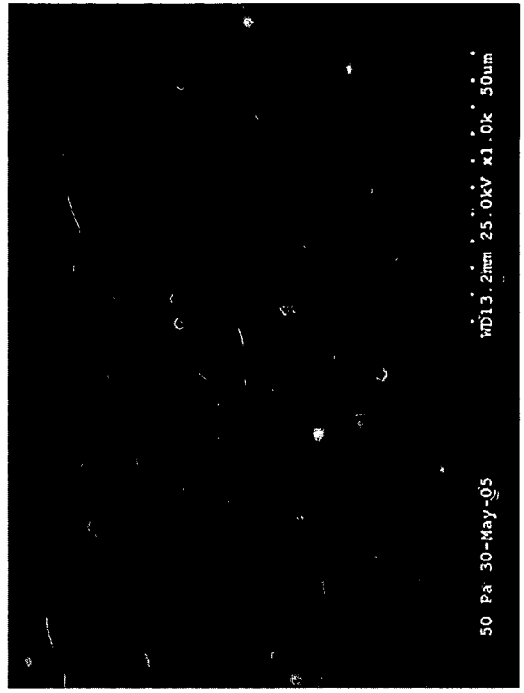
FIGURE 17B
EC + DCM
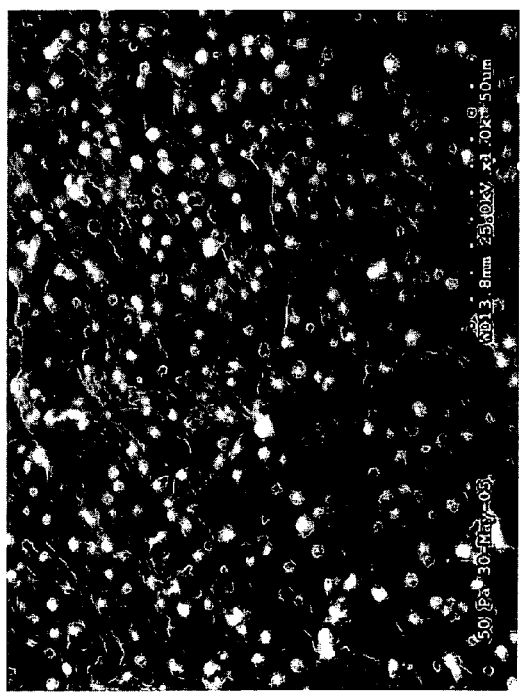
FIGURE 17A
DCM
FIGURE 17

Human Endothelial and Smooth Muscle like Cell from progenitor cells

Differentiated Endothelial Cells

Differentiated Smooth Muscle Like Cells

2wks in vitro culture   Treated w/ 5 azatic acid

Human Endothelial and Smooth Muscle Cells from Progenitor Cells

Differentiated Endothelial Cells

PECAM-1    Ulex-FITC    KDR    VE-CADHERIN    vWf

Differentiated Smooth Muscle Cells

SM α-actin    MHC    Myocardin

Human Endothelial and Smooth Muscle like Cell from Progenitor Cells

Western blot analysis for differentiated endothelial cells(A) and smooth muscle like cells(B)

Porcine decellularized matrix before (A) and after decellularization (B). Lyophillization (C).

Porcine Valve Decellularized Matrix (DCM)

A: H&E staining of DCM, L: leaflet and VW: valvular wall.
B: DNA assay for Decellularized Matrix.

PRODUCTION OF TISSUE ENGINEERED HEART VALVES

RELATED APPLICATIONS

The present application claims priority to U.S. Provisional Application No. 60/660,832 filed Mar. 11, 2005 and U.S. Provisional Application Ser. No. 60/686,316 filed Jun. 1, 2005, the contents of which are hereby incorporated by reference in their entirety.

BACKGROUND OF THE INVENTION

The technical field of this invention relates to tissue engineered heart valves. Heart valve replacements are limited because donor tissues is in short supply. There are several types of valves that have been used for heart transplantations such as mechanical heart valves and bioprosthetic valves. The bioprosthetic valves are typically those obtained from other species and are known as xenografts. Porcine valves are the most common xenograft.

Unlike mechanical heart valves, bioprosthetics have a natural trileaflet structure and should have similar flow characteristics as human valves. However, in order to prevent immune responses to the cellular components of the valve, xenograft tissues are treated with chemical cross-linking agents such as glutaraldehyde. While this approach is successful in limiting acute rejection of these grafts, there are serious limitations. For example, leaflet flexibility is compromised, with the bending stiffness of the leaflets being significantly increased. Also, glutaraldehyde fixation increases the incidence and extent of leaflet and aortic conduit calcification. These factors combine to make bioprosthetic valves less durable and more prone to failure than natural valves.

Another major problem with replacement heart valves generally is the formation of blood clots and the risk of thrombosis. Thrombosis alters the mechanical fluid flow property of the valves and reduces their functionality as well as increasing the risk of heart failure in the patient.

Accordingly, a need exists for improved replacement heart valves that have a similar functionality as native heart valves but without the adverse effects of existing heart valves.

SUMMARY OF THE INVENTION

The present invention provides methods and compositions for preparing tissue engineered heart valves. The tissue engineered valve has a viable cellular component, phenotypically compatible with the patient's own cardiac tissue. The replacement valve is produced from endothelial cells and muscle cells, such as smooth muscle cells. Endothelial cell coverage of the valve surface prevents the occurrence of thrombosis formation. In the present invention, circulating progenitor cells can be isolated from the peripheral blood of patients with vascular disease. These isolated progenitor cells can be grown and differentiated into endothelial and muscle cells that can be used to seed matrices. These cell seeded matrices can be exposed to fluid conditions that mimic blood flow through the heart, resulting in tissue engineered heart valves that are preconditioned to be analogous to native heart valves. Thus, the engineered valves can be designed to retain more of their natural flexibility and thus function more efficiently like their in vivo counterpart.

These heart valves can be made from electrospun matrices or decellularized matrices, seeded with endothelial cells and muscle cells derived from circulating progenitor cells. These seeded matrices can be preconditioned under physiological fluid conditions that mimic the blood composition, flow rate and pulse rate, as well as the opening and closing function of a native heart valve. The method involves using a preconditioning chamber, into which the seeded matrices can be placed. The seeded matrices can then be subjected to varying fluid flow parameters in which biological fluid flows through the seeded matrices in a closed loop system. The biological fluid is designed to have the consistency of blood and plasma. Continued growth and differentiation of the tissue layer on the matrix under fluid flow conditions can result in the formation of tissue engineered heart valves that function as native in vivo heart valves. The matrices may also be coupled with nanoparticles and therapeutic agents for controlled delivery of therapeutic agents, and/or coupled with image enhancing agents to monitor the tissue and scaffold remodeling in vivo.

Accordingly, in one aspect, the invention pertains to a method for producing a preconditioned heart valve by providing a biocompatible matrix seeded with a population of endothelial cells that have been differentiated from progenitor cells. The seeded matrix can be cultured until the endothelial cells attach to the matrix and form an endothelial cell layer. A population of smooth muscle cells that have been differentiated from progenitor cells can then be deposited onto the endothelial cell layer and cultured until a smooth muscle cell layer is formed and attaches to the endothelial cell layer. The seeded matrix can then be attached to an attachment element in a preconditioning chamber. The attachment element comprises a channel that is fluidly coupled to fluid flow system. The seeded matrix can be preconditioned in the preconditioning chamber by being exposed to a flow system in which a biological fluid is moved through the seeded matrix under physiological conditions. A preconditioned heart valve can be produced by controlling the flow-rate and pulse-rate of the biological fluid through the heart valve.

In another aspect, the invention pertains to a preconditioned tissue engineered heart valve, comprising a biocompatible matrix having a heart valve shape seeded with a population of endothelial cells differentiated from progenitor cells. These endothelial cells attach to the matrix and are cultured to form an endothelial cell layer. The heart valve also comprises a population of smooth muscle cells differentiated from progenitor cells that are seeded onto the endothelial cell layer and cultures such that the smooth muscle cells form a smooth muscle cell layer that attaches to the endothelial cell layer. The seeded cells can be preconditioned in a preconditioning chamber that exposes the seeded cells to a biological fluid that can be passed through the seeded matrix at a flow-rate and pulse-rate equivalent to normal blood flow through the heart.

The biocompatible matrix can be a decellularized matrix, an electrospun matrix and a synthetic polymer matrix. In a preferred embodiment, the biocompatible matrix is a decellularized heart valve. The endothelial cells can be isolated for example from a human saphenous vein, or derived from progenitor cells isolated from peripheral blood or bone marrow. The preconditioning chamber is a container with dimensions suitable for attaching a length of matrix. For example, the shape of a rectangular box with holes at each end to which attachment elements can be added. The attachment elements hold the ends of the seeded matrix in an open configuration such that biological fluid can pass from one end of the preconditioning chamber through the seeded matrix and out from the other end of the chamber in a closed loop fluid flow system.

The step of preconditioning the matrix can involve moving the biological fluid through the inside surface of the attached matrix in a closed fluid flow system. This allows the inside of the seeded matrix to become preconditioned to the fluid flow and allows the seeded cells to develop under fluid flow conditions as they would in the native blood vessel. The step of preconditioning involves moving the biological fluid through the inside surface of the attached matrix as a continuous flow, for example at a flow-rate that can be incremented over time to induce a wall shear in the range of about 1 dyne/cm$^2$ to about 30 dynes/cm$^2$. The step of preconditioning the matrix can also involve moving the biological fluid through the inside surface of the attached matrix as a pulsed flow, for example, a pulsed flow that has a pulse-rate which is incremented over time to induce a wall shear in the range of about 10 dynes/cm$^2$ to about 45 dynes/cm$^2$. The pulse-rate can be incremented over time to induce a wall pressure distribution in the engineered blood vessel in the range of about 60 to about 200 mmHg.

The biological fluid can be moved through the seeded matrix by a pump such as a mechanical pump. Examples fluids include, but are not limited to, culture medium, buffer medium, and physiological medium. The composition and viscosity of the biological fluid can be altered to be the equivalent to blood. This can be accomplished by adding high molecular weight proteins such as 40% of 100 kDa dextran to the culture medium, buffer medium, and physiological medium.

The step of preconditioning may also involve preconditioning the exterior of the matrix by seeding the exterior matrix with another population of cells that can be the same or different from the endothelial cell population, and exposing the exterior seeded matrix to a biological fluid. This can be done by adding a volume of biological fluid to the preconditioning chamber such that the outside surface of the matrix is exposed to the biological fluid. In one embodiment, the biological fluid used to precondition the inside of the seeded leaflets of the valve is the same as the biological fluid used to precondition the outside of the valve. In another embodiment, the biological fluid used to precondition the inside of the vessel is different from the biological fluid used to precondition the outside of the vessel. For example, the inside of the matrix (lumen side) can be seeded with endothelial cells and preconditioned with a biological fluid that is optimal for endothelial cell growth and proliferation, while the outside of the matrix can be seeded with smooth muscle cells and preconditioned with a biological fluid that is optimal for smooth muscle cell growth and proliferation. It will be appreciated that the fluid flow parameters can be separately controlled to provide the optimum preconditioning for the inside and the outside of the seeded matrix.

In other embodiments, the matrix can be an electrospun matrix comprising at least one natural component and at least one synthetic polymer component and a therapeutic agent coupled to a nanoparticle. The natural component can be collagen and the synthetic polymer component can poly(lactide-co-glycolides) (PLGA). The electrospun matrix may further comprise elastin. The therapeutic agent can be heparin and the nanoparticle can be a quantum dot. The heparin and quantum dot can be encapsulated in a polymer and the heparin release from the nanoparticle can be locally controlled by the application of radiation at a wavelength in the range of about 700 nm to about 1000 nm. The heparin can be locally released from the nanoparticle by heating the nanoparticle so that it alters the ultrastructure of the polymer to release the heparin. In other embodiments, the nanospun matrix can further comprise an image enhancing agent such as gadolinium.

DESCRIPTION OF THE DRAWINGS

FIG. 5A is a graph of axial and circumferential stress-strain data from uniaxial testing of two decellularized constructs;

FIG. 5B is a graph of axial and circumferential stress-strain data from uniaxial testing of an electrospun vessel;

FIG. 6A is a graph of cell viability of endothelial cells cultured on four matrices;

FIG. 6B is a graph of mitochondrial metabolic activity of endothelial cells cultured on four matrices;

FIG. 8 is a graph of microcapsules containing heparin which show heparin release upon near infra-red irradiation;

FIG. 11A is a schematic top view of a preconditioning chamber of the invention;

FIG. 11B is a schematic side view of a preconditioning chamber of the invention;

FIG. 11C is a schematic traverse view of a preconditioning chamber of the invention;

FIGS. 16A and B are images matrices seeded with endothelial cells;

FIGS. 17A and B are images of cells in a platelet deposition assay;

DETAILED DESCRIPTION

Figure 1:
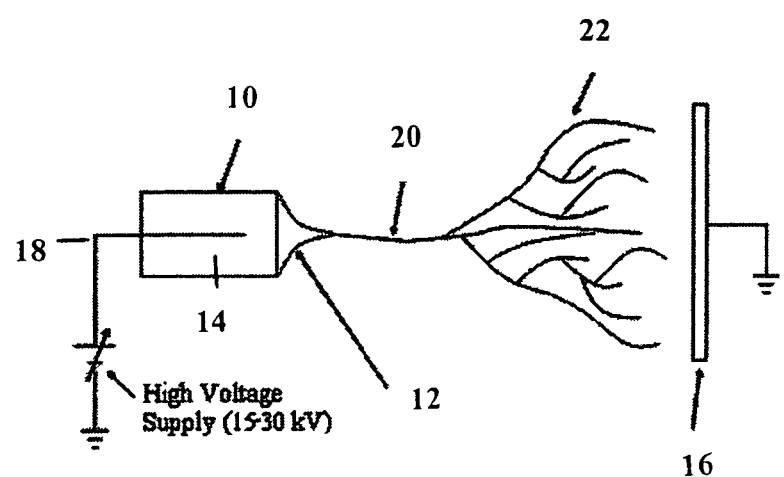
FIG. 1 is a schematic of an electrospin apparatus.

So that the invention may more readily be understood, certain terms are first defined:

The term "attach" or "attaches" as used herein refers to cells that adhere directly or indirectly to a substrate as well as to cells that adhere to other cells.

The phrase "biocompatible substrate" as used herein refers to a material that is suitable for implantation into a subject onto which a cell population can be deposited. A biocompatible substrate does not cause toxic or injurious effects once implanted in the subject. In one embodiment, the biocompatible substrate is a polymer with a surface that can be shaped into the desired structure that requires repairing or replacing. The polymer can also be shaped into a part of an structure that requires repairing or replacing. The biocompatible substrate provides the supportive framework that allows cells to attach to it, and grow on it. Cultured populations of cells can then be grown on the biocompatible substrate, which provides the appropriate interstitial distances required for cell-cell interaction.

The term "subject" as used herein is intended to include living organisms in which an immune response is elicited. Preferred subjects are mammals. Examples of subjects include but are not limited to, humans, monkeys, dogs, cats, mice, rates, cows, horses, pigs, goats and sheep.

The term "decellularized" or "decellularization" as used herein refers to a biostructure (e.g., an organ, or part of an organ), from which the cellular and tissue content has been removed leaving behind an intact acellular infra-structure. Organs such as the kidney are composed of various specialized tissues. The specialized tissue structures of an organ, or parenchyma, provide the specific function associated with the organ. The supporting fibrous network of the organ is the stroma. Most organs have a stromal framework composed of unspecialized connecting tissue which supports the specialized tissue. The process of decellularization removes the specialized tissue, leaving behind the complex three-dimensional network of connective tissue. The connective tissue infra-structure is primarily composed of collagen. The decellularized structure provides a biocompatible substrate onto which different cell populations can be infused. Decellularized biostructures can be rigid, or semi-rigid, having an ability to alter their shapes. Examples of decellularized organs useful in the present invention include, but are not limited to, the heart, kidney, liver, pancreas, spleen, bladder, ureter and urethra.

The phrase "three-dimensional scaffold" as used herein refers to the residual infra-structure formed when a natural biostructure, e.g. an organ, is decellularized. This complex, three-dimensional, scaffold provides the supportive framework that allows cells to attach to it, and grow on it. Cultured populations of cells can then be grown on the three-dimensional scaffold, which provides the exact interstitial distances required for cell-cell interaction. This provides a reconstructed organ that resembles the native in vivo organ. This three-dimensional scaffold can be perfused with a population of cultured cells, e.g., endothelial cells, which grow and develop to provide an endothelial tissue layer capable of supporting growth and development of at least one additional cultured cell population.

The term "natural biostructure" as used herein refers to a biological arrangement found within a subject, for example, organs, that include but are not limited, heart, kidney, liver, pancreas, spleen, bladder, ureter and urethra. The term "natural biostructure" is also intended to include parts of biostructures, for example parts of organs, for example, the renal artery of a kidney.

The terms "electrospinning" or "electrospun," as used herein refers to any method where materials are streamed, sprayed, sputtered, dripped, or otherwise transported in the presence of an electric field. The electrospun material can be deposited from the direction of a charged container towards a grounded target, or from a grounded container in the direction of a charged target. In particular, the term "electrospinning" means a process in which fibers are formed from a charged solution comprising at least one natural biological material, at least one synthetic polymer material, or a combination thereof by streaming the electrically charged solution through an opening or orifice towards a grounded target.

A natural biological material can be a naturally occurring organic material including any material naturally found in the body of a mammal, plant, or other organism. A synthetic polymer material can be any material prepared through a method of artificial synthesis, processing, or manufacture. Preferably the synthetic materials is a biologically compatible material. The natural or synthetic materials are also those that are capable of being charged under an electric field.

The terms "solution" and "fluid" is used in the context of producing an electrospun matrix and describes a liquid that is capable of being charged and which comprises at least one natural material, at least one synthetic material, or a combination thereof. In a preferred embodiment, the fluid comprises at least one type of collagen, an additional natural material such as at least one type of elastin and at least one synthetic polymer, e.g., poly-L glycolic acid (PLGA).

The term "co-polymer" as used herein is intended to encompass co-polymers, ter-polymers, and higher order multiple polymer compositions formed by block, graph or random combination of polymeric components.

The terms "nanoparticles," "nanostructures," and "quantum dots" are used interchangeably herein to describe materials having dimensions of the order of one or a few nanometers to a few micrometers, more preferably from about 1 to about 1000 nanometers.

The term "preconditioning chamber" as used herein refers to a container that allows a matrix seeded with cells to be conditioned such that the cells on the matrix develop under physiological conditions. For example, to create blood vessels, a matrix can be seeded with endothelial cells and the endothelial cells allowed to develop under native fluid conditions such as pulsed conditions that mimic the pulse rate of blood through native vessels, or fluid flow conditions with alterations in pressure. To begin with, the pulse rate and the flow rate can be slow until the cells adjust to this pulse-rate or flow-rate, the flow-rate and pulse-rate can then gradually be increased until the cells adjust to the new pulse-rate and flow-rate an so forth. By gradually increasing the pulse-rate and the flow-rate, the vessels become conditioned to being able to withstand pressure as high as those produced during each heartbeat.

Likewise, to create a heart valve that mimic the native heart valve, a cell seeded matrix (e.g., decellularized heart valve) can be preconditioned in a preconditioning chamber that mimics the blood flow through the aortic valve. The preconditioning chamber is designed to mimic the systolic and diastolic pressure of the native heart, allowing the seeded cells to develop under the same pulsate stress and strain conditions of a native heart valve.

The biological fluid can be moved through the inside surface of the attached matrix as a continuous flow, for example at a flow-rate that can be incremented over time to induce a wall shear in the range of about 1 dyne/cm$^2$ to about 30 dynes/cm$^2$. The step of preconditioning the matrix can also involve moving the biological fluid through the inside surface of the attached matrix as a pulsed flow, for example, a pulsed flow that has a pulse-rate which is incremented over time to induce a wall shear in the range of about 10 dynes/cm$^2$ to about 45 dynes/cm$^2$. The pulse-rate can be incremented over time to induce a wall pressure distribution in the engineered blood vessel or heart valve in the range of about 60 to about 200 mmHg. A different of the same biological fluid can also be used to precondition the outside of the matrix.

The term "biological fluid" as used herein refers a liquid that can be used to precondition an engineered blood vessel. The biological fluid has a composition and viscosity that mimics blood so that the engineered blood vessels are exposed to the same fluid flow dynamics as native blood vessels. Examples of biological fluids can include any buffer, medium of physiological fluid (e.g., DMEM with 10% FCS with a blood viscosity). The viscosity of the fluids can be altered by adding high molecular weight proteins such as 100 kDa dextran. Other molecular weight dextrans can also be used. It will be appreciated that the amount of dextran to be used depends on the molecular weight and can range from about 10%, 20%, 30%, 40%, 50%, and 60%. The composition may also be varied by adding other blood like constituents such as salts.

I Electrospun Matrices

The invention pertains to methods and compositions for producing and using electrospun matrices. The process of electrospinning generally involves the creation of an electrical field at the surface of a liquid. The resulting electrical forces create a jet of liquid which carries electrical charge. The liquid jets may be attracted to other electrically charged objects at a suitable electrical potential. As the jet of liquid elongates and travels, it will harden and dry. The hardening and drying of the elongated jet of liquid may be caused by cooling of the liquid, i.e., where the liquid is normally a solid at room temperature; evaporation of a solvent, e.g., by dehydration, (physically induced hardening); or by a curing mechanism (chemically induced hardening). The produced fibers are collected on a suitably located, oppositely charged target substrate.

The electrospinning apparatus includes an electrodepositing mechanism and a target substrate. The electrodepositing mechanism includes at least one container to hold the solution that is to be electrospun. The container has at least one orifice or nozzle to allow the streaming of the solution from the container. If there are multiple containers, a plurality of nozzles may be used. One or more pumps (e.g., a syringe pump) used in connection with the container can be used to control the flow of solution streaming from the container through the nozzle. The pump can be programmed to increase or decrease the flow at different points during electrospinning.

The electrospinning occurs due to the presence of a charge in either the orifices or the target, while the other is grounded. In some embodiments, the nozzle or orifice is charged and the target is grounded. Those of skill in the electrospinning arts will recognize that the nozzle and solution can be grounded and the target can be electrically charged.

The target can also be specifically charged or grounded along a preselected pattern so that the solution streamed from the orifice is directed into specific directions. The electric field can be controlled by a microprocessor to create an electrospun matrix having a desired geometry. The target and the nozzle or nozzles can be engineered to be movable with respect to each other thereby allowing additional control over the geometry of the electrospun matrix to be formed. The entire process can be controlled by a microprocessor that is programmed with specific parameters that will obtain a specific preselected electrospun matrix.

In embodiments in which two materials combine to form a third material, the solutions containing these components can be mixed together immediately before they are streamed from an orifice in the electrospinning procedure. In this way, the third material forms literally as the microfibers in the electrospinning process.

While the following is a description of a preferred method, other protocols can be followed to achieve the same result. In FIG. 1, a container 10, (e.g., a syringe or micropipette), with an orifice or nozzle 12 (e.g. a Taylor cone), is filled with a solution with at least one natural material, and at least one synthetic material 14. The container 10 is suspended opposite a grounded target 16, such as a metal ground screen. A fine wire 18 is placed in the solution to charge the solution in the container to a high voltage. At a specific voltage determined for each solution, the solution in the container nozzle is directed towards the grounded target. The single jet stream 20 of materials forms a splayed jet 22, upon reaching the grounded target, e.g., a rapidly rotating mandrel. The splayed jet collects and dries to form a three-dimensional, ultra thin, interconnected matrix of electrospun fibers. In some embodiments, a plurality of containers can be used with each of the containers holding a different compound.

Minimal electrical current is involved in the electrospinning process, therefore the process does not denature the materials that form the electrospun matrix, because the current causes little or no temperature increase in the solutions during the procedure.

The electrospinning process can be manipulated to meet the specific requirements for any given application of the electrospun matrix. In one embodiment, a syringe can be mounted on a frame that moves in the x, y and z planes with respect to the grounded substrate. In another embodiment, a syringe can be mounted around a grounded substrate, for instance a tubular mandrel. In this way, the materials that form the matrix streamed from the a syringe can be specifically aimed or patterned. Although the micropipette can be moved manually, the frame onto which the a syringe is mounted can also be controlled by a microprocessor and a motor that allows the pattern of streaming to be predetermined. Such microprocessors and motors are known to one of ordinary skill in the art, for example matrix fibers can be oriented in a specific direction, they can be layered, or they can be programmed to be completely random and not oriented.

The degree of branching can be varied by many factors including, but not limited to, voltage (for example ranging from about 0 to 30,000 volts), distance from a syringe tip to the substrate (for example from 1-100 cm, 0-40 cm, and 1-10 cm), the speed of rotation, the shape of the mandrel, the relative position of the a syringe tip and target (i.e. in front of, above, below, aside etc.), and the diameter of a syringe tip (approximately 0-2 mm), and the concentration and ratios of compounds that form the electrospun matrix. Other parameters which are important include those affecting evaporation of solvents such as temperature, pressure, humidity. The molecular weight of the polymer improves its ability to entangle and form fibers, and polymers with the molecular weight of 100 kDa generally performed. Those skilled in the art will recognize that these and other parameters can be varied to form electrospun materials with characteristics that are particularly adapted for specific applications.

The geometry of the grounded target can be modified to produce a desired matrix. By varying the ground geometry, for instance having a planar or linear or multiple points ground, the direction of the streaming materials can be varied and customized to a particular application. For instance, a grounded target comprising a series of parallel lines can be used to orient electrospun materials in a specific direction. The grounded target can be a cylindrical mandrel whereby a tubular matrix is formed. The ground can be variable surface that can be controlled by a microprocessor that dictates a specific ground geometry that is programmed into it. Alternatively, the ground can be mounted on a frame that moves in the x, y, and z planes with respect to a stationary container, e.g., a syringe or micropipette tip.

Electrospinning allows great flexibility and allows for customizing the construct to virtually any shape needed. In shaping matrices, portions of the matrix may be sealed to one another by, for example, heat sealing, chemical sealing, and application of mechanical pressure or a combination thereof. The electrospun compositions may be shaped into shapes such as a skin patch, an intraperitoneal implant, a subdermal implant, the interior lining of a stent, a cardiovascular valve, a tendon, a ligament, a muscle implant, a nerve guide and the like.

The electrospinning process can also be modified for example by (i) using mixed solutions (for example, materials along with substances such as cells, growth factors, or both) in the same container to produce fibers composed of electrospun compounds as well as one or more substances to produce a "blend," and (ii) applying agents such as Teflon onto the target to facilitate the removal of electrospun compounds from the target (i.e. make the matrix more slippery so that the electrospun matrix does not stick to the target).

The various properties of the electrospun materials can be adjusted in accordance with the needs and specifications of the cells to be suspended and grown within them. The porosity, for instance, can be varied in accordance with the method of making the electrospun materials or matrix. Electrospinning a particular matrix, for instance, can be varied by fiber size and density. If the cells to be grown in the matrix require a high nutrient flow and waste expulsion, then a loose matrix can be created. On the other hand, if the tissue to be made requires a dense environment, then a dense matrix can be designed. Porosity can be manipulated by mixing salts or other extractable agents. Removing the salt will leave holes of defined sizes in the matrix.

One embodiment for appropriate conditions for electrospinning a matrix is as follows. For electrospinning a matrix by combining 45% collagen I, 15% elastin and 40% PLGA, the appropriate approximate ranges are: voltage 0-30,000 volts (10-100 kV potential preferably 15-30 kV); pH 7.0 to 8.0; temperature 20 to 40° C., e.g., room temperature of 25° C.; and the distance from the container to the grounded plate can range from about 1 cm to about 100 cm, preferably about 1 cm to 10 cm. In addition to depositing the charged fibers on the grounded plate, the fibers can be deposited onto another substrate such as a stainless steel mandrel. The mandrel can be rotated at 20-1000 rpm, preferably about 300-700 rpm.

Examples of naturally occurring materials include, but are not limited to, amino acids, peptides, denatured peptides such as gelatin from denatured collagen, polypeptides, proteins, carbohydrates, lipids, nucleic acids, glycoproteins, lipoproteins, glycolipids, glycosaminoglycans, and proteoglycans. In a preferred embodiment, the materials compound is an extracellular matrix material, including but not limited to collagen, fibrin, elastin, laminin, fibronectin, hyaluronic acid, chondroitin 4-sulfate, chondroitin 6-sulfate, dermatan sulfate, heparin sulfate, heparin, and keratan sulfate, and proteoglycans. These materials may be isolated from humans or other animals or cells. A preferred natural compound is collagen. Examples of collagen include, but are not limited to collagen I, collagen II, collagen III, collagen IV, collagen V, collagen VI, collagen VII, collagen VIII, collagen IX, and collagen X. Another preferred natural compound is elastin. Elastin fibers are responsible for the elastic properties of several tissues. Elastin is found, for example, in skin, blood vessels, and tissues of the lung where it imparts strength, elasticity and flexibility.

One class of synthetic polymer materials are biocompatible synthetic polymers. Such polymers include, but are not limited to, poly(urethanes), poly(siloxanes) or silicones, poly (ethylene), poly(vinyl pyrrolidone), poly(2-hydroxy ethyl methacrylate), poly(N-vinyl pyrrolidone), poly(methyl methacrylate), poly(vinyl alcohol) (PVA), poly(acrylic acid), poly(vinyl acetate), polyacrylamide, poly(ethylene-co-vinyl acetate), poly(ethylene glycol), poly(methacrylic acid), polylactic acid (PLA), polyglycolic acids (PGA), poly(lactide-co-glycolides) (PLGA), nylons, polyamides, polyanhydrides, poly(ethylene-co-vinyl alcohol) (EVOH), polycaprolactone, poly(vinyl acetate), polyvinylhydroxide, poly(ethylene oxide) (PEO) and polyorthoesters or any other similar synthetic polymers that may be developed that are biologically compatible. A preferred synthetic polymer is PGLA.

In matrices composed of electrospun elastin (for elasticity), electrospun collagen (to promote cell infiltration and lend mechanical integrity), and other components, such as PLGA, PGA, PLA, PEO, PVA, or other blends, the relative ratio of the different components in the matrix can be tailored to specific applications (e.g. more elastin, less collagen depending on the tissue to be engineered).

Electrospun matrices can be formed of electrospun fibers of synthetic polymers that are biologically compatible. The term "biologically compatible" includes copolymers and blends, and any other combinations of the forgoing either together or with other polymers. The use of these polymers will depend on given applications and specifications required. A more detailed discussion of these polymers and types of polymers is set forth in Brannon-Peppas, Lisa, "Polymers in Controlled Drug Delivery," Medical Plastics and Biomaterials, November 1997, which is incorporated herein by reference.

When both natural and synthetic materials are used in an electrospun matrix, the natural material component can range from about 5 percent to about 95 percent, preferably from about 25 percent to about 75 percent by weight. The synthetic material component can range from about 5 percent to about 95 percent, preferably from about 25 percent to about 75 percent by weight. In certain embodiments, both collagen and elastin can be included as natural material components, preferably with a predominance of collagen, e.g., greater than 40 percent of the natural material component. Ratios of collagen, elastin, and PLGA may be tailored to fit the application: for instances, normal levels of collagen and elastin vary from the more elastic vessels closer to the heart to less compliant vessels further from the heart. A vessel such as the aorta would have greater elastin content than a distal vessel. The percentages of collagen I, elastin, and other collagens (collagen III for blood vessels or collagen II, for instance, for cartilage) may be whatever is desired, as long as the molecular weight of these collagens is sufficient to form fibers in the electrospinning process. Ratios of collagen I may be from 40% to 80%, or 50%-100%. Elastin may also be used in higher ratios from 5% to 50%. PLGA or another synthetic biodegradable polymer may be used as desired in ratios from 5 to 80%. For a completely biological substrate, synthetic polymers may be omitted completely and only biological polymers may be used.

The compounds to be electrospun can be present in the solution at any concentration that will allow electrospinning. In one embodiment, the compounds may be electrospun are present in the solution at concentrations between 0 and about 1.000 g/ml. In another embodiment, the compounds to be electrospun are present in the solution at total solution concentrations between 10-15 w/v % (100-150 mg/ml or 0-0.1 g/L).

The compounds can be dissolved in any solvent that allows delivery of the compound to the orifice, tip of a syringe, under conditions that the compound is electrospun. Solvents useful for dissolving or suspending a material or a substance will depend on the compound. Electrospinning techniques often require more specific solvent conditions. For example, collagen can be electrodeposited as a solution or suspension in water, 2,2,2-trifluoroethanol, 1,1,1,3,3,3-hexafluoro-2-propanol (also known as hexafluoroisopropanol or HFIP), or combinations thereof. Fibrin monomer can be electrodeposited or electrospun from solvents such as urea, monochloroacetic acid, water, 2,2,2-trifluoroethanol, HFIP, or combinations thereof. Elastin can be electrodeposited as a solution or suspension in water, 2,2,2-trifluoroethanol, isopropanol, HFIP, or combinations thereof, such as isopropanol and water. In one desirable embodiment, elastin is electrospun from a solution of 70% isopropanol and 30% water containing 250 mg/ml of elastin. Other lower order alcohols, especially halogenated alcohols, may be used. Other solvents that may be used or combined with other solvents in electrospinning natural matrix materials include acetamide, N-methylformamide, N,N-dimethylformamide (DMF), dimethylsulfoxide (DMSO), dimethylacetamide, N-methyl pyrrolidone (NMP), acetic acid, trifluoroacetic acid, ethyl acetate, acetonitrile, trifluoroacetic anhydride, 1,1,1-trifluoroacetone, maleic acid, hexafluoroacetone. Organic solvents such as methanol, chloroform, and trifluoroethanol (TFE) and emulsifying agents.

The selection of a solvent is based in part on consideration of secondary forces that stabilize polymer-polymer interactions and the solvent's ability to replace these with strong polymer-solvent interactions. In the case of polypeptides such as collagen, and in the absence of covalent crosslinking, the principal secondary forces between chains are: (1) coulombic, resulting from attraction of fixed charges on the backbone and dictated by the primary structure (e.g., lysine and arginine residues will be positively charged at physiological pH, while aspartic or glutamic acid residues will be negatively charged); (2) dipole-dipole, resulting from interactions of permanent dipoles; the hydrogen bond, commonly found in polypeptides, is the strongest of such interactions; and (3) hydrophobic interactions, resulting from association of non-polar regions of the polypeptide due to a low tendency of non-polar species to interact favorably with polar water molecules. Therefore, solvents or solvent combinations that can favorably compete for these interactions can dissolve or disperse polypeptides. For example, HFIP and TFE possess a highly polar OH bond adjacent to a very hydrophobic fluorinated region. While not wanting to be bound by the following theories, it is believed that the alcohol portion can hydrogen bond with peptides, and can also solvate charges on the backbone, thus reducing Coulombic interactions between molecules. Additionally, the hydrophobic portions of these solvents can interact with hydrophobic domains in polypeptides, helping to resist the tendency of the latter to aggregate via hydrophobic interactions. It is further believed that solvents such as HFIP and TFE, due to their lower overall polarities compared to water, do not compete well for intramolecular hydrogen bonds that stabilize secondary structures such as an alpha helix. Consequently, alpha helices in these solvents are believed to be stabilized by virtue of stronger intramolecular hydrogen bonds. The stabilization of polypeptide secondary structures in these solvents is believed desirable, especially in the cases of collagen and elastin, to preserve the proper formation of collagen fibrils during electrospinning.

In one embodiment, the solvent has a relatively high vapor pressure to promote the stabilization of an electrospinning jet to create a fiber as the solvent evaporates. In embodiments involving higher boiling point solvents, it is often desirable to facilitate solvent evaporation by warming the spinning or spraying solution, and optionally the electrospinning stream itself, or by electrospinning in reduced atmospheric pressure. It is also believed that creation of a stable jet resulting in a fiber is facilitated by a high surface tension of the polymer/solvent mixture.

Similar to conventional electrospinning, midair electrospinning can be used which employs the same experimental set-up as other electrospinning techniques. However, in order to precipitate fibers before they reach the grounded target, the distance from the needle to the grounded target can be increased. For example, increasing the distance from the 10-30 cm to a distance of 30-40 cm. The field strength can be maintained or altered by increasing the applied potential at the needle tip. Increasing the distance from the needle tip to the grounded target allows the polymer jet to experience a longer "flight time." The added flight time, allows the solvent to be completely evaporated from the jet allowing the fibers to fully develop.

By varying the composition of the fibers being electrospun, it will be appreciated that fibers having different physical or chemical properties may be obtained. This can be accomplished either by spinning a liquid containing a plurality of components, each of which may contribute a desired characteristic to the finished product, or by simultaneously spinning fibers of different compositions from multiple liquid sources, that are then simultaneously deposited to form a matrix. The resulting matrix comprises layers of intermingled fibers of different compounds. This plurality of layers of different materials can convey a desired characteristic to the resulting composite matrix with each different layer providing a different property, for example one layer may contribute to elasticity while another layer contributes to the mechanical strength of the composite matrix. These methods can be used to create tissues with multiple layers such as blood vessels.

The electrospun matrix has an ultrastructure with a three-dimensional network that supports cell growth, proliferation, differentiation and development. The spatial distance between the fibers plays an important role in cells being able to obtain nutrients for growth as well as for allowing cell-cell interactions to occur. Thus, in various embodiments of the invention, the distance between the fibers may be about 50 nanometers, about 100 nanometers, about 150 nanometers, about 200 nanometers, about 250 nanometers, about 300 nanometers, about 350 nanometers, about 600 nanometers, about 750 nanometers, about 800 nanometers, about 850 nanometers, about 900 nanometers, about 950 nanometers, about 1000 nanometers (1 micron), 10 microns, 10 microns, 50 microns, about 100 microns, about 150 microns, about 200 microns, about 250 microns, about 300 microns, about 350 microns, about 400 microns, about 450 microns, or about 500 microns. In various embodiments the distance between the fibers may be less than 50 nanometers or greater than 500 microns and any length between the quoted ranges as well as integers.

Additionally, in various embodiments of the invention, the fibers can have a diameter of about 50 nanometers, about 100 nanometers, about 150 nanometers, about 200 nanometers, about 250 nanometers, about 300 nanometers, about 350 nanometers, about 600 nanometers, about 750 nanometers, about 800 nanometers, about 850 nanometers, about 900 nanometers, about 950 nanometers, about 1000 nanometers (1 micron), 50 microns, about 100 microns, about 150 microns, about 200 microns, about 250 microns, about 300 microns, about 350 microns, about 400 microns, about 450 microns, or about 500 microns, or the diameter may be less than 50 nanometers or greater than 500 microns and any diameter between the quoted ranges as well as integers.

The pore size in an electrospun matrix can also be controlled through manipulation of the composition of the material and the parameters of electrospinning. In some embodiments, the electrospun matrix has a pore size that is small enough to be impermeable to one or more types of cells. In one embodiment, the average pore diameter is about 500 nanometers or less. In another embodiment, the average pore diameter is about 1 micron or less. In another embodiment, the average pore diameter is about 2 microns or less. In another embodiment, the average pore diameter is about 5 microns or less. In another embodiment, the average pore diameter is about 8 microns or less. Some embodiments have pore sizes that do not impede cell infiltration. In another embodiment, the matrix has a pore size between about 0.1 and about 100 $\mu m^2$. In another embodiment, the matrix has a pore size between about 0.1 and about 50 $\mu m^2$. In another embodiment, the matrix has a pore size between about 1.0 $\mu m$ and about 25 $\mu m$. In another embodiment, the matrix has a pore size between about 1.0 $\mu m$ and about 5 $\mu m$. Infiltration can also be accomplished with implants with smaller pore sizes. The pore size of an electrospun matrix can be readily manipulated through control of process parameters, for example by controlling fiber deposition rate through electric field strength and mandrel motion, by varying solution concentration (and thus fiber size). Porosity can also be manipulated by mixing porogenic materials, such as salts or other extractable agents, the dissolution of which will leave holes of defined sizes in the matrix. The pore size can also be controlled by the amount of cross-linking present in the matrix.

The mechanical properties of the matrix will depend on the polymer molecular weight and polymer type/mixture. It will also depend on orientation of the fibers (preferential orientation can be obtained by changing speed of a rotating or translating surface during the fiber collection process), fiber diameter and entanglement. The cross-linking of the polymer will also effect its mechanical strength after the fabrication process.

The electrospun matrix can be cross linked to increase its stability and strength. The crosslinking can generally be conducted at room temperature and neutral pH conditions, however, the conditions may be varied to optimize the particular application and crosslinking chemistry utilized. For crosslinking using the EDC chemistry with NHS in MES/EtOH, pH of from 4.0 to 8.0 and temperatures from 0° C. to room temperature (25° C.) for two hours, can be used. It is known that higher temperatures are unpreferred for this chemistry due to decomposition of EDC. Similarly, basic pH (e.g., 8-14) is also unpreferred for this reason when using this chemistry. Other crosslinking chemistries can also be used for example, by soaking the electrospun matrix in 20% dextran solution (to reduce shrinking), followed by 1% glutaraldehyde solution. Yet other cross-linking chemistries involve using poly(ethylene glycol) (PEG) as a spacer in a crosslinking agent with an N-protected amino acid.

II. Decellularized Matrices

Natural biostructures, e.g. a blood vessel or an organ, can be obtained from a donor of the same species as the subject, for example, a human cadaver blood vessel or organ for a human recipient. The natural biostructure can also be obtained from a different species which includes, but is not limited to, monkeys, dogs, cats, mice, rats, cows, horses, pigs, goats and sheep. The natural biostructure can also be obtained from the subject requiring a reconstructed organ and can have the dysfunctional blood vessel removed and decellularized using the process described below. The decellularized blood vessel of the subject can be used as the three-dimensional scaffold to reconstruct an artificial blood vessel using cultured endothelial cells (e.g., human endothelial cells) isolated from the subject. In one embodiment, the endothelial cells are isolated from the human saphenous vein. In another embodiment, the endothelial cells can be produced from progenitor cells isolated from the blood or bone marrow of the subject. The artificial reconstructed blood vessel can be implanted back into the subject for further development.

Biostructures, e.g., blood vessels, or parts of blood vessels can be decellularized by removing the entire cellular and tissue content from the blood vessel. The decellularization process comprises a series of sequential extractions. One key feature of this extraction process is that harsh extraction that may disturb or destroy the complex infra-structure of the biostructure, be avoided. The first step involves removal of cellular debris and solubilization of the cell membrane. This is followed by solubilization of the nuclear cytoplasmic components an the nuclear components.

Preferably, the biostructure, e.g., an a blood vessel, is decellularized by removing the cell membrane and cellular debris surrounding the blood vessel using gentle mechanical disruption methods. The gentle mechanical disruption methods must be sufficient to disrupt the cellular membrane. However, the process of decellularization should avoid damage or disturbance of the biostructure's complex infra-structure. Gentle mechanical disruption methods include scraping the surface of the blood vessel, agitating the blood vessel, or stirring the blood vessel in a suitable volume of fluid, e.g., distilled water. In one embodiment, the gentle mechanical disruption method includes magnetically stirring (e.g., using a magnetic stir bar and a magnetic plate) the blood in a suitable volume of distilled water until the cell membrane is disrupted and the cellular debris has been removed from the blood vessel.

After the cell membrane has been removed, the nuclear and cytoplasmic components of the biostructure are removed. This can be performed by solubilizing the cellular and nuclear components without disrupting the infra-structure. To solubilize the nuclear components, non-ionic detergents or surfactants may be used. Examples of non-ionic detergents or surfactants include, but are not limited to, the Triton series, available from Rohm and Haas of Philadelphia, Pa., which includes Triton X-100, Triton N-101, Triton X-114, Triton X-405, Triton X-705, and Triton DF-16, available commercially from many vendors; the Tween series, such as monolaurate (Tween 20), monopalmitate (Tween 40), monooleate (Tween 80), and polyoxethylene-23-lauryl ether (Brij. 35), polyoxyethylene ether W-1 (Polyox), and the like, sodium cholate, deoxycholates, CHAPS, saponin, n-Decyl β-D-glucopuranoside, n-heptyl β-D glucopyranoside, n-Octyl-α-D-glucopyranoside and Nonidet P-40.

One skilled in the art will appreciate that a description of compounds belonging to the foregoing classifications, and vendors may be commercially obtained and may be found in "Chemical Classification, Emulsifiers and Detergents", McCutcheon's, Emulsifiers and Detergents, 1986, North American and International Editions, McCutcheon Division, MC Publishing Co., Glen Rock, N.J., U.S.A. and Judith Neugebauer, A Guide to the Properties and Uses of Detergents in Biology and Biochemistry, Calbiochem, Hoechst Celanese Corp., 1987. In one preferred embodiment, the non-ionic surfactant is the Triton series, preferably, Triton X-100.

The concentration of the non-ionic detergent may be altered depending on the type of biostructure being decellularized. For example, for delicate tissues, e.g., blood vessels, the concentration of the detergent should be decreased. Preferred concentrations ranges non-ionic detergent can be from about 0.001 to about 2.0% (w/v). More preferably, about 0.05 to about 1.0% (w/v). Even more preferably, about, 0.1% (w/v) to about 0.8% (w/v). Preferred concentrations of these range from about 0.001 to about 0.2% (w/v), with about 0.05 to about 0.1% (w/v) particular preferred.

The cytoskeletal component, comprising consisting of the dense cytoplasmic filament networks, intercellular complexes and apical microcellular structures, may be solubilized using alkaline solution, such as, ammonium hydroxide. Other alkaline solution consisting of ammonium salts or their derivatives may also be used to solubilize the cytoskeletal components. Examples of other suitable ammonium solutions include ammonium sulphate, ammonium acetate and ammonium hydroxide. In a preferred embodiment, ammonium hydroxide is used.

The concentration of the alkaline solutions, e.g., ammonium hydroxide, may be altered depending on the type of biostructure being decellularized. For example, for delicate tissues, e.g., blood vessels, the concentration of the detergent should be decreased. Preferred concentrations ranges can be from about 0.001 to about 2.0% (w/v). More preferably, about 0.005 to about 0.1% (w/v). Even more preferably, about, 0.01% (w/v) to about 0.08% (w/v).

The decellularized, lyophilized structure may be stored at a suitable temperature until required for use. Prior to use, the decellularized structure can be equilibrated in suitable isotonic buffer or cell culture medium. Suitable buffers include, but are not limited to, phosphate buffered saline (PBS), saline, MOPS, HEPES, Hank's Balanced Salt Solution, and the like. Suitable cell culture medium includes, but is not limited to, RPMI 1640, Fisher's, Iscove's, McCoy's, Dulbecco's medium, and the like.

III. Synthetic Matrices

The invention also pertains to generating artificial tissue constructs by seeding cultured tissue cells onto or into available biocompatible matrices. Biocompatible refers to materials that do not have toxic or injurious effects on biological functions. Biodegradable refers to material that can be absorbed or degraded in a patient's body. Representative materials for forming the biodegradable material include natural or synthetic polymers, such as, collagen, poly(alpha esters) such as poly(lactate acid), poly(glycolic acid), poly-orthoesters amd polyanhydrides and their copolymers, which degraded by hydrolysis at a controlled rate and are reabsorbed. These materials provide the maximum control of degradability, manageability, size and configuration. Preferred biodegradable polymer materials include polyglycolic acid and polyglactin, developed as absorbable synthetic suture material.

Polyglycolic acid and polyglactin fibers may be used as supplied by the manufacturer. Other biodegradable materials include, but are not limited to, cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, or copolymers or physical blends of these materials. The material may be impregnated with suitable antimicrobial agents and may be colored by a color additive to improve visibility and to aid in surgical procedures.

In some embodiments, attachment of the cells to the biocompatible substrate is enhanced by coating the matrix with compounds such as basement membrane components, agar, agarose, gelatin, gum arabic, collagens, fibronectin, laminin, glycosaminoglycans, mixtures thereof, and other materials having properties similar to biological matrix molecules known to those skilled in the art of cell culture. Mechanical and biochemical parameters ensure the matrix provide adequate support for the cells with subsequent growth and proliferation. Factors, including nutrients, growth factors, inducers of differentiation or dedifferentiation, products of secretion, immunomodulators, inhibitors of inflammation, regression factors, biologically active compounds which enhance or allow ingrowth of the lymphatic network or nerve fibers, and drugs, can be incorporated into the matrix or provided in conjunction with the matrix. Similarly, polymers containing peptides such as the attachment peptide RGD (Arg-Gly-Asp) can be synthesized for use in forming matrices.

Coating refers to coating or permeating a matrix with a material such as, liquefied copolymers (poly-DL-lactide co-glycolide 50:50 80 mg/ml methylene chloride) to alter its mechanical properties. Coating may be performed in one layer, or multiple layers until the desired mechanical properties are achieved. These shaping techniques may be employed in combination, for example, a polymeric matrix can be weaved, compression molded and glued together. Furthermore different polymeric materials shaped by different processes may be joined together to form a composite shape. The composite shape can be a laminar structure. For example, a polymeric matrix may be attached to one or more polymeric matrixes to form a multilayer polymeric matrix structure. The attachment may be performed by any suitable means such as gluing with a liquid polymer, stapling, suturing, or a combination of these methods. In addition, the polymeric matrix may be formed as a solid block and shaped by laser or other standard machining techniques to its desired final form. Laser shaping refers to the process of removing materials using a laser.

The polymers can be characterized for mechanical properties such as tensile strength using an Instron tester, for polymer molecular weight by gel permeation chromatography (GPC), glass transition temperature by differential scanning calorimetry (DSC) and bond structure by infrared (IR) spectroscopy; with respect to toxicology by initial screening tests involving Ames assays and in vitro teratogenicity assays, and implantation studies in animals for immunogenicity, inflammation, release and degradation studies. In vitro cell attachment and viability can be assessed using scanning electron microscopy, histology, and quantitative assessment with radioisotopes.

Substrates can be treated with additives or drugs prior to implantation (before or after the polymeric substrate is seeded with cells), e.g., to promote the formation of new tissue after implantation. Thus, for example, growth factors, cytokines, extracellular matrix components, and other bioactive materials can be added to the substrate to promote graft healing and formation of new tissue. Such additives will in general be selected according to the tissue or organ being reconstructed or augmented, to ensure that appropriate new tissue is formed in the engrafted organ or tissue (for examples of such additives for use in promoting bone healing, see, e.g., Kirker-Head, C. A. Vet. Surg. 24 (5): 408-19 (1995)). For example, vascular endothelial growth factor (VEGF, see, e.g., U.S. Pat. No. 5,654,273 herein incorporated by reference) can be employed to promote the formation of new vascular tissue. Growth factors and other additives (e.g., epidermal growth factor (EGF), heparin-binding epidermal-like growth factor (HBGF), fibroblast growth factor (FGF), cytokines, genes, proteins, and the like) can be added in amounts in excess of any amount of such growth factors (if any) which may be produced by the cells seeded on the substrate. Such additives are preferably provided in an amount sufficient to promote the formation of new tissue of a type appropriate to the tissue or organ, which is to be repaired or augmented (e.g., by causing or accelerating infiltration of host cells into the graft). Other useful additives include antibacterial agents such as antibiotics.

The biocompatible substrate may be shaped using methods such as, solvent casting, compression molding, filament drawing, meshing, leaching, weaving and coating. In solvent casting, a solution of one or more polymers in an appropriate solvent, such as methylene chloride, is cast as a branching pattern relief structure. After solvent evaporation, a thin film is obtained. In compression molding, the substrate is pressed at pressures up to 30,000 pounds per square inch into an appropriate pattern. Filament drawing involves drawing from the molten polymer and meshing involves forming a mesh by compressing fibers into a felt-like material. In leaching, a solution containing two materials is spread into a shape close to the final form of the tissue. Next a solvent is used to dissolve away one of the components, resulting in pore formation. (See Mikos, U.S. Pat. No. 5,514,378, hereby incorporated by reference).

In nucleation, thin films in the shape of the tissue are exposed to radioactive fission products that create tracks of radiation damaged material. Next, the polycarbonate sheets are etched with acid or base, turning the tracks of radiation-damaged material into pores. Finally, a laser may be used to shape and burn individual holes through many materials to form a tissue structure with uniform pore sizes. The substrate can be fabricated to have a controlled pore structure that allows nutrients from the culture medium to reach the deposited cell population. In vitro cell attachment and cell viability can be assessed using scanning electron microscopy, histology and quantitative assessment with radioisotopes.

Thus, the substrate can be shaped into any number of desirable configurations to satisfy any number of overall system, geometry or space restrictions. The matrix can be shaped to different sizes to conform to the necessary structures of different sized patients.

A substrate can also be permeated with a material, for example liquified copolymers (poly-DL-lactide co-glycolide 50:50 80 mg/ml methylene chloride) to alter its mechanical properties. This can be performed by coating one layer, or multiple layers until the desired mechanical properties are achieved.

The substrate can also be treated or seeded with various factors and proteins to control the degradation/absorption of the matrix in the subject. For instance, if the cells seeded within the substrate are slow-growing, then it is beneficial to maintain the matrix integrity for a long enough period of time to allow the cells enough time to regenerate and grow. On the other hand, if the cells are able to quickly reproduce and grow, then a short lived substrate could be desirable. Varying the concentration of aprotinin additives, aminocaproic acid, tranxemic acid, or similar fibrinolytic inhibitors or the degree of chemical cross-linking in the matrix could be used to precisely control this variable. The substrate could also be seeded with varying growth factors such as angiogenesis factor to promote a growth of blood vessels upon implantation.

VI. Functionalized Matrices

A matrix (e.g., an electrospun matrix, a natural decellularized matrix, or synthetic matrix) can be functionalized by incorporation of nanoparticles such as quantum dots (QD) coupled to therapeutic or biological agents. The matrix can also be functionalized to incorporate a contrast enhancing agent (e.g., gadolinium).

In one aspect, the invention pertains to releasing therapeutic or biological agent in a controlled manner at a target site. This is accomplished using quantum dots to which the therapeutic/biological agent is coupled. Quantum dots are a semiconductor nanocrystal with size-dependent optical and electronic properties. In particular, the band gap energy of a quantum dot varies with the diameter of the crystal. The average diameter of the QDs may be between about 1 to about 100 nm, between about 10-80 nm, and between about 25-40 nm. The coupled agent can be released by application of energy such as near infrared (NIR) irradiation from a laser source, which causes the bonds between the agent and the QD to break and thus releases the agent. This allows the release of the agent to be controlled by triggering its release upon application of energy. Quantum dots have been used as photostable biological fluorescent tags, semiconductors, and thermal therapy. The high transmission, scattering-limited attenuation, and minimal heating effects of quantum dots makes these suitable for the coupling of therapeutic/biological agents. In one embodiment, NIR CdSe quantum dots (Evident Technologies) can be used. These QDs have an optical absorption range of 700-1000 nm. NIR energy within this spectral region has been shown to penetrate tissue at depths up to 23 cm with no observable damage to the intervening tissue.

A matrix functionalized with a QD coupled to a therapeutic or biological agent can be used for controlled release of the therapeutic or biological agent at a target in the subject. The therapeutic or biological agent can be released by application of energy at a desired wavelength such as near infrared irradiation. Due to localized heating of the QD, ultrastructural changes cause the release of the coupled agent. The release kinetics can be varied according to the type of QD used and the wavelength of irradiation. The release kinetics can also be varied by altering the intensity and time of irradiation. For example, a QD (e.g., CdSe QD from Evident Technologies) coupled to encapsulated heparin can be incorporated into an electrospun matrix. Upon application of near infrared radiation at a wavelength of 700-1000 nm, the heparin is released in a controlled manner, as described in the examples below.

The studies in the examples section demonstrate the burst release of heparin over time when quantum dot conjugated heparin nanoparticles were irradiated by NIR irradiation. This system allows medical personnel to tune therapeutic/biological agent release rates post-operatively.

The emission spectra of quantum dots have linewidths as narrow as 25-30 nm depending on the size heterogeneity of the sample, and lineshapes that are symmetric, gaussian or nearly gaussian with an absence of a tailing region. The combination of tunability, narrow linewidths, and symmetric emission spectra without a tailing region provides for high resolution of multiply-sized quantum dots within a system and allows simultaneous examination of a variety of biological moieties tagged with QDs.

In addition, the range of excitation wavelengths of the quantum dots is broad and can be higher in energy than the emission wavelengths of all available quantum dots. Consequently, this allows the simultaneous excitation of all quantum dots in a system with a single light source. The ability to control the size of QDs enables one to construct QDs with fluorescent emissions at any wavelength in the UV-visible-IR region. Therefore, the colors (emissions) of QDs are tunable to any desired spectral wavelength. Furthermore, the emission spectra of monodisperse QDs have linewidths as narrow as 25-30 nm. The linewidths are dependent on the size heterogeneity of QDs in each preparation. In one embodiment, the QDs emit light in the ultraviolet wavelengths. In another embodiment, the QDs emit light in the visible wavelengths. In other embodiments, the QDs emit light in the near-infrared and the infrared wavelengths. Color of the light emitted by the QDs may be size-tunable and excitation energy tunable.

Many QDs are constructed of elements from groups II-VI, III-V and IV of the periodic table. They exhibit quantum confinement effects in their physical properties, and can be used in the composition of the invention. Exemplary materials suitable for use as quantum dots include, but are not limited to, ZnS, ZnSe, ZnTe, CdS, CdSe, CdTe, GaN, GaP, GaAs, GaSb, InP, InAs, InSb, AlS, AlP, AlAs, AlSb, PbS, PbSe, Ge, and Si and ternary and quaternary mixtures thereof. The quantum dots may further include an overcoating layer of a semiconductor having a greater band gap.

Any suitable therapeutic or biological agent such as genetic material, growth factors, cytokines, enzymes can be coupled to the QD. The therapeutic or biological agent can be released by the application of energy that breaks the bond between the QD and the coupled agent. The agent may also be released at a specific site as a function of biodegradation of the matrix in the surrounding environment over time.

Examples of a therapeutic or biological agent include, but are not limited to proteins growth factors, antibodies, nucleic acids molecules, carbohydrates, and the like. Growth factors useful in the present invention include, but are not limited to, transforming growth factor-alpha (TGF-α), transforming growth factor-beta (TGF-β), platelet-derived growth factors (PDGF), fibroblast growth factors (FGF), including FGF acidic isoforms 1 and 2, FGF basic form 2 and FGF 4, 8, 9 and 10, nerve growth factors (NGF) including NGF 2.5 s, NGF 7.0s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), granulocyte colony stimulating factor (G-CSF), insulin like growth factor (IGF) I and II, hepatocyte growth factor, glial neurotrophic growth factor (GDNF), stem cell factor (SCF), keratinocyte growth factor (KGF), transforming growth factors (TGF), including TGFs alpha, beta, beta1, beta2, beta3, skeletal growth factor, bone matrix derived growth factors, and bone derived growth factors and mixtures thereof.

Cytokines useful in the present invention include, but are not limited to, cardiotrophin, stromal cell derived factor, macrophage derived chemokine (MDC), melanoma growth stimulatory activity (MGSA), macrophage inflammatory proteins 1 alpha (MIP-1alpha), 2, 3 alpha, 3 beta, 4 and 5, IL-1, IL-2, IL-3, IL-4, IL-5, IL-6, IL-7, IL-8, IL-9, IL-10, IL-11, IL-12, IL-13, TNF-alpha, and TNF-beta. Immunoglobulins useful in the present invention include, but are not limited to, IgG, IgA, IgM, IgD, IgE, and mixtures thereof. Some preferred growth factors include VEGF (vascular endothelial growth factor), NGFs (nerve growth factors), PDGF-AA, PDGF-BB, PDGF-AB, FGFb, FGFa, and BGF.

Other molecules useful as therapeutic or biological agents include, but are not limited to, growth hormones, leptin, leukemia inhibitory factor (LIF), endostatin, thrombospondin, osteogenic protein-1, bone morphogenetic proteins 2 and 7, osteonectin, somatomedin-like peptide, osteocalcin, interferon alpha, interferon alpha A, interferon beta, interferon gamma, interferon 1 alpha.

Embodiments involving amino acids, peptides, polypeptides, and proteins may include any type or combinations of such molecules of any size and complexity. Examples include, but are not limited to structural proteins, enzymes, and peptide hormones. These compounds can serve a variety of functions. In some embodiments, the matrix may contain peptides containing a sequence that suppresses enzyme activity through competition for the active site. In other applications antigenic agents that promote an immune response and invoke immunity can be incorporated into a construct. In substances such as nucleic acids, any nucleic acid can be present. Examples include, but are not limited to deoxyribonucleic acid (DNA), and ribonucleic acid (RNA). Embodiments involving DNA include, but are not limited to, cDNA sequences, natural DNA sequences from any source, and sense or anti-sense oligonucleotides. For example, DNA can be naked (e.g., U.S. Pat. Nos. 5,580,859; 5,910,488) or complexed or encapsulated (e.g., U.S. Pat. Nos. 5,908,777; 5,787, 567). DNA can be present in vectors of any kind, for example in a viral or plasmid vector. In some embodiments, nucleic acids used will serve to promote or to inhibit the expression of genes in cells inside and/or outside the electrospun matrix. The nucleic acids can be in any form that is effective to enhance its uptake into cells.

The state of the electrospun matrix in relation to the incorporated therapeutic or biological agent can be controlled by the coupling chemistry, whether the therapeutic/biological agent is encapsulated, the selection of matrix compounds, the type of QDs used, solvent(s), and solubility of the matrix compounds in those solvents. These parameters can be manipulated to control the release of the therapeutic/biological agents. It is to be understood that therapeutic/biological agents may be entrapped or entangled within an electrospun matrix, bonded to a matrix, contained within cavities, enclosures, inclusions, or pockets, or structures of electrospun matrix (e.g. fibers, fibrils, particles) or externally bound to specific sites on the matrix.

The therapeutic or biological agent can also be entrapped, for example encapsulated in a polymer with the QD. The encapsulated QD-agent can be mixed with a solution comprising at least one natural compounds, and at least one synthetic compound and electrospun into the matrix.

In particular, the therapeutic or biological agent and the nanoparticles (e.g., quantum dot) can be entrapped or encapsulated to produce "nanocapsules." These nanocapsules containing the agent and the nanoparticle can be produce standard encapsulating techniques. Microencapsulation of agents generally involves three steps: (a) generating microcapsules enclosing the agents (e.g., by forming droplets of cell-containing liquid alginate followed by exposure to a solution of calcium chloride to form a solid gel), (b) coating the resulting gelled spheres with additional outer coatings (e.g., outer coatings comprising polylysine and/or polyornithine) to form a semipermeable membrane; and (c) liquefying the original core gel (e.g., by chelation using a solution of sodium citrate). The three steps are typically separated by washings in normal saline.

Alginates are linear polymers of mannuronic and guluronic acid residues. Monovalent cation alginate salts, e.g., Na-alginate, are generally soluble. Divalent cations such as $Ca^{2+}$, $Ba^{2+}$ or $Sr^{2+}$ tend to interact with guluronate, providing crosslinking and forming stable alginate gels. Alginate encapsulation techniques typically take advantage of the gelling of alginate in the presence of divalent cation solutions. Alginate encapsulation of agent-nanoparticles generally involves suspending the agent-nanoparticles to be encapsulated in a solution of a monovalent cation alginate salt, generating droplets of this solution, and contacting the droplets with a solution of divalent cations. The divalent cations interact with the alginate at the phase transition between the droplet and the divalent cation solution, resulting in the formation of a stable alginate gel matrix being formed. A variation of this technique is reported in U.S. Pat. No. 5,738,876, where the cell is suffused with a solution of multivalent ions (e.g., divalent cations) and then suspended in a solution of gelling polymer (e.g., alginate), to provide a coating of the polymer.

Another method of microencapsulating agent-nanoparticles is the alginate-polyamino acid technique. Cells are suspended in sodium alginate in saline, and droplets containing islets are produced. Droplets of cell-containing alginate flow into calcium chloride in saline. The negatively charged alginate droplets bind calcium and form a calcium alginate gel. The microcapsules are washed in saline and incubated with poly-L-lysine (PLL) or poly-L-ornithine (or combinations thereof); the positively charged poly-1-lysine and/or poly-L-ornithine displaces calcium ions and binds (ionic) negatively charged alginate, producing an outer poly-electrolyte membrane. A final coating of sodium alginate may be added by washing the microcapsules with a solution of sodium alginate, which ionically bonds to the poly-L-lysine and/or poly-L-omithine layer. See U.S. Pat. No. 4,391,909 to Lim et al (all U.S. patents referenced herein are intended to be incorporated herein in their entirety). This technique produces what has been termed a "single-wall" microcapsule. Preferred microcapsules are essentially round, small, and uniform in size. (Wolters et al., *J. Appli Biomater.* 3:281 (1992)).

The alginate-polylysine microcapsules can also then be incubated in sodium citrate to solubilize any calcium alginate that has not reacted with poly-1-lysine, i.e., to solubilize the internal core of sodium alginate containing the islet cells, thus producing a microcapsule with a liquefied cell-containing core portion. See Lim and Sun, Science 210:908 (1980). Such microcapsules are referred to herein as having "chelated", "hollow" or "liquid" cores. A "double-wall" microcapsule is produced by following the same procedure as for single-wall microcapsules, but prior to any incubation with sodium citrate, the microcapsules are again incubated with poly-1-lysine and sodium alginate.

Many alternative techniques used for encapsulating agents are known in the art and can be used with this invention. U.S. Pat. No. 5,084,350 discloses microcapsules enclosed in a larger matrix, where the microcapsules are liquefied once the microcapsules are within the larger matrix. Tsang et al., U.S. Pat. No. 4,663,286 discloses encapsulation using an alginate polymer, where the gel layer is cross-linked with a polycationic polymer such as polylysine, and a second layer formed using a second polycationic polymer (such as polyornithine); the second layer can then be coated by alginate. U.S. Pat. No. 5,762,959 to Soon-Shiong et al. discloses a microcapsule having a solid (non-chelated) alginate gel core of a defined ratio of calcium/barium alginates, with polymer material in the core. U.S. Pat. Nos. 5,801,033 and 5,573,934 to Hubbell et al. describe alginate/polylysine microspheres having a final polymeric coating (e.g., polyethylene glycol (PEG)); Sawhney et al., Biomaterials 13:863 (1991) describe alginate/polylysine microcapsules incorporating a graft copolymer of poly-1-lysine and polyethylene oxide on the microcapsule surface, to improve biocompatibility; U.S. Pat. No. 5,380,536 describes microcapsules with an outermost layer of water soluble non-ionic polymers such as polyethylene(oxide). U.S. Pat. No. 5,227,298 to Weber et al. describes a method for providing a second alginate gel coating to cells already coated with polylysine alginate; both alginate coatings are stabilized with polylysine. U.S. Pat. No. 5,578,314 to Weber et al. provides a method for microencapsulation using multiple coatings of purified alginate. U.S. Pat. No. 5,693,514 to Dorian et al. reports the use of a non-fibrogenic alginate, where the outer surface of the alginate coating is reacted with alkaline earth metal cations comprising calcium ions and/or magnesium ions, to form an alkaline earth metal alginate coating. The outer surface of the alginate coating is not reacted with polylysine. U.S. Pat. No. 5,846,530 to Soon-Shiong describes microcapsules containing cells that have been individually coated with polymerizable alginate, or polymerizable polycations such as polylysine, prior to encapsulation.

In one embodiment, heparin is coupled to the nanoparticle and the control the release kinetics of heparin can be monitored. One skilled in the art will appreciate that the control release kinetics depend on the capsulation parameters including nanocapsule size, heparin and quantum dot loading, and polymer composition. The mean diameter of the nanocapsules depends on the mixing velocity of the preparation process and viscosity of the preparation media. Nanocapsule size can be reduced by exposing the preparation to sonication over a range of about 30 second to about 120 seconds, increasing the sonication intensity from about 5 watts to about 20 watts, or by varying the ratios of organic polymer phase to aqueous heparin phase. Nanocapsule sizes can be characterized by scanning electron microscopy (SEM), coulter counter, and light scattering.

In one embodiment, the heparin can be conjugated to quantum dots by using an EDC/NHS chemical method. Various concentrations of heparin (ranging form 10-30 weight % polymer) and quantum dots can be used to determine optimal loading efficiency.

For polymer encapsulation, FDA approved biodegradable polymers (PLA, PLGA, PCL) can be used for the control of encapsulation and degradation of the nanocapsules in vivo.

The examples show that a burst of heparin release occurs using a broadband infrared (IR) source. Using measured quantities of QD-Heparin nanocapsules (NC) suspended in a physiological buffer, the influence of varying wavelengths, intensities, and irradiation times on the release kinetics can be determined. In one embodiment, the wavelength of irradiation used on the QD-Heparin can be in the near-infrared wavelength range, such as 700 nm, 800 nm, and 900 nm, using a filtered xenon source. The intensity of irradiation energy can be adjusted in incremental steps from 0 (control), 1 $mW/cm^2$, 10 $mW/cm^2$, 100 $mW/cm^2$, 1 $W/cm^2$, and 10 $W/cm^2$. The irradiation time can also be varied to determine the optimal irradiation time at each effective power intensity. The irradiation time can vary from 0 (control), 10, 60, 300, and 600 seconds of exposure.

The encapsulated QD-heparin will be released upon near infra-red (NIR) irradiation due to localized heating of the quantum dots which induces ultrastructural changes in the nanocapsules. The release kinetics will be varied at the target site by modulating the intensity and time of NIR irradiation to produce a controlled release of heparin. The quantitative measurement of heparin released from the nanocapsules can be measured over time (2, 4, 6, 12, and 24 hours and daily thereafter up to 30 days) and measured for its anti-factor Xa activity with a synthetic chromogenic substrate using a kit Rotachrom (Diagnostica Stago Inc).

In another aspect, the invention pertains to monitoring tissue remodeling a tissue engineered construct. Remodeling that takes place too slowly can result in pathologic response of surrounding tissues and compliance mismatch of the vessel. Rapid remodeling can result in premature failure of the engineered construct. Magnetic Resonance Imaging (MRI) is a powerful, non-invasive technique that can be used long term for monitoring the remodeling process. Nanoparticles (e.g., QD, image enhancing agents) can be easily bound both to decellularized matrices and electrospun matrices, and also embedded within nanofibers of electrospun matrices. The nanoparticles provide high MRI contrast, and due to their small size, will not interfere with normal biological processes. Organolanthanide complexes containing paramagnetic metals such as gadolinium (Gd) have been known to cause distortion in an electromagnetic field. When the protons in water interact with this distorted field, their magnetic properties significantly change such that they can be detected by MRI. The Examples demonstrate the enhanced imaging observed using MRI contrast with Gd functionalized nanoparticles bound to the surface and/or incorporated into the vascular matrices or nanocapsules. Other examples of contrast enhancing agents include, but are not limited to, rare earth metals such as, cerium, samarium, terbium, erbium, lutetium, scandium, barium, bismuth, cerium, dysprosium, europium, hafnium, indium, lanthanum, neodymium, niobium, praseodymium, strontium, tantalum, ytterbium, yttrium, and zirconium.

In one embodiment, the agents are joined to the matrix by peptide bonds. For example, nanoparticles can be incorporated as part of the matrix using EDC (1-ethyl-3(3-dimethly aminopropyl) carbodiimide) and sulfo-NHS (N-hydrocyl-sulfo-succinimide) to form peptide bonds. Various other know techniques can be used as described, for example, in Heumanson, Bioconjugate Techniques, Academic Press San Diego, Calif., 1996, herein incorporated by reference. For external functionalization, a peptide bond can be created between the matrix and carboxylated gadolinium nanoparticles using the EDC/sulpho-NHS method to form peptide bonds between the carboxylates and amino groups. The quantum dot coupled to a therapeutic/biological agent, a contrast enhancing agent, e.g., gadolinium, or both, can also be added internally to an electrospun matrix by incorporating each component into the solution with at least one natural compound and at least one synthetic compound. For example, solutions containing collagen I, elastin and PLGA, successfully incorporated the contrast enhancing agent gadolinium upon electrospinning as described in the Examples. The incorporation of the gadolinium into the matrix can be observed in vitro and in vivo using detection methods such as magnetic resonance imaging (MRI). Thus, a matrix functionalized with a contrasting agent allows the degradation of the matrix to be monitored.

Any type of functionalization method can be used. Examples of some possible functionalization chemistries include, but are not limited to, esterification (e.g., with acyl halides, acid anhydrides, carboxylic acids, or esters via interchange reactions), ether formation (for example, via the Wil-liamson ether synthesis), urethane formation via reactions with isocyanates, sulfonation with, for example, chlorosulfonic acid, and reaction of b-sulfato-ethylsulfonyl aniline to afford an amine derivative that can be converted to a diazo for reaction with a wide variety of compounds. Such chemistries can be used to attach a wide variety of substances to the electrospun matrix, including but not limited to crown ethers (Kimura et al., (1983) *J. Polym. Sci.* 21, 2777), enzymes (Chase et al. (1998) *Biotechnol. Appl. Biochem.*, 27, 205), and nucleotides (Overberger et al. (1989) *J. Polym. Sci.* 27, 3589).

V. Culturing Cells

The artificial tissue can be created by using allogenic cell populations derived from the subject's own tissue. The artificial tissue can also be xenogenic, where cell populations are derived from a mammalian species that are different from the subject. For example, tissue cells can be derived from mammals such as monkeys, dogs, cats, mice, rats, cows, horses, pigs, goats and sheep.

The isolated cells are preferably cells obtained by a swab or biopsy, from the subject's own tissue. A biopsy can be obtained by using a biopsy needle under a local anesthetic, which makes the procedure quick and simple. The small biopsy core of the isolated tissue can then be expanded and cultured to obtain the tissue cells. Cells from relatives or other donors of the same species can also be used with appropriate immunosuppression.

Methods for the isolation and culture of cells are discussed by Freshney, Culture of Animal Cells. A Manual of Basic Technique, 2d Ed., A. R. Liss, Inc., New York, 1987, Ch. 9, pp. 107-126. Cells may be isolated using techniques known to those skilled in the art. For example, the tissue can be cut into pieces, disaggregated mechanically and/or treated with digestive enzymes and/or chelating agents that weaken the connections between neighboring cells making it possible to disperse the tissue into a suspension of individual cells without appreciable cell breakage. If necessary, enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, DNase, pronase, and dispase. Mechanical disruption can also be accomplished by a number of methods including, but not limited to, scraping the surface of the tissue, the use of grinders, blenders, sieves, homogenizers, pressure cells, or insonators to name but a few.

Cell types include, but are not limited to, endothelial cells such as human endothelial cells, progenitor cells isolated from the peripheral blood bone that can be induced to differentiate into different cells, stem cells, committed stem cells, and/or differentiated cells may be used. Also, depending on the type of tissue or organ being made, specific types of committed stem cells can be used. For instance, myoblast cells can be used to build various muscle structures. Other types of committed stem cells can be used to make organs or organ-like tissue such as heart, kidney, liver, pancreas, spleen, bladder, ureter and urethra. Other cells include, but are not limited to, endothelial cells, muscle cells, smooth muscle cells, fibroblasts, osteoblasts, myoblasts, neuroblasts, fibroblasts, glioblasts; germ cells, hepatocytes, chondrocytes, keratinocytes, cardiac muscle cells, connective tissue cells, epithelial cells, endothelial cells, hormone-secreting cells, cells of the immune system, neurons, cells from the heart, kidney, liver, pancreas, spleen, bladder, ureter and urethra, and the like. In some embodiments it is unnecessary to pre-select the type of stem cell that is to be used, because many types of stem cells can be induced to differentiate in an organ specific pattern once delivered to a given organ. For example, a stem cell delivered to the liver can be induced to become a liver cell simply by placing the stem cell within the biochemical environment of the liver.

Examples also include cells that have been genetically engineered, transformed cells, and immortalized cells. One example of genetically engineered cells useful in the present invention is a genetically engineered cell that makes and secretes one or more desired molecules. When matrices comprising genetically engineered cells are implanted in an organism, the molecules produced can produce a local effect or a systemic effect, and can include the molecules identified above as possible substances.

Cells may produce substances that inhibit or stimulate inflammation; facilitate healing; resist immunorejection; provide hormone replacement; replace neurotransmitters; inhibit or destroy cancer cells; promote cell growth; inhibit or stimulate formation of blood vessels; augment tissue; and to supplement or replace the following tissue, neurons, skin, synovial fluid, tendons, cartilage, ligaments, bone, muscle, organs, dura, blood vessels, bone marrow, and extracellular matrix.

The shape of the extracellular matrix may help send signals to the cells to grow and reproduce in a specific type of desired way. Other factors and differentiation inducers may be added to the matrix to promote specific types of cell growth.

Once the tissue has been reduced to a suspension of individual cells, the suspension can be fractionated into subpopulations from which the cells elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counterstreaming centrifugation), unit gravity separation, countercurrent distribution, electrophoresis and fluorescence-activated cell sorting (see e.g. Freshney, (1987) Culture of Animal Cells. A Manual of Basic Techniques, 2d Ed., A. R. Liss, Inc., New York, Ch. 11 and 12, pp. 137-168). For example, salivary cells may be enriched by fluorescence-activated cell sorting. Magnetic sorting may also be used.

Cell fractionation may also be desirable, for example, when the donor has diseases such as cancer or tumor. A cell population may be sorted to separate the cancer or tumor cells from normal noncancerous cells. The normal noncancerous cells, isolated from one or more sorting techniques, may then be used for tissue reconstruction.

Isolated cells can be cultured in vitro to increase the number of cells available for seeding into the biocompatible substrate. To prevent an immunological response after implantation of the artificial tissue construct, the subject may be treated with immunosuppressive agents such as, cyclosporin or FK506.

Isolated cells may be transfected with a nucleic acid sequence. Useful nucleic acid sequences may be, for example, genetic sequences which reduce or eliminate an immune response in the host. For example, the expression of cell surface antigens such as class I and class II histocompatibility antigens may be suppressed. In addition, transfection could also be used for gene delivery. Cells may be transfected with specific genes prior to seeding onto the biocompatible substitute. Thus, the cultured cells can be engineered to express gene products that would produce a desired protein that helps ameliorate a particular disorder.

The tissue cells grown on the electrospun matrix substrate may be genetically engineered to produce gene products beneficial to implantation, e.g., anti-inflammatory factors, e.g., anti-GM-CSF, anti-TNF, anti-IL-1, and anti-IL-2. Alternatively, the tissue cells may be genetically engineered to "knock out" expression of native gene products that promote inflammation, e.g., GM-CSF, TNF, IL-1, IL-2, or "knock out" expression of MHC in order to lower the risk of rejection.

Methods for genetically engineering cells for example with retroviral vectors, adenoviral vectors, adeno-associated viral vectors, polyethylene glycol, or other methods known to those skilled in the art can be used. These include using expression vectors which transport and express nucleic acid molecules in the cells. (See Geoddel; *Gene Expression Technology: Methods in Enzymology* 185, Academic Press, San Diego, Calif. (1990).

Vector DNA is introduced into prokaryotic or eukaryotic cells via conventional transformation or transfection techniques. Suitable methods for transforming or transfecting host cells can be found in Sambrook et al. *Molecular Cloning: A Laboratory Manual*, 2nd Edition, Cold Spring Harbor Laboratory press (1989), and other laboratory textbooks.

Once seeded onto the matrix, the cells will proliferate and develop on the matrix to form a tissue layer. Importantly, because the matrix has an infra-structure that permits culture medium to reach the tissue layer, the cell population continues to grow, divide, and remain functionally active to develop into a tissue that has a morphology which resembles the analogous structure in vivo.

It is important to recreate, in culture, the cellular microenvironment found in vivo for the particular tissue being engineered. By using a matrix that retains an infra-structure that is similar or the same as an in vivo tissue structure, the optimum environment for cell-cell interactions, development and differentiation of cell populations, is created.

Growth factors and regulatory factors can be added to the media to enhance, alter or modulate proliferation and cell maturation and differentiation in the cultures. The growth and activity of cells in culture can be affected by a variety of growth factors such as growth hormone, somatomedins, colony stimulating factors, erythropoietin, epidermal growth factor, hepatic erythropoietic factor (hepatopoietin), and like. Other factors which regulate proliferation and/or differentiation include prostaglandins, interleukins, and naturally-occurring chalones.

The artificial tissue constructs of the invention can be used in a variety of applications. For example, the artificial tissue constructs can be implanted into a subject to replace or augment existing tissue. The subject can be monitored after implantation of the artificial tissue or organ, for amelioration of the disorder.

The artificial tissue can be used in vitro to screen a wide variety of compounds, for effectiveness and cytotoxicity of pharmaceutical agents, chemical agents, growth/regulatory factors. The cultures can be maintained in vitro and exposed to the compound to be tested. The activity of a cytotoxic compound can be measured by its ability to damage or kill cells in culture. This may readily be assessed by vital staining techniques. The effect of growth/regulatory factors may be assessed by analyzing the cellular content of the matrix, e.g., by total cell counts, and differential cell counts. This may be accomplished using standard cytological and/or histological techniques including the use of immunocytochemical techniques employing antibodies that define type-specific cellular antigens. The effect of various drugs on normal cells cultured in the artificial tissue may be assessed.

VI. Preconditioning Chamber

Blood vessels can be created in a preconditioning chamber as shown in FIG. 11, which is one embodiment of a preconditioning chamber. The dimensions of the chamber are such that it can hold a matrix seeded with cells. Suitable size ranges can range form about 200×200×600 mm, 100×100×300 mm, preferably about 50×50×150 mm. FIG. 11A shows the top view of one embodiment of the preconditioning chamber 40 with a first and second long wall 42 and a first and second short wall 44. The first and second short walls 44 each have an opening 46 that accommodates a platform 48 that can hold a vessel 50 having an attachment element 52. The matrix seeded with cells (shown in hashed lines) can be attached to the first and second attachment ends 53 of the vessel. The vessel is operatively linked to a fluid flow system (not shown) that can pump biological fluid through one end of the vessel 50, through the attached tubular matrix seeded with cells, and through the other end of the vessel in a continuous manner. FIG. 11B shows the side view of the preconditioning chamber of FIG. 11A and FIG. 11C shows a traverse view FIG. 11A.

The biological fluid can be pumped using any pumping mechanism such as a gear pump. The chamber can further comprise a rotation device that can be used to rotate the chamber at a desired angle for example, by 45°, 90°, 180°, and 360°. The rotation device can be manually operated or can be automated such that the chamber is rotated at a desired speed and at a desired time. In other embodiments, the chamber can be a multichambered and can house more than one blood vessel. In other embodiments, both the inside and the outside of the seeded matrix can be preconditioned using the preconditioning chamber of the invention. In such embodiments, the chamber is filled with a volume of preconditioning fluid that can cover the attached seeded matrix. The fluid flow of the biological fluid on the outside of the matrix can be controlled by the same or a separate mechanism than the fluid flow on the inside of the matrix. The biological fluid on the outside may be the same as the biological fluid on the inside. Alternatively, or the biological fluid on the outside may be the different than the biological fluid on the inside. The fluid flow parameters an be the same for the biological fluid on the inside and the outside, or can be different.

The walls of the preconditioning chamber can be made of any suitable material such as plexiglass, plastics and the like as long as the material does not react with a biological fluid. The biological fluid can be moved through the inside surface (lumen) of the attached matrix as a continuous unidirectional flow, for example with a continuous flow-rate that can be incremented over time to induce a wall shear in the range of about 1 dyne/cm$^2$ to about 30 dynes/cm$^2$. The step of preconditioning the matrix can also involve moving the biological fluid through the inside surface of the attached matrix as a pulsed flow, for example, a pulsed flow that has a pulse-rate which is incremented over time to induce a wall shear in the range of about 10 dynes/cm$^2$ to about 45 dynes/cm$^2$. The pulse-rate can be incremented over time to induce a wall pressure distribution in the engineered blood vessel in the range of about 60 to about 200 mmHg. A different of the same biological fluid can also be used to precondition the outside of the matrix.

The biological fluid can have a composition and viscosity that mimics blood so that the engineered blood vessels are exposed same fluid flow dynamics as native blood vessels. Examples of biological fluids can include any buffer, medium of physiological fluid (e.g., DMEM with 10% FCS) The viscosity of the fluids can be altered by adding high molecular weight proteins such as 100 kDa dextran. Other molecular weight dextrans can also be used. It will be appreciated that the amount of dextran to be used depends on the molecular weight and can range from about 10%, 20%, 30%, 40%, 50%, and 60%. The composition may also be varied by adding other blood like constituents such as salts.

It will be appreciated that the preconditioning chamber can be used to precondition other tissues such as a heart valve. In vivo heart valves function under a dynamic flow environment, however most studies of leaflet cell metabolism have been carried out in static culture. The present methods mimic the activity of the seeded cells under such dynamic flow conditions as the flow may effect the regulation and expression of proteins such as collagen and elastin and glycosaminoglycan biosynthesis, produced by the seeded cells. In addition, the dynamic flow may effect the orientation of the cells on the valve leaflet.

The engineered valve can be created from a matrix seeded with endothelial cells and muscle cells that have been differentiated from progenitor cells that have been isolated from the peripheral blood circulation of the subject. The seeded valve matrix can then be exposed to sterile pulsatile flow system that mimic the dynamic flow environment of the heart e.g., the aortic valve.

Thus, methods and compositions of the invention take into account the adherence of repopulating cells on valve leaflets and their functionality when exposed to the high stress environment of blood flow in the heart. Valve leaflets are exposed to several mechanical forces which may influence how well cells will grow and function on the leaflets. When the valve is closed during diastole, the valve must support systemic pressure, a normal stress that would directly affect the cells on the aortic side on the leaflets (lamina fibrosa). This stress may also be transmitted to cells within the tissue aligned to collagen fibers. The ventricular surface of the leaflets, on the other hand, experiences a fluid shear stress during systole when blood is ejected through the valve. Numerical simulations of flow through a stented valve indicate that this shear stress may exceed 130 dyne/cm$^2$ at peak systole. Bending stresses arise from the motion of the leaflets during the course of the cardiac cycle, and may effect cell behavior and function.

The effects of flow rate, cycle frequency, and pressure on the seeded cells, can be examined. This permits optimization of conditions for retention of cells seeded onto the leaflet matrix, and investigation of how these physical forces affect the cellular activity, adherence, and function of these cells. The pulsatile flow can be used to modify both exogenous cell adhesion, migration, and activity so that the optimal cell densities and function typical of native valve leaflet, is achieved.

Though the cellular events altered by combinations of shear stress, pressure, and cycle frequency are numerous, of particular interest in considering how flow conditioning might affect the interactions of exogenous cells with a tissue matrix include adhesiveness of cells, proliferation rates, migration rates, and the ability of the cells to make extracellular matrix proteins. Among the adhesion proteins found on cell surfaces the strongest forces between cells and the extracellular matrix are mediated by the integrins (Ley et al. (1995) *J. Immunol.* 155:525-528). Each of these proteins has specificity for particular matrix proteins: such as collagens, fibronectins, laminins and vitronectins. Synthesis of integrins and expression of their mRNAs is regulated in endothelial cells at even very low levels of shear stress 1.5 dyne/cm$^2$ of shear (Ando et al., (1994) *Am. J. Physiol. Cell Pysiol.* 267: C679-C687). Flow not only affects integrin synthesis but is also instrumental in reorganizing the localization of these proteins on the cell surface to increases resistance to detachment (Davies (1995) *Physiol Rev* 75:519-560). Cardiac pressure overloading may directly cause ventricular cells to proliferate and increase synthesis and deposition of collagens. Other cells may also be pressure-responsive and may demonstrate altered protein synthesis in response to a force.

A preconditioning chamber that physically preconditions a viable heart valve prior to implantation significantly improves the overall quality of the heart valve and makes it less prone to thrombogenesis, calcification and failure. The application of optimal conditions of flow, pulsation rate, and pressure therefore provides an implant which displays physiologic levels of cellular activity, and provide a graft with extended durability and performance.

The preconditioning chamber is designed to mimic the flow dynamics of the heart. The seeded matrix can be attached to an attachment site in the chamber. A pulsating pump, e.g., a piston pump (Vivitro Model SPS 3891) can be used to drive the pulsatile flow, since its motion can be programmed with a waveform generator (Vivitro Model WG 5891), allowing the flow waveform to be changed easily. The piston can displace the physiological fluid through the attached valve. The piston motion can be programmed to produce a flow that simulates the cardiac cycle, but with variable frequency from 60-120 bpm and a cardiac output of 2-7.5 L/min.

The endothelial cells and smooth muscle cells seeded on the matrix can be exposed to shear stress in the range of about 1 to about 50 dyne/cm$^2$, and preferably about 10 to about 25 dyne/cm$^2$, and most preferably about 15 dyne/cm$^2$. Whether the cell will shear away from the leaflet surface depends upon the number and strength of the bonds that anchor the cell to the surface. Most cell adhesion research has focused on the cells of the immune system, such as leukocytes and neutrophils, which can roll along the endothelium to find and adhere at sites of inflammation. The mechanical, biochemical and morphological changes to the preconditioned cells as be assessed as described in the examples.

VII. Use of Matrices

The methods and compositions of the invention can be used for localized delivery of therapeutic/biological agents, as well as controlled release of such agents at the target site in a subject.

(i) Vascular Constructs

The methods and compositions of the invention can be used to construct blood vessels. One application of the electrospun matrices or decellularized matrices is in the formation of medium and small diameter vascular constructs. Some preferred materials for this embodiment are collagen and elastin, especially collagen type I and collagen type III. Examples of vascular constructs include, but are not limited to coronary vessels for bypass or graft, femoral artery, popliteal artery, brachial artery, tibial artery, radial artery or corresponding veins. The electrospun material is useful especially when combined with endothelial cells and smooth muscle cells. More complicated shapes including tapered and/or branched vessels can also be constructed. A different-shaped mandrel is necessary to wind the large fibers around or to orient the electrospun polymer.

Some of the complications with vascular matrices are (1) thrombus formation and (2) inability to quantitatively monitor integration of the vascular graft in vivo. Problems with thrombus formation are some of the most difficult challenges resulting in frequent failure of vascular grafts. Heparin, a powerful anticoagulation agent, is commonly administered clinically to avoid thrombus formation. However, systemic use of heparin carries a certain amount of risk, thus locally administered heparin is preferred. The methods and compositions of the invention can be used to overcome the lack of control of drug release by utilizing quantum dot based nanotechnology. Specifically, the acceleration of release of anticoagulants such as heparin at the target location (vascular graft) by triggering their release from quantum dots using NIR energy. This allows the release kinetics of the anticoagulant e.g., heparin to be modulated.

The studies shown in the Examples section demonstrated that near infrared (NIR) quantum dot conjugated heparin can be successfully incorporated into the nanoparticles and vascular scaffolds to enable the controlled release (or burst release) of heparin over time initiated by near infrared exposure.

MRI contrasting agents such as gadolinium were also successfully attached to, or incorporated into the scaffold to enhance visualization. Thus, controlled release of heparin from vascular scaffolds can be achieved using near infrared (NIR) quantum dots and heparin and (2) nanocontrast agents functionalized on, or incorporated into, the vascular scaffold can be used to evaluate and monitor heparin release.

(ii) Tissue Organ Constructs

The methods and compositions of the invention can be used to construct engineered tissue organ constructs, or parts of organ constructs e.g., heart, heart valves, liver, kidney, and the like. The ability to use electrospun materials and matrices to bioengineer tissue or organs creates a wide variety of bioengineered tissue replacement applications. Examples of bioengineered components include, but are not limited to, blood vessels, heart, liver, kidney, skeletal muscle, cardiac muscle, and nerve guides. In some embodiments, such matrices are combined with therapeutic agents that improve the function of the implant. For example, antibiotics, anti-inflammatories, local anesthetics or combinations thereof, can be added to the matrix of a bioengineered organ to speed the healing process and reduce discomfort.

(iii) Substance Delivery

The methods and compositions of the invention can be used to delivery one or more therapeutic agents to a desired location. The present compositions can be used to deliver therapeutic agents to an in vivo location, an in vitro location, or other locations. The present compositions can be administered to these locations using any method. Alternatively, an electrospun matrix containing cells can be implanted in a body and used to deliver molecules produced by the cells after implantation.

The selection of the therapeutic agent and the method by which the agent is combined with the electrospun material affects the substance release profile. To the extent that the agents are immobilized by the electrospun matrix, the release rate is more closely related to the rate at which the electrospun material degrades. For example, a therapeutic agent can be electrospun with the matrix and trapped within an electrospun filaments, in such an instance, the release kinetics are determined by the rate at which the electrospun matrix degrades. In other embodiment, the therapeutic agent can be coupled to a QD and electrospun into the matrix. In such instances, the release kinetics are controlled by the application of irradiation energy that disrupts the coupling bonds between the therapeutic agent and the QD to release the therapeutic agent. In other embodiments, the therapeutic agents can be encapsulated within a polymer matrix and the encapsulated therapeutic agent added during the electrospinning process such that the encapsulated therapeutic agents is embedded within the matrix. Under these circumstances, the release kinetics depend on the rate at which the electrospun matrix degrades, as well as the nature and degradation properties of the encapsulating polymer. In yet other embodiments, the therapeutic agent can be coupled to a quantum dot and encapsulated and then electrospun to become embedded within the matrix.

Under such circumstances, the release kinetics are controlled by the application of irradiation energy that disrupts the coupling bonds between the therapeutic agent and the QD to release the therapeutic agent. The porosity of the electrospun material can also be regulated, which affects the rate of release of a substance.

Chemicals that affect cell function, such as oligonucleotides, promoters or inhibitors of cell adhesion, hormones, and growth factors, for example, can be incorporated into the electrospun matrix and the release of those substances from the electrospun matrix can provide a means of controlling expression or other functions of cells in the electrospun matrix.

Release kinetics in some embodiments are manipulated by cross-linking electrospun material through any means. In some embodiments, cross-linking will alter, for example, the rate at which the electrospun matrix degrades or the rate at which a compound is released from the electrospun matrix by increasing structural rigidity and delaying subsequent dissolution of the electrospun matrix. Electrospun matrix can be formed in the presence of cross-linking agents or can be treated with cross-linking agents after electrospinning. Any technique for cross-linking materials may be used as known to one of ordinary skill in the art. Examples of cross-linking agents include, but are not limited to, condensing agents such as aldehydes e.g., glutaraldehyde, carbodiimide EDC (1-ethyl-3(3 dimethyl aminopropyl)), photosensitive materials that cross-link upon exposure to specific wavelengths of light, osmium tetroxide, carbodiimide hydrochloride, and NHS (n-hydroxysuccinimide).

The release kinetics of the matrix is also controlled by manipulating the physical and chemical composition of the electrospun matrix. For example, small fibers of PLGA are more susceptible to hydrolysis than larger diameter fibers of PLGA. An agent delivered within an electrospun material composed of smaller PLGA fibers is released more quickly than when prepared within a matrix composed of larger diameter PLGA fibers.

Physical processing of the electrospun matrix is another way to manipulate release kinetics. In some embodiments, mechanical forces, such as compression, applied to an electrospun matrix hasten the breakdown of the matrix by altering the crystalline structure of the matrix. The structure of the matrix is thus another parameter that can be manipulated to affect release kinetics. Polyurethanes and other elastic materials such as poly(ethylene-co-vinyl acetate), silicones, and polydienes (e.g., polyisoprene), polycaprolactone, polyglycolic acid and related polymers are examples of materials whose release rate can be altered by mechanical strain.

VIII. Storage

A matrix can be stored and used shortly before implantation by seeding it with cells. Many electrospun matrices are dry once they are spun and can be storage in a dry or frozen state. Storage conditions will depend on the electrospun compounds used and whether a therapeutic agent is incorporated onto or into the matrix. In embodiments where a therapeutic agent is incorporated, the matrix can be stored at temperatures below 0° C., under vacuum, or in a lyophilized state. Other storage conditions can be used, for example, at room temperature, in darkness, in vacuum or under reduced pressure, under inert atmospheres, at refrigerator temperature, in aqueous or other liquid solutions, or in powdered form depending on the materials in and on the matrix.

The matrices may be sterilized through conventional means known to one of ordinary skill in the art such as radiation, and heat. The matrices can also be combined with bacteriostatic agents, such as thimerosal, to inhibit bacterial growth. In some embodiments, the compositions can be treated with chemicals, solutions, or processes that confer stability in storage and transport.

Other embodiments and used of the invention will be apparent to those skilled in the art from consideration of the specification and practice of the invention disclosed herein. All U.S. Patents and other references noted herein for whatever reason are specifically incorporated by reference. The specification and examples should be considered exemplary only with the true scope and spirit of the invention indicated by the following claims.

EXAMPLES

Example 1

Methods and Materials

Materials

Unless otherwise stated, all chemicals were purchased from Sigma (St. Louis, Mo.). ECL buffers and 125I-Sodium were purchased from PerkinElmer NEN (Boston, Mass.). Collagenase type II (1 mg/ml) was purchased from Boehringer Mannheim (Mannheim, Germany). Endothelial medium (EBM-2) was purchased from Cambrex Bio Science (Walkersville, Md.). PCR reagents and primers, M199 medium, fetal bovine serum (FBS) and penicillin were purchased from Life Technologies (Gaithersburg, Md.). Basic Fibroblast Growth Factor (bFGF) was a gift from Judith Abraham, (Scios Nova, Calif.). Anti human CD31, anti von-Willebrand factor (vWF) and anti smooth muscle actin antibodies were purchased from DACO (Glostrup, Denmark). Anti-CD105 antibodies were purchased from BD Pharmingen (San Diego, Calif.). Anti Flk-1 antibodies were purchased from Santa Cruz (Santa Cruz, Calif.). FITC-conjugated avidin was purchased from Vector Laboratories (Burlingame, Calif.). Athymic mice were purchased from Jackson Labs (Bar Harbor, Me.).

Methods (i) Scaffold Preparation

Electrospun nanofiber scaffolds have been developed using a solution of collagen type I, elastin, and poly(D,L-lactide-co-glycolide) (PLGA, mol. ratio 50:50, Mw 110,000) (Boeringer-Ingelheim, Germany). Collagen type I from calf skin (Elastin Products Company, Owensville, Mo.), elastin from ligamentum nuchae (bovine neck ligament), (Elastin Products Company, Owensville, Mo.), and PLGA are mixed at a relative concentration by weight of 45% collagen, 40% PLGA, and 15% elastin. The solutes are dissolved in 1,1,1,3,3,3-hexafluoro-2-propanol (99+%) (Sigma Chemical Company, St. Louis, Mo.) at a total solution concentration of 15 w/v % (150 mg/mL). High molecular weight PLGA, previously used for electrospinning tissue scaffolds is added to the solution to increase mechanical strength of the scaffold and increase viscosity and spinning characteristics of the solution.

Physically, the electrospinning method requires a high voltage power supply, a syringe pump, a polymer solution or melt to be spun, and a grounded collection surface. During electrospinning, the grounded mandrel rotates while the stage translates to ensure even deposition of fibers onto the mandrel surface. Solutions were electrospun using a high voltage power supply (Spellman High Voltage, Hauppauge, N.Y.) at 25 kV potential between the solution tip and the grounded surface. The solution was delivered with a 5 mL syringe through an 18 gauge blunt tip needle at a flow rate of 3.0 mL/hr using a syringe pump. Fibers collect onto a grounded mandrel at a distance of 15 cm from the tip. The mandrel is a 303 stainless steel rod which is rotated at 500 rpm. The mandrel size is initially 4.75 mm to allow for contraction of the graft due to crosslinking. Uniform scaffolds of 120 mm length were created using 2.4 mL of solution. This apparatus is shown schematically in FIG. 1.

Scaffolds were further crosslinked for increased stability and strength, using two crosslinking methods. The scaffolds were soaked for two minutes in 20% dextran solution in phosphate buffered saline prior to crosslinking to reduce hydration-induced swelling and contraction of the scaffold. The scaffolds were crosslinked by immersion in 1) 1% glutaraldehyde solution and 2) EDC/NHS in MES/EtOH solution for 2 hours at room temperature. These data show that it is possible to fabricate vascular scaffolds from biological polymers with mechanics and structure similar to decellularized scaffolds and native arteries.

FIG. 1. shows the electrospinning apparatus in which fibers deposit onto a grounded collection surface as solvent evaporates due to increasing surface area/volume ratio of solution. The electrostatic field causes splaying of solution, and solutions of sufficient viscosity and surface tension form fibrous mats which adhere to grounded surfaces.

(ii) Cell Seeding

A confluent monolayer of endothelial cells is the most important barrier against thrombus formation, and endothelial cell mediated NO production is important to maintain vascular tone. Cells were seeded with a mouse endothelial cell line MS1 cells. The cells routinely cultured in tissue culture polystyrene flasks at 37° C. under 5% CO2 atmosphere were harvested after the treatment with 0.1% trypsin-EDTA. The scaffolds were mounted in tissue culture dishes. After equilibration with PBS, the cells (1×105/mL) were seeded to the scaffolds. The culture medium used was DMEM medium containing 10% FBS, and antibiotics. After 2 days culture, the cell attachment was assessed using scanning electron microscopy.

(iii) Microscopy

The relative quantity and distribution of collagen and elastin in a vascular scaffold is important to the mechanical properties and function of the seeded graft (FIG. 1). To determine the distribution of components of the scaffolds, histo- and immunohistochemical analyses were performed to identify collagen and elastin distribution.

(iv) Biocompatibility Testing (Cell Viability and Proliferation)

Long-term viability of cells is necessary for the seeded scaffold to remodel itself into a viable, patent vessel. Standard methods were employed to assess viability and proliferation. To test for cell viability, constructs were placed in 24-well plates with approximately 100 mg of material per well. Four different types of material were tested for biocompatibility and cell survival, with one negative control well with no material: (1) GA-NFS (1% glutaraldehyde crosslinked electrospun scaffold); (2) EDC-NFS (EDC-crosslinked electrospun scaffold); (3) nBV (natural blood vessel, decellularized); (4) Latex (latex rubber, positive control).

Endothelial cells were seeded in the wells on a scaffold for testing via the direct contact method. For cell viability, cell layers were rinsed with PBS. 0.005% w/v neutral red was added in culture medium. The neutral red solution was removed after 4 hours incubation at 37° C. with 1% acetic acid and 50% ethanol solution by volume was added for dye extraction, and dye extraction was shaken for 5 minutes. Absorbance was then measured at 540 nm using a spectrophotometer. The intensity of red color obtained was directly proportional to the viability of the cells and inversely proportional to the toxicity of the material.

Cell proliferation was tested using the mitochondrial metabolic activity assay. Cell layers were first rinsed with PBS. MTT solution was added at 1 mg/mL in PBS containing 1 mg/mL glucose. MTT solution was removed after 4 hours incubation at 37° C. Dimethyl sulfoxide (DMSO) was used to dissolve insoluble formazan crystals, and the absorbance at 540 nm was measured using a spectrophotometer. The intensity of blue color was directly proportional to the metabolic activity of the cell populations and inversely proportional to the toxicity of the material or extract.

(v) Mechanical Testing

Compliance mismatch is one of the most common causes of vascular graft failure, resulting in intimal hyperplasia and occlusion. If the scaffold is too compliant, it may form an aneurysm.

Scaffolds were immersed in a water bath and cannulated at either end. One cannula was connected to a column of water and the other to a drainage tube. The column of water was high enough to create a pressure within the vessel-shaped scaffold of 120 mmHg. Water was drained through the scaffold in order to lower the pressure in increments of 10 mmHg. At each increment, the diameter of the scaffold was recorded using a digital camera. This process was repeated until the pressure was 0 mmHg.

(vi) Axial and Circumferential Segment Testing

Vessels must resist higher stress in the circumferential direction than in the axial direction. Native vessels adapt their mechanics to this loading environment. It is important that the electrospun scaffolds exhibit a mechanical strength at least that of native vessels. Mechanical loading tests were performed on the electrospun vessels in the axial and circumferential directions using a uniaxial load test machine (Instron Corporation, Issaquah, Wash.). A short segment from a tubular scaffold was clamped at its cut ends for the axial test. The crosshead speed was set at 0.5 mm/sec and the test was stopped when the strain decreased by 10% after the onset of failure. For testing in the circumferential direction, a ring of material was cut from the scaffold, opened into a strip and then clamped at either end of the strip. This test was also performed at a rate of 0.5 mm/sec.

(vii) Burst Pressure Testing

The burst pressure for vascular scaffolds was found by monitoring increasing pressures within the vessel until failure occurred. A pressure catheter was inserted through a cannulating fixture at one end of the vessel. A 60 cc pressure syringe was inserted through a custom cannula at the other end of the vessel. The pressure was increased until rupture, failure or leakage occurred and the pressure change was recorded.

(viii) Functionalization of Matrices

Figure 2:
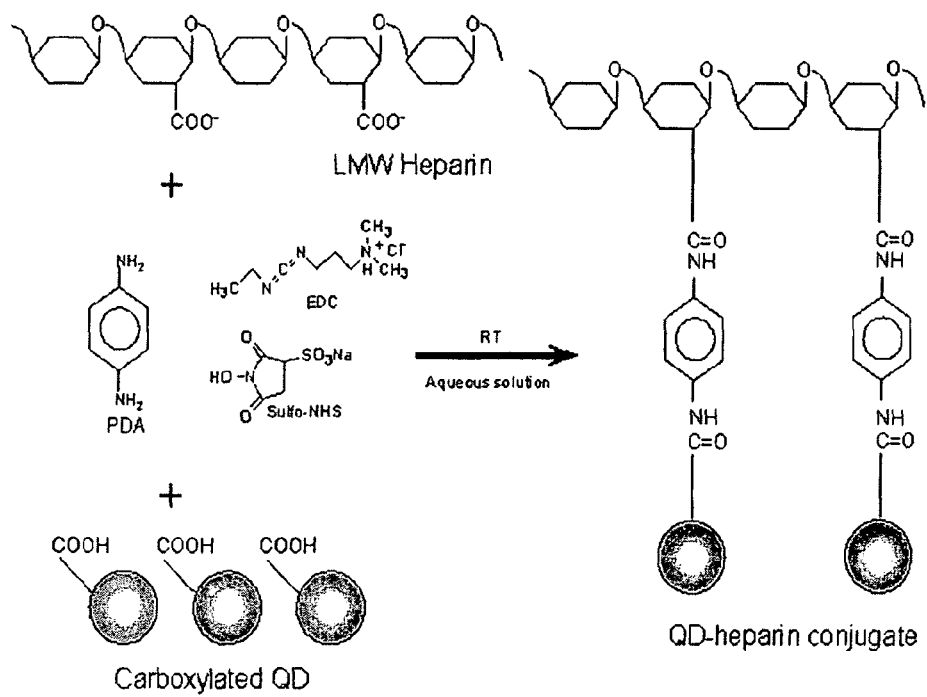
FIG. 2 is a schematic of the conjugation of heparin on quantum dots.

To functionalize a matrix, EDC (10 mg) and sulfo-NHS (2 mg) were added to 5 mL (0.05 mg/mL) of carboxylated quantum dots in aqueous solution under gentle stirring for 1 hr at room temperature. EDC activated heparin (30 mg/20 μl) was prepared according to the same EDC and NHS method. In order to conjugate quantum dots and heparin, 5 mg PDA was added to the activated quantum dots and heparin solutions under stirring for 2 hr at room temperature. The quantum dot-heparin (QD-heparin) conjugation can be quenched by adding an equal volume of 1 M Tris buffer solution (pH 7.4) and stored in 4° C. (FIG. 2).

(ix) Encapsulation

Microencapsulation of QD-heparin was performed by double emersion. Briefly, 4 mL of internal aqueous phase containing 30 mg QD-heparin and 10 mg bovine serum albumin (BSA) as stabilizer was emulsified in 8 ml solution of 100 mg PLGA and 100 mg PCL in dichloromethane. The solution was emulsified by vortexing for 5 minutes at room temperature. This W/O dispersion was diluted to 200 ml of 1% (w/v) aqueous PVA solution under stirring for 4 hr at room temperature. The microcapsules were washed several times with deionized water and then lyophilized overnight.

(x) Heparin Release Using IR Irradiation of the Quantum Dot

In order to evaluate the burst release of heparin, 0.55 mg of PLGA microcapsules containing QD-heparin were suspended in 2 ml of PBS (phosphate buffered saline). The solution was irradiated for 0, 10 and 30 min using an AM1.5 solar simulator at 75 mW/cm2. On days 1, 3 and 5, the samples were then cooled to 4° C., centrifuged at 4500 rpm for 20 min and filtered (0.45 µm pore size) to remove any microcapsules for the optical measurements. Luminescence measurements were performed using an argon ion laser (514.5 nm at 400 mW/cm2) as the excitation source and spectra were collected using a CCD spectrophotometer with an integration time of 40 sec.

(xi) Mouse Model

Mice (C57BL6) will be obtained from Jackson laboratories, Bar Harbor Me. All experimentation in mice will be performed aseptically under general anesthesia (ketamine; 45-75 mg/kg and Xylazine; 10-20 mg/kg, IP). The incision sites are scrubbed with betadine and wiped with alcohol. Analgesia (Buprenorphine 0.05-0.1 mg/kg, SC) is given post-operatively after implantation. Prophylactic antibiotic agents (cefazoline 25 mg/kg, sc) are given to the animals at the time of implantation. The prepared blood vessels (2×0.5 cm) will be implanted in the dorsal subcutaneous space of mice through a minimal longitudinal midline incision with 2 implants per animal. The wound will be closed with interrupted absorbable sutures and the animals will be sacrificed 1, 2, 4, 8, 12, 18 and 24 weeks after implantation for analyses. For the collection of blood samples, mice will be anesthetized and blood will be retrieved into heparin containing tubes using cardiac puncture and the mice will be sacrificed thereafter.

(xii) Sheep Model

A total of 120 sheep will be used. The experimental study will consist of 6 different groups of the blood vessels. Each animal will serve as its own control. Animals will be sacrificed at 1, 3, 6, 12, and 18 months after implantation. Animals will be monitored at 0, 1, 2, 3, and 4 weeks and monthly for grafts implanted greater than one month.

Sheep will be sedated with Ketamine (5 mg/kg, IM), intubated and anesthetized with Isofluorane (1-3%), and placed on a ventilator administering Isoflurane for maintenance. Following Duplex ultrasound imaging of native femoral arteries the groins will be prepped in a sterile fashion and antibiotics administered (cefazolin 25 mg/kg, i.v.). A longitudinal incision will be made overlying the superficial femoral artery, which will then be exposed over a length of 6 to 8 cm. Animals will receive aspirin for 48 hours prior to surgery (80 mg, p.o.) and heparin will be administered immediately prior to implantation (100 U/Kg, i.v.). The femoral artery will then be clamped and divided proximally and an end-to-side anastomosis created between native and engineered artery with running 7-0 Prolene sutures. The distal anastomosis will then be created in a similar fashion and blood flow restored through the implant. Duplex ultrasound will then be repeated using a sterile intraoperative probe cover to establish artery dimensions and blood flow immediately after implantation. Wounds will then be closed with absorbable sutures and the animals recovered from anesthesia using Atropine (0.02 mg/kg i.v.) prior return to standard housing. Post-operative antibiotics will be administered (Cephazoline 25 mg/kg/day) for 3 days following the procedure. Analgesia will be administered (ketoprofen 2 mg/kg) every 6-12 hours for 3 days. Aspirin will also be administered (80 mg daily) for 7 days orally for anticoagulation. The animals will be sacrificed 1, 3, 6, 12 and 18 months after implantation for analyses. At each time point, 6 animals will be euthanized for analysis.

Example 2

Electrospun Matrices

An electrospun matrix was formed using the methods outlined in Example 1. A solution of collagen type I, elastin, and PLGA, were used. The collagen type I, elastin, and PLGA were mixed at a relative concentration by weight of 45% collagen, 40% PLGA, and 15% elastin.

Figure 3:
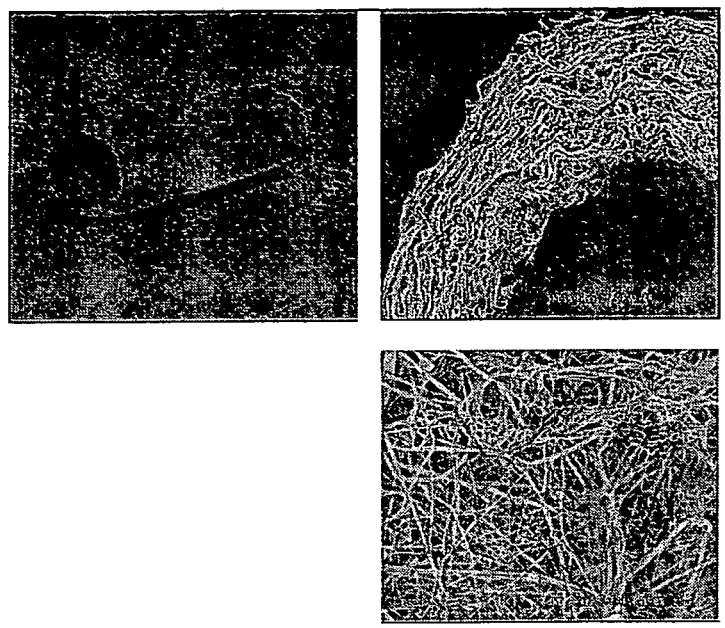
FIG. 3 is an electrospin nanofiber.

The resulting fibrous scaffold had a length of 12 cm with a thickness of 1 mm. A 2 cm representative sample is depicted in FIG. 3. This demonstrates the feasibility of spinning Type I Collagen and elastin into fibers from nanometer to micrometer diameter using concentrations from 3% to 8% by weight in solution. These results also show that by adding PLGA (Mw 110,000) to the mixture, solutions with higher viscosity and improved spinning characteristics could attained. By increasing the solution concentration to 15%, thicker, stronger scaffolds were able to be built while maintaining the collagen and elastin components.

Collagen type I stained positively on the decellularized scaffolds, demonstrating uniform distribution. Elastin distribution within the scaffolds was determined by Movat staining. The electrospun scaffolds with 15% elastin demonstrated a uniform elastin matrix throughout the scaffold wall. These findings indicate that the matrix content and distribution of the electrospun scaffolds can be manipulated to achieve various matrix compositions depending on the need.

Results of biocompatibility assays were calculated as a percentage of negative control and both electrospun scaffolds performed similarly to the decellularized blood vessel. These data suggest that the biocompatibility of electrospun scaffolds is similar to that of decellularized scaffold.

Figure 4:
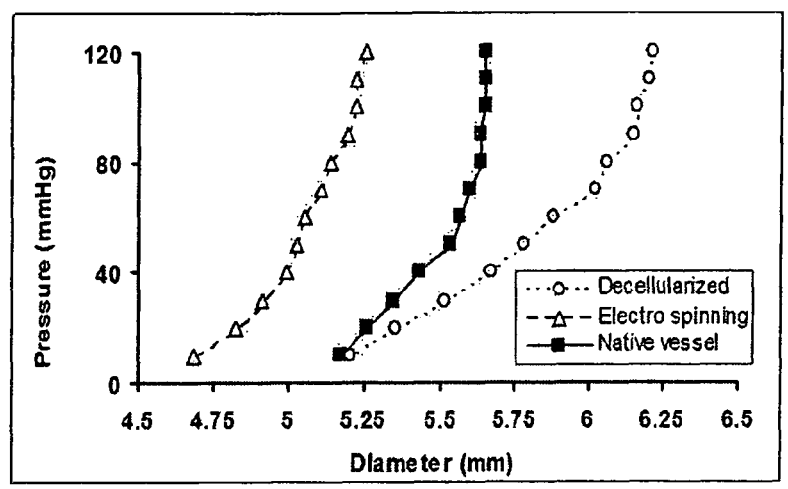
FIG. 4 is graph of pressure-diameter curves of vascular graft scaffolds.

Results of mechanical testing for compliance show a typical pressure-diameter curve for native vessels, as well as for decellularized and electrospun scaffolds. The diameter change was approximately 5% for native vessels and electrospun scaffolds within the physiologic pressure range which is consistent with the in vivo mechanical behavior of porcine and human arteries (FIG. 4). These data demonstrate that the electrospun scaffolds created have a compliance similar to that of a native vessel.

Results of the axial and circumferential mechanical tests from electrospun scaffolds tended to exhibit a more isotropic behavior. Strain in the axial and circumferential directions were nearly equivalent before failure occurred.

The results of burst pressure testing show that the burst pressure for the electrospun construct was 1,425 mmHg or nearly 12 times systolic pressure. These data suggest that electrospun scaffolds have adequate initial strength and elasticity to withstand the mechanical environment when being surgically placed in the circulatory environment.

Histological analysis of the explanted vascular scaffolds from mice showed that there was no evidence of inflammation or tissue encapsulation.

Collectively, these results show that it is possible to control the composition of electrospun scaffolds for use as vascular grafts. Higher concentrations of collagen type I and elastin than previously employed, and mixing with PLGA, result in improved spinning characteristics and strength of grafts, which resist almost 12× systolic pressure. Scaffolds also exhibited compliance characteristics similar to native arteries. Scaffolds had an average fiber diameter of 720 nanometers. EDC crosslinked scaffolds demonstrate superior cell proliferation characteristics to glutaraldehyde crosslinked scaffolds as assessed by mitochondrial metabolic activity assay. Cell viability assays did not demonstrate as pronounced a difference in crosslinking method. These results are some of the first data on biocompatibility of electrospun scaffolds created with biological polymers and PLGA. This work demonstrates the promise of electrospinning as a fabrication process for vascular graft scaffolds.

Example 3

Cross-Linking of Electrospun Matrices

This example demonstrates how to increase the strength and stability of the electrospun scaffold by chemical cross-linking. The scaffolds were soaked in 20% dextran solution in phosphate buffered saline prior to crosslinking to reduce hydration-induced swelling and contraction of the scaffold. The scaffolds were crosslinked by immersion in EDC/NHS in MES/EtOH solution for 2 hours at room temperature. Scanning electron micrographs of the resulting fibers showed fiber diameters of 500 nm or less and a random orientation of fibers. Atomic force microscopy of the scaffold and a confocal image of nanofibers with an adhering endothelial cell demonstrate the scaffold structure. These data show that it is possible to fabricate vascular scaffolds from biological polymers with mechanics and structure similar to decellularized scaffolds and native arteries.

Example 4

Distribution of Collagen and Elastin Content

The relative quantity and distribution of collagen and elastin in a vascular scaffold is important to the mechanical properties and function of the seeded graft. The scaffold composition was assessed using histochemical analysis for collagen types I, II, and III, elastin and hematoxylin, and eosin (H&E) staining was also performed.

The levels of collagen type I, II, and III, and elastin for decellularized matrices and collagen type I and elastin for electrospun matrices were analyzed using computerized histomorphometric analysis. NIH Image/J Image analysis software (National Institutes of Health, Bethesda, Md.) was used for the analysis.

Immunohistochemical analyses using antibodies specific to collagen types I, II and III were performed on the decellularized and electrospun scaffolds. The decellularized scaffolds showed similar collagen type I and III in the vascular media, which corresponds to normal blood vessels. In this study, 45% collagen type I was used to demonstrate the controllability of the scaffold fabrication. Collagen type I stained positively on the decellularized scaffolds, however, collagen type III stained negatively. Elastin distribution within the scaffolds was determined by Movat staining. Abundant elastin fibers were observed in the entire decellularized scaffold wall with a prominent distribution in the serosal and luminal surface. The electrospun scaffolds with 15% elastin demonstrated a uniform elastin matrix throughout the scaffold wall. These findings indicate that decellularized vascular scaffolds possess matrices similar to normal vessels and that the matrix content and distribution of the electrospun scaffolds can be manipulated to achieve various matrix compositions depending on the need.

Histograms of the distribution of color were used to determine relative amounts of each component from each stain against negative controls. All values were normalized by area for comparison. Amounts of collagen I, elastin, and PLGA were known for electrospun matrices because of fabrication parameters. Calibrating the image data for relative amounts of collagen utilized both the normalized areas with negative controls, and was calibrated based on known composition of electrospun matrices.

The results demonstrate the composition of collagen I, II, and III, and elastin, in the decellularized scaffolds as well as component percentages in electrospun matrices. These studies show that the collagen and elastin content of decellularized and electrospun scaffolds is similar to that of native vessels.

Example 5

Compliance Testing of Scaffolds

Compliance mismatch is one of the most common causes of vascular graft failure, resulting in intimal hyperplasia and occlusion. If the scaffold is too compliant, it may form an aneurysm. This example describes how to test for compliance of the scaffolds. Decellularized and electrospun vessel shaped scaffolds were immersed in a water bath and cannulated at either end. One cannula was connected to a column of water and the other to a drainage tube. The column of water was high enough to create a pressure within the vesselshaped scaffold of 120 mmHg. Water was drained through the scaffold in order to lower the pressure in increments of 10 mmHg. At each increment, the diameter of the scaffold was recorded using a digital camera. This process was repeated until the pressure was 0 mmHg. Results show the typical pressure-diameter curve for native vessels, and the experimental curves for decellularized and electrospun scaffolds. The diameter change was approximately 5% for native and electrospun and 15% for decellularized scaffolds within the physiologic pressure range which is consistent with the in vivo mechanical behavior of porcine and human arteries. Thus, both decellularized and electrospun scaffolds have a compliance similar to that of a native vessel.

Example 6

Circumferential and Axial Loading of Decellularized and Electrospun Vessels

Vessels must resist higher stress in the circumferential direction than in the axial direction. Native vessels adapt their mechanics to this loading environment. It is important that the decellularized and electrospun scaffolds exhibit a mechanical behavior similar to native vessels. Thus, mechanical loading tests were performed on the decellularized vessels and electrospun vessels in the axial and circumferential directions using a uniaxial load test machine (Instron Corporation, Issaquah, Wash.). An entire vessel-shaped scaffold was clamped at its cut ends for the axial test. The crosshead speed was set at 0.5 mm/sec and the test was stopped when the strain decreased by 10% after the onset of failure. For testing in the circumferential direction, a ring of material was cut from the scaffold, opened into a strip and then clamped at either end of the strip. This test was also performed at a rate of 0.5 mm/sec.

Results of the axial and circumferential mechanical tests from electrospun scaffolds are shown in FIGS. 5A and 5B, respectively.

The electrospun scaffolds tended to exhibit a more isotropic behavior. Strain in the axial and circumferential directions were nearly equivalent before failure occurred. In general, the decellularized construct exhibits the orthotropic mechanical behavior that is expected from the known mechanical behavior of arteries. In particular, strain in the circumferential direction is lower than strain in the axial direction. This was true for scaffolds prior to and after implantation.

The burst pressure for vascular scaffolds was found by monitoring increasing pressures within the vessel until failure occurred. A pressure catheter was inserted through a cannulating fixture at one end of the vessel. A 60 cc pressure syringe was inserted through a custom cannula at the other end of the vessel. The pressure was increased until failure or leakage occurred and the pressure change was recorded. The results show that the burst pressure for the decellularized construct was 1,960 mm Hg or approximately 16 times systolic pressure. The burst pressure for the electrospun construct was 1,425 mm Hg or nearly 12 times systolic pressure. We demonstrated that both electrospun and decellularized scaffolds had adequate strength and elasticity and may be substitutes for native vessels.

Example 7

Isolation, Characterization and Vessel Seeding of Sheep Progenitor EPC and MPC

Progenitor EPC and progenitor muscle cells (MPC) were isolated from 60 ml peripheral blood of the internal jugular vein of sheep. The Lleukocyte fraction was obtained by centrifuging on a Histopaque density gradient. Some of the cells were resuspended in medium and plated on fibronectin coated plates. At 24 hr intervals the floating cells were transferred to new fibronectin coated plates. EPC were induced by growth in EGM-2 medium that contained VEGF and bFGF. The rest of the cells were cultured in the presence of 10 μM 5-Azacytidin for 24 hours. Thereafter floating cells were transferred to a new fibronectin coated plate and cultured in myogenic medium (DMEM low glucose containing 20% fetal bovine serum, 10% Horse Serum, 1% Chick Embryo extract and 1% antibiotics) in order to induce MPC. EPC and MPC were cultured for 4-6 weeks in order to assume differentiated morphology. Immunohistochemical analysis of EPC showed that most of the cells expressed VE cadherin and CD31 but not Desmin. However, MPC showed expression of Vimentin and Desmin but not of VE cadherin. The expression of these markers was maintained during culture in vitro. These results indicate that cultured EPC and MPC possess EC and muscle cell phenotype, respectively.

EPC were labeled by PKH 26 green fluorescent dye and MPC were labeled by PKH 27 red fluorescent dye. Labeled EPC and MPC were seeded on the luminal and the outer surfaces of decellularized vessel segments, respectively, in order to demonstrate the biocompatibility of the decellularized vessel. After 7 days the presence of red and green labeled cells on the decellularized vessel was noted. In addition, seeded vessels were seeded with a suspension of red-labeled MPC and green labeled-EPC ($5 \times 10^6$ cells/ml) and cells were allowed to grow for 7 days. The vessels were embedded in OCT media in order to obtain frozen sections. The sections were stained with DAPI. To detect cell nuclei, sections were visualized using a fluorescent microscope. Data shows that EPC were maintained on the luminal side of the scaffold and MPC on the serosal surface.

Example 8

Cell Attachment

A confluent monolayer of endothelial cells is the most important barrier against thrombosis formation. Endothelial cell mediated NO production is important in maintaining the vascular tone. To examine cell attachment, the decellularized and electrospun vessels were seeded with endothelial cells. Cell attachment was assessed using scanning electron microscopy of scaffolds seeded with a mouse endothelial cell line (MS1). SEM micrographs reveal a confluent monolayer on the inner surface of both the decellularized and electrospun vessels at 48 hours. These results indicate that endothelial cells form confluent monolayers on decellularized and electrospun scaffolds.

Example 9

Biocompatibility (Cell Viability and Proliferation)

Long-term viability of cells is necessary for the seeded scaffold to remodel itself into a viable, patent vessel. To test for cell viability, decellularized and electrospun constructs were placed in 24-well plates with approximately 100 mg of material per well. Four different types of material were tested for biocompatibility and cell survival, with one negative control well with no material: (1) GA-NFS (1% glutaraldehyde crosslinked electrospun scaffold); (2) EDC-NFS (EDC-crosslinked electrospun scaffold); (3) nBV (natural blood vessel, decellularized); (4) Latex (latex rubber, positive control).

Endothelial cells were seeded in the wells on a scaffold for testing via the direct contact method. For cell viability, cell layers were rinsed with PBS. 0.005% w/v neutral red was added in culture medium. The neutral red solution was removed after 4 hours incubation at 37° C. with 1% acetic acid and 50% ethanol solution by volume was added for dye extraction, and dye extraction was shaken for 5 minutes. Absorbance was then measured at 540 nm using a spectrophotometer. The intensity of red color obtained was directly proportional to the viability of the cells and inversely proportional to the toxicity of the material. Results were reported as a percentage of negative control, and both electrospun scaffolds performed similarly to the decellularized blood vessel (FIG. 6A).

Cell proliferation was tested using the mitochondrial metabolic activity assay. Cell layers were first rinsed with PBS. MTT solution was added at 1 mg/mL in PBS containing 1 mg/mL glucose. MTT solution was removed after 4 hours incubation at 37° C. Dimethyl sulfoxide (DMSO) was used to dissolve insoluble formazan crystals, and the absorbance at 540 spectrophotometer. The intensity of blue color was directly proportional to the metabolic activity of the cell populations and inversely proportional to the toxicity of the material or extract. The gluataraldehyde treated matrices show more pronounced differences than in proliferation assays, with EDC treated scaffolds being similar to natural blood vessels (FIG. 6B).

Figure 7A:
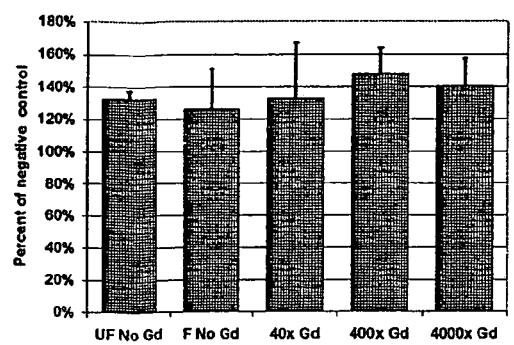
FIG. 7A is a graph of cell viability of endothelial cells cultured on five matrices.
Figure 7B:
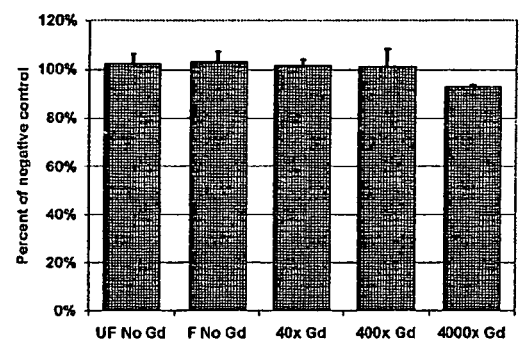
FIG. 7B is a graph of mitochondrial metabolic activity of endothelial cells cultured on five matrices.

Cell viability and proliferation testing was also performed to determine the effects of various concentrations of gadolinium (Gd) on the scaffolds, on cell survival (FIG. 7). The tests revealed little effect of Gd levels on cell viability or survival. The results indicate that both scaffolds can promote cell growth and thus may be used for the bioengineering of vascular grafts.

Example 10

External Functionalization of Matrices

This example describes how to generate matrices with image enhancing agents and quantum dots. In particular, Gd-DPTA and quantum dot functionalization of an external scaffold. The scaffold can be any biocompatible substrate, such as a synthetic PGA matrix, an electrospun matrix, or a decellularized matrix. At present, no clinically available vascular graft allows for noninvasive monitoring of the integration of the graft in vivo, nor does any graft incorporate anticoagulants into its structure. A reliable method is needed to attach nanomaterials to scaffolds, e.g., vascular scaffolds, in order to increase functionality, in particular as a material marker and for anticoagulation. Carboxylated Gd and quantum dot (QD) materials were coupled to the surface of both the decellularized and the electrospun scaffolds using an EDC/sulfo-NHS method. Any unreacted material was quenched and removed by rinsing the scaffold with 0.1 M Tris buffer. The liquid from the final washing was colorless under UV elimination.

Under blacklight illumination the functionalized scaffold shows multicolor fluorescence. Areas of red-orange emission are from the quantum dots. The pale white color, which is stronger in intensity than the control tissue, comes from the Gd containing material that can fluoresce with a pale blue color. The data shows that it is possible to incorporate heparin onto the surface of a scaffold. The scaffolds are also able to bind Gd.

Example 11

Internal Functionalization of Matrices

This example describes the production of electrospun matrices with image enhancing agents and therapeutic agents. In particular, Gd-DPTA and QD addition to the internal electrospun scaffolds. Fabricating vascular scaffolds using electrospinning provides an opportunity to incorporate image enhancing agents within the bulk material. Solutions were spun successfully containing gadolinium diethylenetriamine pentacetic acid (Gd-DPTA) in HFP at a concentration of 15 mg/mL and with quantum dots added at a concentration of 8% by volume from a quantum dot solution of 25.5 nmol/mL in toluene. No morphological change was noted in the scaffolds due to the addition of the Gd-DPTA or the QDs. These results show that incorporating nanoparticles into the scaffolds has only a minimal effect on the morphology of the resulting structure.

Example 12

Matrices with Quantum Dots

This example describes how to couple therapeutic agents, such as heparin to the quantum dots (QD). Heparin is a potent anticoagulant agent. To avoid systemic administration, a method is needed to control the release of heparin from the vascular scaffold and to bind the heparin to the scaffold. In this experiment, EDC (10 mg) and sulfo-NHS (2 mg) was added into the 5 mL (0.05 mg/mL) of carboxylated quantum dots in aqueous solution under gentle stirring for 1 hr at room temperature. EDC activated heparin (30 mg) was prepared according to the same EDC and NHS method as described above. In order to conjugate quantum dots and heparin, 5 mg phenylene diamine (PDA) was added to the activated quantum dots and heparin solutions while stirring for 2 hr at room temperature. The quantum dot-heparin (QD-heparin) conjugation can be quenched by adding an equal volume of 1 M Tris buffer solution (pH 7.4) and stored in 4° C.

Microencapsulation of QD-heparin was performed by double emersion. Briefly, 4 mL of internal aqueous phase containing 30 mg QD-heparin conjugation and 10 mg bovine serum albumin emulsified in 8 mL of a solution of 100 mg PLGA (MW; 110,000) and 100 mg PCL (MW; 110,000) in DCM. The solution was emulsified by vortexing for 5 min at room temperature. This W/O dispersion was diluted into 200 mL of 1% (w/v) aqueous PVA solution under stirring for 4 hr at room temperature. The microcapsules (MCs) were washed several times with deionized water and then lyophilized overnight. QD-heparin nanocapsules (NC) were incorporated into scaffolds by placing the functionalized vascular scaffold in 1 wt % PLL in PBS. Vascular scaffolds were immersed in the PLL-nanocapsule solution for 3-4 hours, and lyophilized before sterilization with gamma irradiation.

A fluorescence image of an isolated microcapsule containing quantum dots shows that the characteristic fluorescence from the quantum dots used in this experiment is at 500 nm. The data show that it is possible to bind heparin to quantum dots and encapsulate the bound heparin in a biodegradable polymer, for attachment to the vascular scaffold.

Example 13

Release Kinetics of Heparin: In Vitro Release of Heparin and Burst Release by Irradiation To assess the effectiveness of quantum dots for controlled delivery of heparin, the release kinetics of the drug was analyzed following an irradiation burst. In order to evaluate the burst release of heparin, 0.55 mg of PLGA microcapsules with QD-heparin were suspended in 2 ml of buffered saline solution. The solutions were irradiated for 0.0, 10, and 30 min using an AM1.5 solar simulator at 75 mW/cm$^2$. On days 1, 3, and 5 the samples were then cooled to 4° C. and centrifuged at 4500 rpm for 20 min. The solutions were filtered (0.45 m pore size) to remove any microcapsules for the optical measurements.

Luminescence measurements were performed using an argon ion laser (514.5 nm at 400 mW/cm$^2$) as the excitation source and spectra were collected using a CCD spectrophotometer with an integration time of 40 sec. Irradiated samples showed increased luminescence over time indicating a "burst effect". The kinetic profile of heparin confirms that irradiation induced the burst release out of functionalized microcapsules. Heparin release was monitored by optical analysis (FIG. 8A) and biochemical analysis (FIG. 8B). These results indicate that NIR can be used to initiate the release of heparin from the QD-heparin microcapsules.

Normally, heparin is administered at the site of implantation immediately following surgery to prevent acute thrombosis. Afterwards, heparin is administrated within the first week twice a day by injection. In order to improve the patient's compliance, heparin could be immobilized in vascular scaffolds for extended period of time. However, the immobilization of heparin to the scaffolds results in a slow release of heparin which is not appropriate for thrombus prevention. To accelerate the burst release of heparin, near infrared (NIR) irradiation of the quantum dots bound to heparin can to be used to achieve this goal.

Example 14

Determination of the Remaining Heparin in Retrieved Vessel Implants from Mice

Figure 9:
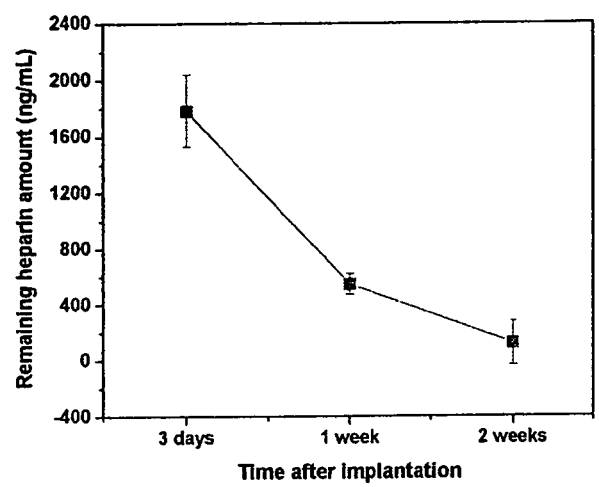
FIG. 9 is a graph showing the quantification of remaining heparin from retrieved vascular scaffolds.

To assess the effectiveness of heparin in an in vivo model, heparin must be evaluated after the explantation of the scaffold. The remaining heparin in functionalized blood vessels (heparin-QD) implanted in mice was determined by toluidine blue staining and most of the heparin is shown to have diffused out of the vessel two weeks after implantation. The heparin content was analyzed by a Rotachrome kit and the data confirms that very little heparin remains after two weeks. The data show that the activity of heparin was successfully prolonged in the scaffold beyond its normal 1-2 hour half-life (FIG. 9).

The inflammatory response of quantum dots should be addressed for clinical applications. From the histological analysis of the explanted vascular scaffolds from mice, there was no evidence of inflammation or tissue encapsulation. The data indicate that conjugated heparin had only a minimal inflammatory response.

Example 15

Evaluation of the Anti-Thrombogenic Properties of Heparin Immobilized Vessels

Although heparin is a powerful anticoagulant, it was important to verify that this property still exists after immobilization. Two methods of heparin binding were tested. Thirty milligrams of heparin was incubated in 20 mM EDC and 10 mM sulfo-NHS in PBS for 2 hours at room temperature, and a 3 mm diameter decellularized scaffold was then immersed in heparin-EDC solution for 2 hours at room temperature. After cross-linking, the sample was rinsed in PBS several times to completely remove residual EDC. Subsequently immobilization of heparin by physical adsorption was performed using Poly(L-lysine) (PLL): The 3 mm diameter decellularized scaffold was incubated in 2 mg/mL PLL solution for 2 hours at room temperature. The PLL-adsorbed scaffold was immersed in 15 mg/mL heparin solution for 1 hour at room temperature. The anti-thrombogenic property of each method was evaluated using whole blood from sheep by toluidine blue staining. Immediate coagulation was observed from the decellularized scaffold while no significant sign of coagulation was found from both EDC and PLL reacted decellularized scaffolds 36 hours after blood treatment. The heparin-PLL decellularized scaffold demonstrated the weakest staining which indicated the highest loading of heparin in the scaffold. These results showed that immobilized heparin was effective in preventing thrombus.

Example 16

Enhanced MRI Imaging

This example demonstrates the improved imaging observed with gadolinium. In vitro experiments were conducted on cell scaffolds with gadolinium to determine the improvement in magnetic resonance imaging. Cylindrical cell scaffolds 20 millimeters long with an internal radius of 10 millimeters and a outer radius of 14 millimeters were created with different Gd loading concentrations. Cell scaffolds were individually placed in test tubes and submerged in PBS. The four test tubes were arranged left to right in the following order: non-functionalized cell scaffold (control 1), functionalized scaffold (control 2), 1× Gd concentration cell scaffold, 100× Gd concentration (control 3) and a 1000× Gd concentration cell scaffold. (100× designates a concentration in solution during functionalization of 55 mg/kg of Gd-DPTA) Axial T1 weighted spin echo images were acquired on a on a GE Healthcare Technologies magnetic resonance imaging (MRI) 1.5T TwinSpeed scanner.

The T1 weighted image acquired with a phased array coil and a 200 millisecond repetition time (TR) was obtained. Additional imaging parameters are as follows: echo time (TE)=13 ms, slice thickness=0.8 mm, 256×128, field of view (FOV)=12 cm×6 cm, number of averages=100, and phase direction was right to left. The cell scaffolding loaded with 1000× Gd (right most test tube) is clearly visible compared to controls 1, 2, and 3. Samples were washed twice with TRIS buffer and PBS and stored in PBS for 2 weeks prior to imaging.

The previously described experiment was repeated for two different Gd loaded scaffold preparations: surface and volume loading. The scaffold on the left is a cylindrically shaped scaffold identical to the previously described experiment with a surface loaded 1000× Gd preparation. The scaffold on the right is a planar sheet of scaffold with the Gd embedded throughout the electrospun fibers as described previously. The scaffold that had the Gd electrospun into the fiber showed a much higher contrast. The normalized signal intensities of the scaffold for the surface preparation and volume preparation are 1.5±0.2 and 2.98±0.35, respectively. The data on MRI Imaging of Gd loaded scaffolds showed that Gd increases MRI contrast in proportion to the level of Gd loaded in the scaffold.

Example 17

In Vivo Preliminary Data on Rodents

Although Gd may be maintained in the scaffolds in vitro, it is necessary to demonstrate that it retains functionality in vivo. This experiment investigates the in vivo functionality of the scaffolds. Electrospun vascular scaffolds were implanted subcutaneously in a mouse for two weeks prior to imaging. Gd was added to one of the vascular scaffolds to enhance its contrast on a T1 weighted image. A sagittal localizer image was acquired from the mouse and a T1 weighted coronal image containing the two scaffolds was prescribed off the sagittal image. The important imaging parameters of the T1 weighted image are repetition time (TR) 300 milliseconds, echo time (TE) 14 milliseconds, and slice thickness 2 millimeters. A 50% improvement in image contrast of the Gd scaffold compared to the control. These results in a rodent model demonstrate that the characteristics seen in vitro are maintained in vivo.

Example 18

Ex Vivo Preliminary Data on Sheep Engineered Vessels

In vivo results in the rodent model were limited to subcutaneous specimens. It was necessary to demonstrate similar results in a scaffold exposed to blood flow in a large animal model. To determine the feasibility of using the cell seeded scaffolds containing the nanoparticles (heparin conjugated with quantum dots and Gd-DTPA), femoral artery bypass procedures were performed in sheep. Peripheral blood samples were collected, circulating progenitor cells were selected and differentiated into endothelial and smooth muscle cells in culture. Each cell type was grown, expanded separately and seeded on decellularized vascular scaffolds containing the nanoparticles (30 mm long). Nanoparticle containing scaffolds without cells served as a control. Under general anesthesia, sheep femoral arteries were imaged with duplex ultrasonography (B-mode ultrasound and Doppler spectral analysis) with a high resolution 15 MHz probe (HDI-5000, ATL) prior to scaffold implantation. The femoral artery was exposed through a longitudinal incision over a length of 6 to 8 cm. Aspirin and heparin were used as anticoagulation and the femoral artery was clamped and divided proximally. An end-to-side anastomosis was created between native and engineered artery. The distal anastomosis was created in a similar fashion and blood flow restored through the implant followed by ligation of native femoral artery between the two anastomoses. Doppler ultrasonography was performed using a sterile probe to establish scaffold dimensions and blood flow after implantation. Wounds were closed and the animals recovered from anesthesia prior to 3500 return to standard housing. Aspirin was administered routinely for 7 days orally for anticoagulation.

Duplex ultrasound imaging was performed to determine the presence of thrombosis, lumen narrowing intimal hyperplasia and graft wall stricture, and graft aneurismal degeneration. Longitudinal and cross-sectional images of the pre- and post operative arterial segments showed a patent lumen 0 with similar peak systolic, end-diastolic and time averaged velocities as the normal artery. The arterial wall thickness and luminal diameter of the engineered bypass was similar to native artery. The engineered arterial bypass and the contralateral normal femoral artery were scanned with MRI. T1 weighted spin echo MR images were acquired with the following parameters: 256×126 matrix, 12×6 mm FOV, 400 ms TR, 13 ms TE, 1 mm slice thickness, and 50 excitations. Average signal intensities of the samples were normalized by the background water intensity to account for receiver coil nonuniformities. The normalized intensities were 2.62 and 2.10 for the scaffold and normal vessel, respectively.

This experiment was repeated at several different TRs and the signal intensity measured for the scaffold and the normal vessels. As expected, the signal intensity for the gadolinium enhanced scaffold is always greater than the normal vessel. These results confirmed that Gd and heparin loaded decellularized scaffolds maintain patency in a sheep model and maintain MRI contrast.

Gadolinium is a MR contrast agent that enhances images primarily by decreasing the spin-lattice relaxation time (T1) of protons in tissues. Unlike radionuclides, it will remain effective as long as it is localized in the engineered vessel. These results shown in vitro through repeated rinsing of the Gd doped scaffolds and in vivo through imaging of the engineered vessel, that the functionalized Gd nanoparticles are stable in the matrix. Within the first 3 months, approximately 80% of the graft will be remodeled. The Gd localized in the matrix will initially enhance the imaging of the graft. The change in MR signal over time, as the concentration of Gd decreases with remodeling of the vascular graft, will allow us to quantify the remodeling rates.

Example 19

Histomorphological Characteristics of Bypass Grafts in Sheep

To demonstrate cell attachment on the retrieved engineered vessels initially seeded with endothelial and muscle cells, scanning electron microscopy was performed 2 weeks after implantation. The implanted decellularized scaffolds seeded with cells showed a uniform cell attachment on the luminal surface of the engineered artery similar to normal vessels. The scaffolds without cells failed to exhibit cell attachment. These observations indicate that the cells seeded on decellularized vascular scaffolds are able to survive and remain attached after surgery.

To assess the histo-morphological characteristics of the retrieved tissue from engineered arterial bypass grafts in sheep, histological evaluation was performed. The engineered arterial specimens were fixed, processed and stained with hematoxylin and eosin (H&E) and Movat staining. The cell seeded engineered grafts contained uniform cellularity throughout the vascular walls. Abundant elastin fibers were observed in the entire arterial wall with a prominent distribution in the serosa and luminal surface. These findings demonstrate that the engineered vessels, seeded with peripheral blood derived progenitor cells differentiated into endothelial and smooth muscle cells, are able to show an adequate cellular architecture similar to native vessels.

Collectively, these studies show that it is possible to fabricate and functionalize both decellularized and electrospun scaffolds with cells (endothelial and smooth muscle) and nanomaterials (quantum dot—conjugated heparin) that are known to have a positive therapeutic benefit. Moreover, the data shows the successful incorporation of molecules (gadolinium) enhancing MRI contrast to monitor the engineered vessels over time. The combination of functionalization and imaging offers the potential for making these scaffolds an ideal vascular substitute. The matrices are biocompatible, possess the ideal physical and structural properties, and have been shown to be functional for over 4 months in the carotid artery of sheep.

Example 20

To Characterize the Engineered Vascular Grafts

In order for a vessel to function normally, it should have the appropriate structural properties to accommodate intermittent volume changes. In pathologic conditions, normal vessel function and mechanical properties may be compromised. To translate the use of bioengineered vessels to patients, it is first necessary to confirm that normal vessels are being formed, and that they retain adequate phenotypic and functional characteristics over time, especially with growth.

(i) Mechanical Testing

Understanding the mechanical properties of explanted vessels provides information about the adaptive remodeling those vessels have undergone while in the host animal. Mechanical testing will include arterial elongation (axial and circumferential), compliance, burst pressure, stress relaxation, and creep.

(ii) Phenotypic and Composition Analyses

Histological and immunohistochemical analysis can be performed on the retrieved vascular grafts. Longitudinal and cross sections will be taken from the transition zones between native vessels and graft and from the rest of the graft. Specimens will be fixed, processed and stained with Hematoxylin and eosin (H&E) and Masson's trichrome. Cross-sectional areas of the adventitia, media, intima and lumen will be measured using computer-assisted analysis of digital images (NIH Image Software). In addition to cross-sectional analysis of the engineered artery body, a separate analysis will be performed for the anastomoses region between native and engineered arteries. The proximal and distal anastomoses will be fixed in formalin, embedded in paraffin, and then cut in cross-section for analysis of lumen caliber and artery wall thickening in step-sections spanning each anastomosis. In parallel, quantitation of thrombus formation will be performed using H&E staining. The phenotypic characteristics of the retrieved tissues will be determined over time.

To determine the degree of endothelial and smooth muscle content of the bioengineered vessels over time, in comparison to normal tissues, multiple molecular markers will be probed immunocytochemically and with Western blot analyses, as described above. These markers will include Anti-Desmin and Anti-Alpha Smooth Muscle Actin, which specifically detects smooth muscle cells. Endothelialization will be evaluated by anti-von-Willebrand factor anti-CD-31 and anti-VEGF receptor, KDR, antibodies, which stain EC specifically. Cell proliferation and apoptosis in engineered arteries will be determined by BrdU incorporation and TUNEL staining.

The composition and distribution of extracellular matrix components, such as collagen and elastin, are important for the normal function of blood vessels. While the collagen network is responsible for tensile strength, elastin is important for the elastic recovery of the vessel. Therefore, an assessment of the collagen and elastin content and distribution of the retrieved tissues over time will be performed with histological and quantitative biochemical assays. To determine whether the retrieved vessels possess normal concentrations of collagen and elastin, as compared to normal controls, the total collagen and elastin content per unit wet weight of the retrieved tissue samples will be measured quantitatively using the Sircol collagen and the Fastin elastin assay systems (Accurate Chemical & Scientific Corporation, Westbury, N.Y.). To determine the anatomical distribution of collagen within the engineered vessels, as compared to controls, Immunocytochemical localization of collagen types I, II and III will be performed using specific monoclonal antibodies (Southern Biotechnology Associates, Inc., Birmingham, Ala.) and with the elastin-specific stain, Movat.

(iii). Physiological Analysis

The ability to synthesize vasoactive agents such as Nitric Oxide (NO) will further determine the functionality of the engineered vascular scaffolds. There is increasing evidence on the importance of NO in vascular hemostasis. NO contributes to resting vascular tone, impairs platelet activation, and prevents leukocyte adhesion to the endothelium.

Briefly, guinea pig thoracic aorta will be harvested, the endothelium layer removed by gentle rubbing and cut into 5-mm segments. Each segment will be suspended between 2 tungsten stirrups for measurement of isometric tension. The vessel segments placed in an organ chamber with 10 ml Kreb's buffer solution at 37° C. with a mixture of 5% $CO_2$, 15% $O_2$ and a balance of N2. Each vessel (2-3 cm in length) is tied to a 21 G needle, which was attached to plastic IV tubing and placed above the organ chamber with the fresh aortic segment. The segments will be contracted with 80 mM KCl Kreb's buffer in a stepwise fashion to obtain a resting tension of 4 g. After resting for 90 minutes, the segments are contracted in response to prostaglandin F2α up to a final concentration of 10-7M and until a stable contraction of approximately 50% of maximum KCl-induced contraction achieved. Vasoactive agents and antagonists are then added using an infusion pump through the vessels to induce NO production. Doses of the vasoactive agents between 10-7-$10^{-3}$ M will be tested and dose-response curves will be constructed.

Example 21

Preparation of Decellularized Tissues and Organs

The following method describes a process for removing the entire cellular content of an organ or tissue without destroying the complex three-dimensional infra-structure of the organ or tissue.

(i) Organs

A liver was surgically removed from a C7 black mouse using standard techniques for tissue removal. The liver was placed in a flask containing a suitable volume of distilled water to cover the isolated liver. A magnetic stir plate and magnetic stirrer were used to rotate the isolated liver in the distilled water at a suitable speed for 24-48 hours at 4° C. This process removes the cellular debris and cell membrane surrounding the isolated liver.

After this first removal step, the distilled water was replaced with a 0.05% ammonium hydroxide solution containing 0.5% Triton X-100. The liver was rotated in this solution for 72 hours at 4° C. using a magnetic stir plate and magnetic stirrer. This alkaline solution solubilized the nuclear and cytoplasmic components of the isolated liver. The detergent Triton X-100, was used to remove the nuclear components of the liver, while the ammonium hydroxide solution was used to lyse the cell membrane and cytoplasmic proteins of the isolated liver.

The isolated liver was then washed with distilled water for 24-48 hours at 4° C. using a magnetic stir plate and magnetic stirrer. After this washing step, removal of cellular components from the isolated was confirmed by histological analysis of a small piece of the liver. If necessary, the isolated kidney was again treated with the ammonium hydroxide solution containing Triton X-100 until the entire cellular content of the isolated liver was removed. After removal of the solubilized components, a collagenous three-dimensional framework in the shape of the isolated liver was produced.

This decellularized liver was equilibrated with 1× phosphate buffer solution (PBS) by rotating the decellularized liver overnight at 4° C. using a magnetic stir plate and magnetic stirrer. After equilibration, the decellularized liver was lyophilized overnight under vacuum. The lyophilized liver was sterilized for 72 hours using ethylene oxide gas. After sterilization, the decellularized liver was either used immediately, or stored at 4° C. or at room temperature until required. Stored organs were equilibrated in the tissue culture medium overnight at 4° C. prior to seeding with cultured cells.

(ii) Blood Vessels

Porcine arterial segments were obtained from pigs (20 to 30 Kg, Paterson Farm, Mass.). Blood vessels with an internal luminal size of 3 to 4 mm were cut into segments of approximately 4 cm in length. Vessels were placed in distilled water for one hour to induce red blood cell lysis, thoroughly washed, and incubated in a decellularization solution containing 1% Triton 100X and 0.1% ammonium hydroxide in saline for 48 hours in a mechanical rotating shaker (120 RPM) at 40° C. This process was repeated twice and followed by extensive washes in distilled water. The decellularized vessels were placed in PBS for 24 hours and then lyophilized (Virtis; Gardiner, N.Y.) and sterilized in cold gas.

The results of the decellularization process showed that arterial segments that underwent decellularization and lyophilization maintained their tubular appearance and did not shrink significantly. Hematoxylin and eosin (H&E) staining of decellularized vessels showed layers of collagenous fibers within the vessel walls, suggesting that the decellularization process did not damage the non-cellular components of the native vessel wall.

To examine the composition of the decellularized vessel wall matrix, Movat staining was performed that distinguishes between different extracellular components. The results showed that decellularized vessels preserved their extracellular matrix architecture, including internal and external elastin layers (brown staining) and several collagen layers in the middle (red staining). Scanning electron microscopy (SEM) examination of the luminal side of decellularized vessels showed the removal of the native cell layer, leaving a smooth surface. Cross section of the vessel wall revealed many collagen layers that are denser in the luminal side.

Figure 10:
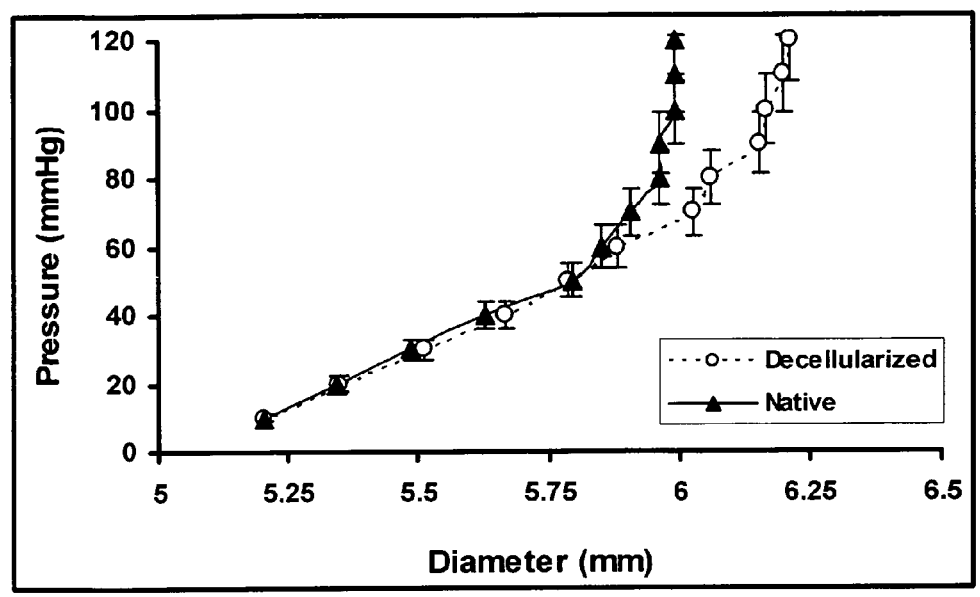
FIG. 10A is a graph showing the pressure-diameter curve of decellularized and native blood vessels.
FIG. 10B is a graph showing the axial and circumferential stress and strain of decellularized and native blood vessels.
Figure 10:
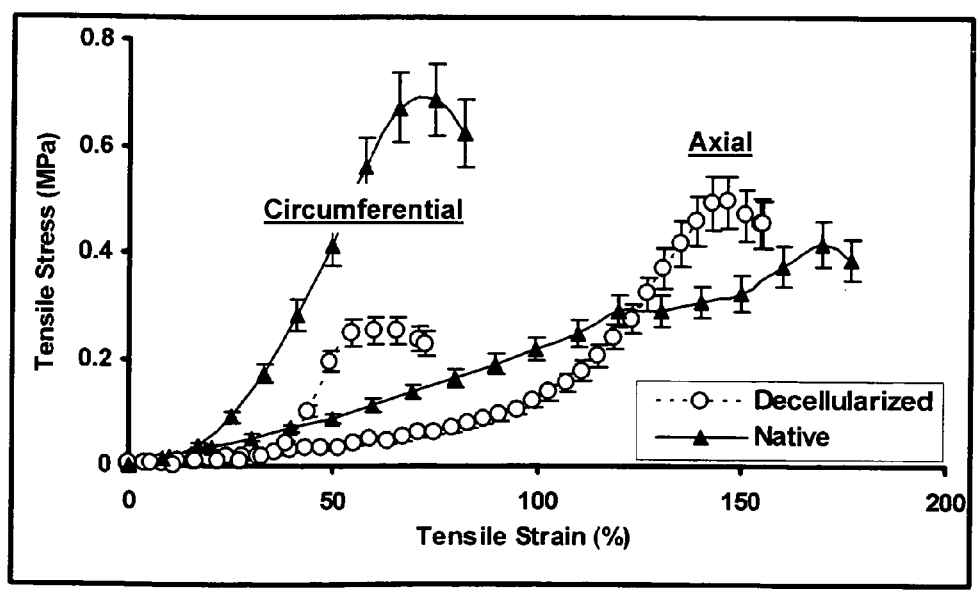

The mechanical behavior of decellularized vessels was also assessed by examining how the decellularized vessels responded to mechanical loading. The results showed the typical pressure-diameter curve for a pure collagen vessel (FIG. 10A). The diameter change ranged from 4-5% for both vessels which is consistent with the in vivo mechanical behavior of large arteries in humans. Mechanical loading tests were performed on the decellularized vessels in the axial and circumferential directions using a uniaxial load test machine. The decellularized vessels exhibited the orthotropic mechanical behavior that is expected from the known mechanical behavior of arteries. In particular, strain in the circumferential direction occurs to a lesser extent than strain in the axial direction (FIG. 10B). The burst pressure for the de-cellularized construct was 1,960 mm Hg or approximately 16 times systolic pressure. Taken together, these results indicate that the decellularization of porcine arterial segments reliably remove cellular components from the vessels while preserving the extracellular matrix within the vessel wall and its mechanical strength.

Example 22

Isolation of Human Saphenous Endothelial Cells (HSVEC)

After obtaining an informed consent, discarded segments of the saphenous vein were obtained from patients undergoing CABG. The vessels were placed in M199 medium containing 20% FCS. Segments of approximately 1 cm were clamped at both ends and filled with 1 mg/ml collagenase type II in serum-free M199 medium and placed in a 5% CO2 humidified incubator for 20 minutes at 37° C. The vein was then flushed with 50 ml of M199 and cells were collected by centrifugation for 10 minutes at 300×g. Subsequently, cells were resuspended in 3 ml EBM-2 medium containing 20% FBS and seeded in 3 cm gelatin-coated dishes. After reaching near confluence, HSVEC were purified by immunoisolation using Ulex europeaus I lectin (UEA-I; Vector, Burlingame, Calif.) coated magnetic beads (Dynal, Norway), as described in Jackson, et al., (1990) *J. Cell Sci.*: 257-262. Subsequently, HSVEC were cultured in gelatin-coated 10 cm plates and the medium was replaced every three days. The cell harvesting and immunoisolation processes were repeated several times with similar results and the cells were cultured for more than 12 passages. For immunohistochemical analyses, HSVEC seeded onto 8 chamber slide were fixed with 2% paraformaldehyde, washed and incubated with primary antibodies. Biotinylated secondary antibodies were used and were detected by FITC-conjugated avidin. The slides were mounted with DAPI-containing media and visualized under fluorescent microscopy. Cultured HSVEC in 10 cm dishes were lyzed in buffer containing 10 mM Tris, pH 7.0, 50 mM NaCl, 1% Triton and protease inhibitors. Immunoprecipitations and Western blots with anti-KDR antibodies.

Example 23

Bioreactor Chamber

To produce blood vessels that have mechanical properties that mimic native in vivo blood vessel, i.e., are able to withstand variations in blood flow and pulse rate, a bioreactor chamber was designed and used to precondition the engineered blood vessels.

The fabrication and enhancement of physical properties of a tissue engineered small-caliber blood vessels (TEBV) is illustrated using decellularized porcine carotid arteries that are coated with human endothelial cells. The cell seeded matrix is placed in bioreactor where they were incubated in physiological flow and pressure conditions for 1 week.

Figure 12:
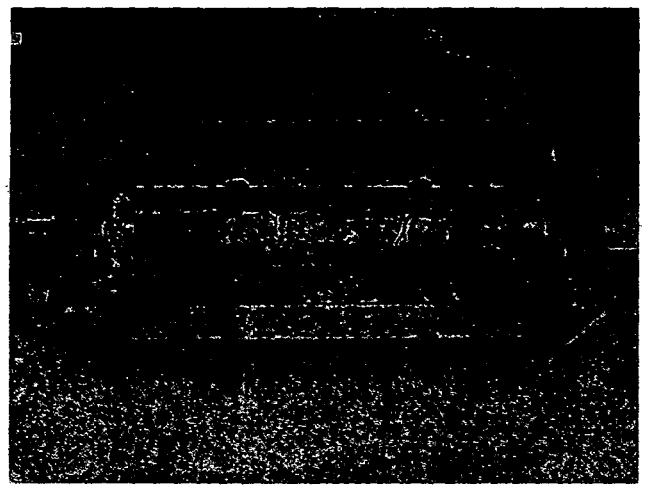
FIG. 12 is a photograph of a preconditioning chamber of the invention.
Figure 13:
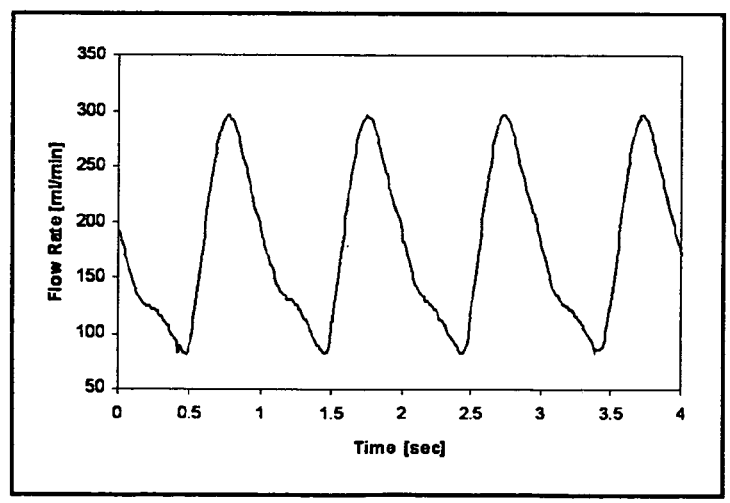
FIG. 13 is a graph showing the flow rate waveform of a pulsatile flow within a preconditioning chamber of the invention.

The method involves attaching the sterile decellularized blood to the bioreactor via luer fittings (FIG. 12). Human endothelial cells at a density of $1.5 \times 10^6$ cells/ml were inserted and sealed into the lumen of the vessel to allow for static seeding. The bioreactor was then rotated 90 degrees every 3 minutes for two revolutions. After rotations, the cells were incubated for an additional 30 minutes statically prior to positioning the bioreactor (vessel) in the flow system to induce shear stress. Steady flow was increased steadily over 4 days to induce wall shear stress values ranging from 3 to 20 dynes/cm$^2$. Pulsatile flow conditions followed for two additional days generating wall shear stress values ranging from 10 to 25 dynes/cm$^2$ and a pressure distribution from 80 to 180 mmHg. Cryostat sections (8 µm) were analyzed histologically with hematoxylin and eosin (H&E) to discern endothelial cells binding.

A functional confluent EC layer is an essential component for the prevention of graft thrombosis and atherosclerosis. Therefore, it is important to have proper seeding of the luminal in the decellularized blood vessel. Using the bioreactor, endothelial cells were found to be provide a uniform confluent layer of endothelium.

The mechanical properties (burst pressure, stress, and strain) of the decellularized vessels were very similar to the native human artery. Hematoxylin and Eosin staining (H&E) illustrated that endothelial cells, seeded on the luminal side, adhered to the matrix and formed a uniform monolayer. These results reveal that, TEBV coated with endothelial cells posses many of the morphologic and functional characteristics of small-caliber vessels. TEBV may potentially be useful clinically as vascular grafts.

Example 24

Seeding Decellularized Porcine Arterial Segments with HSVEC

One of the vessel outlets from the bioreactor of described in Example 23 was sealed and approximately 0.5 ml of HSVEC ($5 \times 10^6$ cells/ml) suspension was inserted into the other outlet and left inside the vessel for an hour with rotations every 15 minutes. Thereafter EBM-2 was gently added and the medium was replaced every 2-3 days. Cells were allowed to grow 5 to 7 days on the matrix. Sixteen HSVEC seeded decellularized porcine vessels were implanted in the subcutaneous space of 8 athymic mice and retrieved for histological analysis after 7 days. The retrieved matrices were immersed in O.C.T. compound (Sakura Finetek; Torrance, Calif.) and frozen in liquid nitrogen. Cryostat sections (5 µm) were analyzed histologically with hematoxylin and eosin (H&E) and by immunostaining with anti CD-31 antibodies. Control staining was performed using normal goat serum. The primary antibodies were detected using the avidin-biotin-immunoperoxidase method. As a control, the primary antibody was replaced with normal goat serum.

Although the decellularized arterial segments maintained an intact tubular structure, allowing them to serve as a short-term conduit, a functional confluent EC layer is an essential component for the prevention of graft thrombosis and atherosclerosis. Accordingly, the clinically relevant source of human EC was examined. EC were isolated from discarded human saphenous vein segments (HSVEC) and purified from the primary culture by immunoisolation, using Ulex europeaus I lectin. HSVEC from several donors were successfully expanded in culture, long term, and they formed a typical EC monolayer at confluence. Immunohistochemical analysis of HSVEC with anti-vonWillebrand factor (vWF) and anti-KDR antibodies showed typical punctuated staining. Anti-CD31 staining showed a specific membranal staining. In contrast, the HSVEC were negative for smooth muscle cell (SMC) actin staining. The expression of an endothelial-specific VEGF receptor 2 (KDR) was confirmed by immunoprecipitation and Western blot with anti-KDR antibodies. The expression of these EC markers was maintained during culture in vitro. These results indicate that cultured HSVEC possess EC phenotype and express specific EC genes and functional growth factor receptors.

HSVEC were seeded on the lumen of decellularized porcine vessels and the cell seeded vessels were incubated in culture for additional 5-7 days. SEM examination of seeded vessels showed surface coverage with a uniform layer of cells. Segments of seeded vessels were further processed for mRNA isolation. RT-PCR analysis of cell-seeded decellularized vessels revealed expression of VEGF receptors, Flt-1, KDR and NRP-1 as well as GAPDH, similar to the expression levels in cultured HSVEC. In contrast, the expression of these genes could not be detected in the unseeded decellularized vessels, confirming a complete decellularization of the arterial segments. These results confirmed the presence of HSVEC on the decellularized vessels in vitro 5-7 days after cell seeding.

The cell seeded decellularized vessel segments were implanted in the subcutaneous space of athymic mice in order to test if HSVEC could be maintained on the decellularized vessel in vivo. Vessel implants were retrieved after 7 days and were processed for histological analysis. H&E staining demonstrated a uniform monolayer of cells on the luminal surface of the decellularized vessels. Immunohistochemical staining with anti-human CD31 confirmed that the cell layer consisted of HSVEC. Taken together, these results indicate that the decellularized vessels are a compatible substrate for EC in vitro and in vivo.

Example 25

Characterization of Blood Vessels

This example described the various techniques used to characterize the seeded blood vessels:
(i) RNA Isolation and RT-PCR
Decellularized porcine vessels, vessels seeded with HSVEC (approximately 4 cm) and, cultured HSVEC were homogenized in RNAzol reagent at 40 C using a tissue homogenizer. RNA was isolated according to the manufacturer's protocol (TelTest, Friendswood, Tex.). Complementary DNA was synthesized from 2 mg RNA using the Superscript II reverse transcriptase and random hexamers as primers. RT-PCR analysis using Flt-1, KDR, neuropilin-1 (NRP-1) and glyceraldehyde phosphate dehydrogenase (GAPDH) primers (Invitrogen, Carlsbad, Calif.) was performed using manufacturers protocols. PCR products corresponding to Flt-1 (416 bp), KDR (479 bp), NRP-1 (409 bp) and GAPDH (673 bp) were resolved on a 2% agarose gel, stained with ethidium-bromide and visualized under U.V. light.
(ii) Synthesis of Prostaglandin F1α
Synthesis of Prostaglandin F1a was determined by measuring 6-keto prostaglandin F1a in conditioned media. Briefly, HSVEC were seeded onto decellularized matrices (approximately 1.5×105 cells/50 mm2). After 48 hours the matrices were transferred into separate wells of a 48-well dish. In parallel, increasing amounts of HSVEC were seeded on 48-well dishes. After 3 days, 50 ml of conditioned media were assayed using the enzyme immunoassay kit according to the manufacture's instructions (Cayman Chemical; Cayman Islands). The levels were calculated as the production of 6-keto prostaglandin F1a during 3 days per number of cells.
(iii) Nitric Oxide (NO) Production
NO mediated vascular relaxation was evaluated in an organ-chamber. Briefly, guinea pig thoracic aorta was harvested, the endothelium layer was removed by gentle rubbing and cut into 5-mm segments. Each segment was suspended between 2 tungsten stirrups for measurement of isometric tension. The vessel segments placed in an organ chamber with 10 ml Kreb's buffer solution at 37° C. with a mixture of 5% $CO_2$, 15% $O_2$ and a balance of $N_2$. Each HSVEC seeded vessel (2-3 cm in length) was tied to a 21 G needle, which was attached to plastic IV tubing and placed above the organ chamber with the fresh aortic segment. The segments were contracted with 80 mM KCl Kreb's buffer in a stepwise fashion to obtain a resting tension of 4 g. After resting for 90 minutes, the segments contracted in response to prostaglandin F2α up to a final concentration of 10-7 and until a stable contraction of approximately 50% of maximum KCl-induced contraction was achieved. Vasoactive agents and antagonists were then added using an infusion pump through the HSVEC seeded vessels to induce NO production. Doses of the vasoactive agents between $10^{-7}$-$10^{-3}$M were tested and dose-response curves were constructed.

Figure 14A:
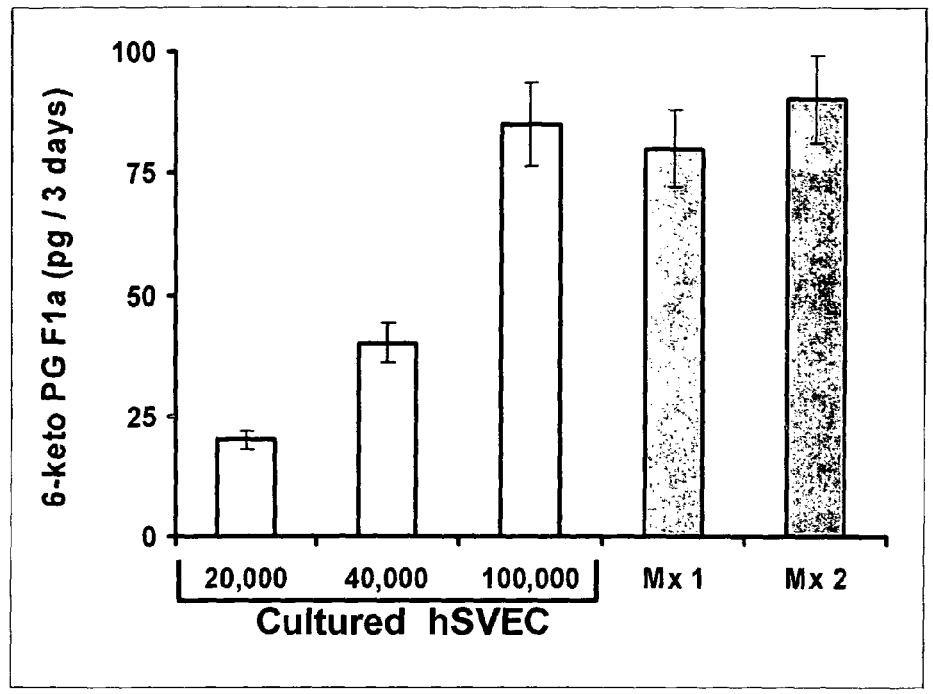
FIG. 14A is a bar graph showing the production of 6-ket-PGF1 from decellularized blood vessels seeded with human endothelial cells.

To examine if HSVEC seeded on the decellularized vessels are functional, prostaglandin and nitric oxide metabolism in the cells was evaluated. The synthesis of 6-keto prostaglandin F1α, a potent inhibitor of platelet aggregation and a vascular smooth muscle relaxant was examined, as well as the hydrolysis product of PGI2 (FIG. 14A).

Figure 14B:
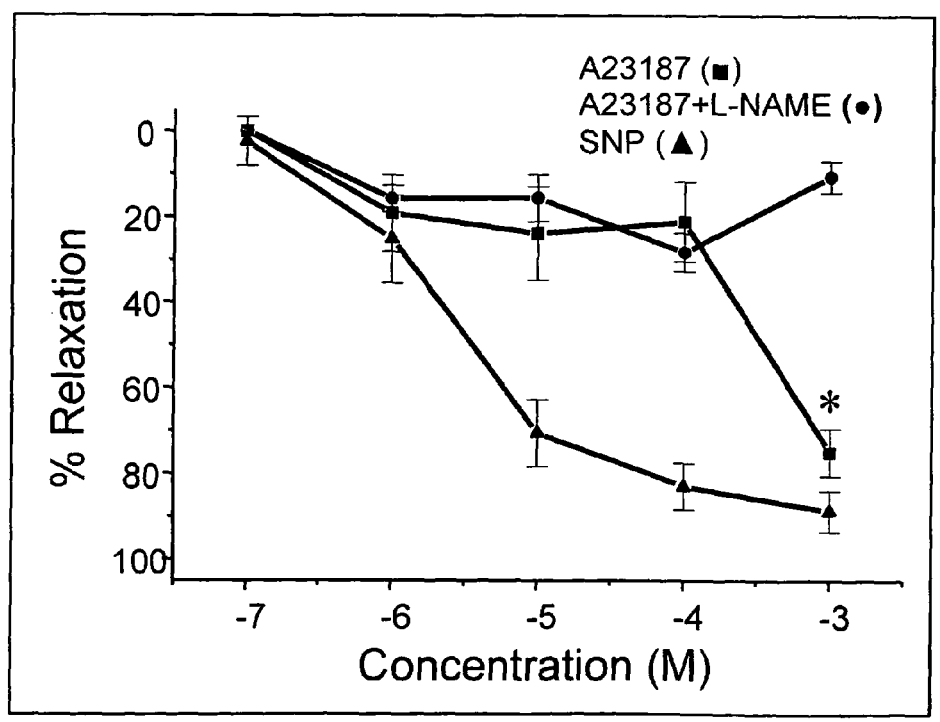
FIG. 14B is a graph showing the production of nitric oxide from decellularized blood vessels seeded with human endothelial cells.
Figure 15:
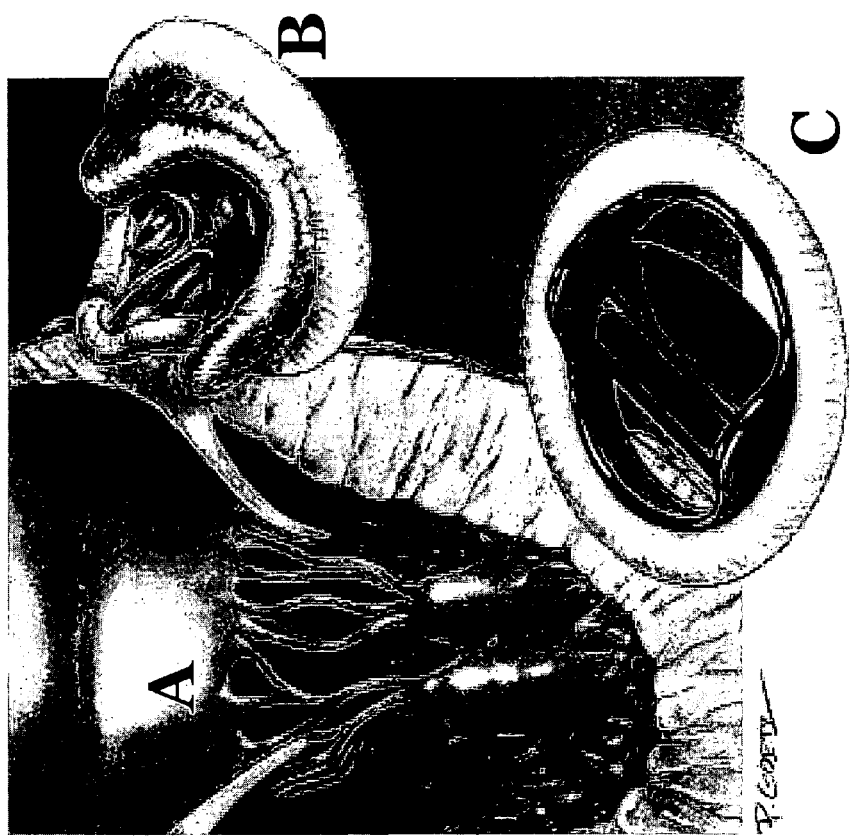
FIG. 15A is a schematic of a normal mitral valve (A), porcine replacement valve (B), and artificial replacement valve (C)
Figure 18:
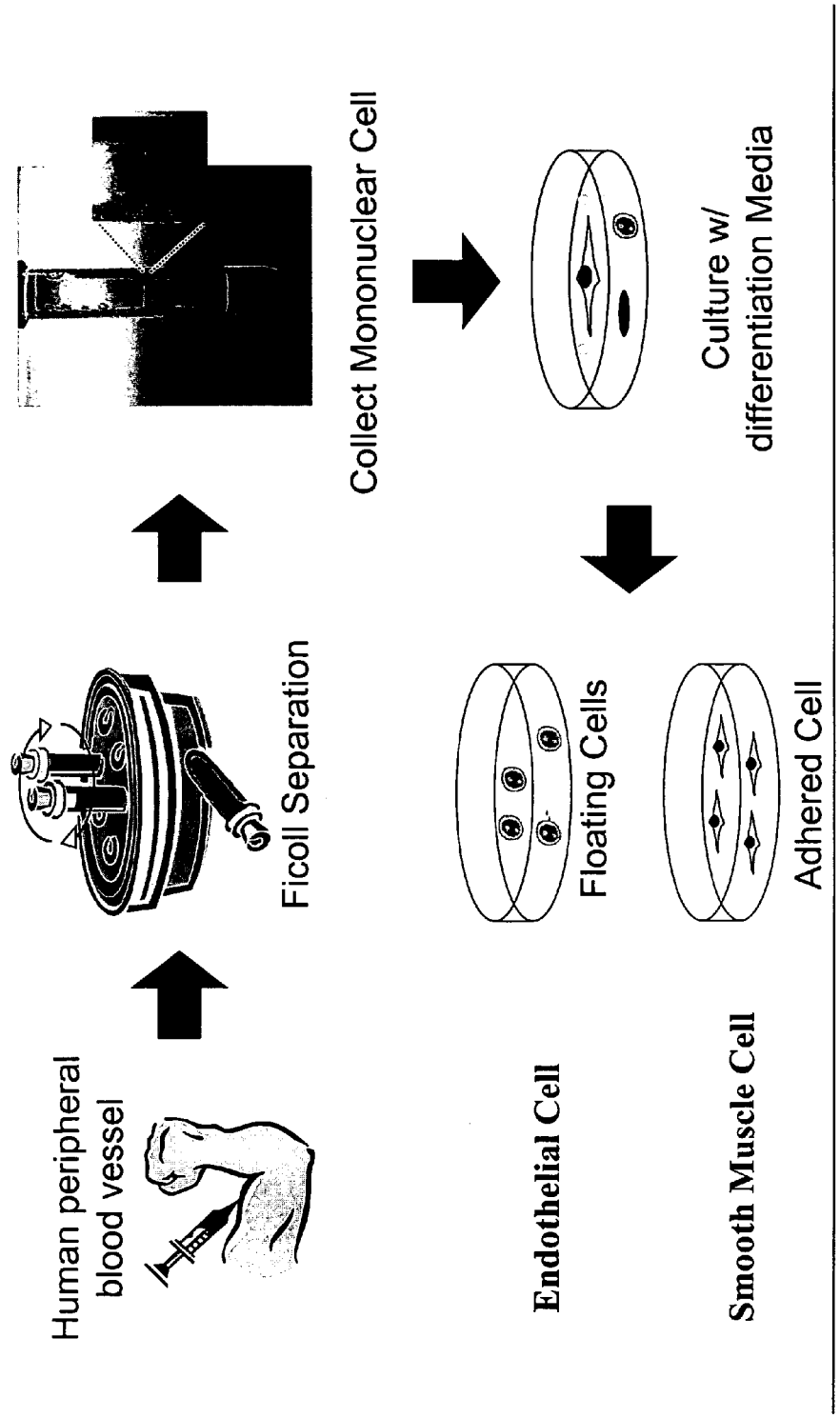
FIG. 18 is a schematic showing the isolation of cells form peripheral blood.
Figure 19:
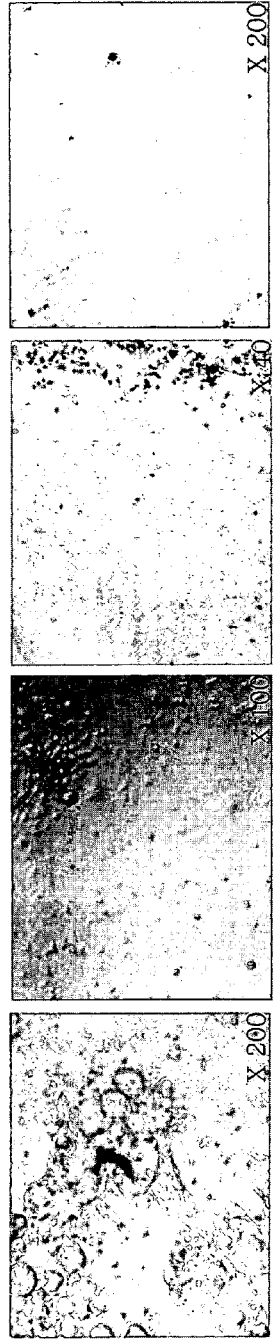
FIG. 19 are images of human endothelial and smooth muscle like cells differentiated from progenitor cells.
Figure 19:
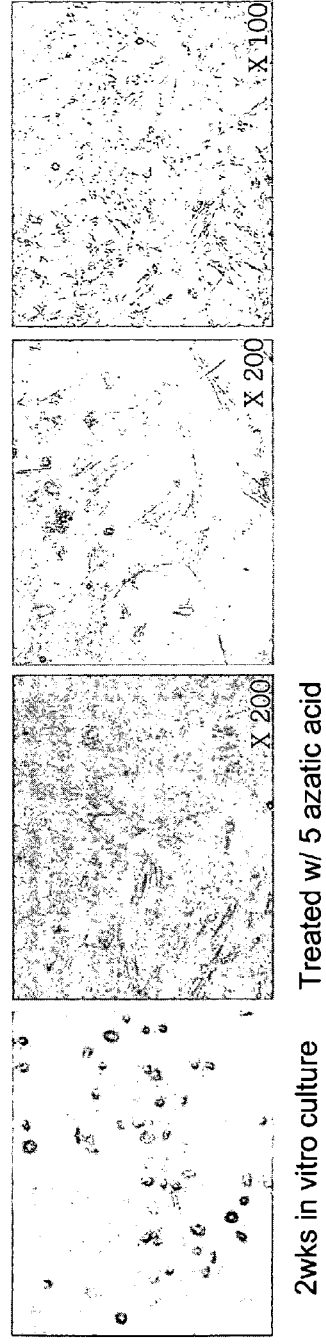
Figure 20:
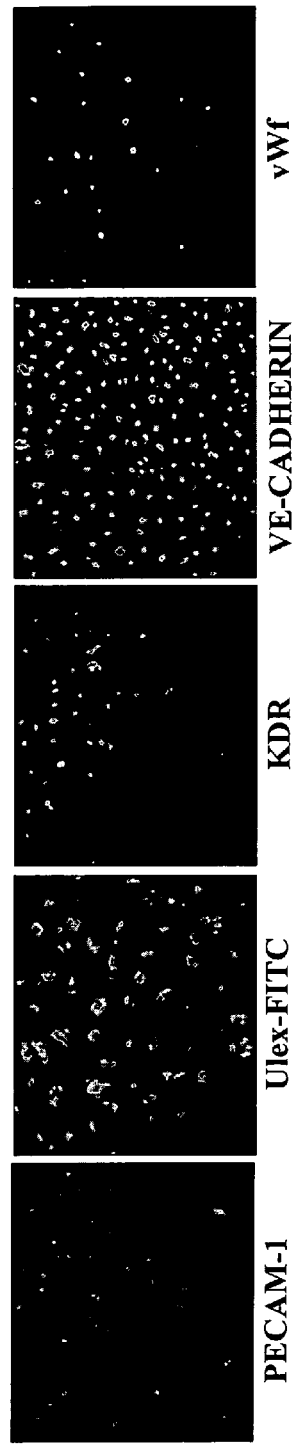
FIG. 20 are phase contrast images of human endothelial and smooth muscle like cells differentiated from progenitor cells.
Figure 20:
Figure 21:
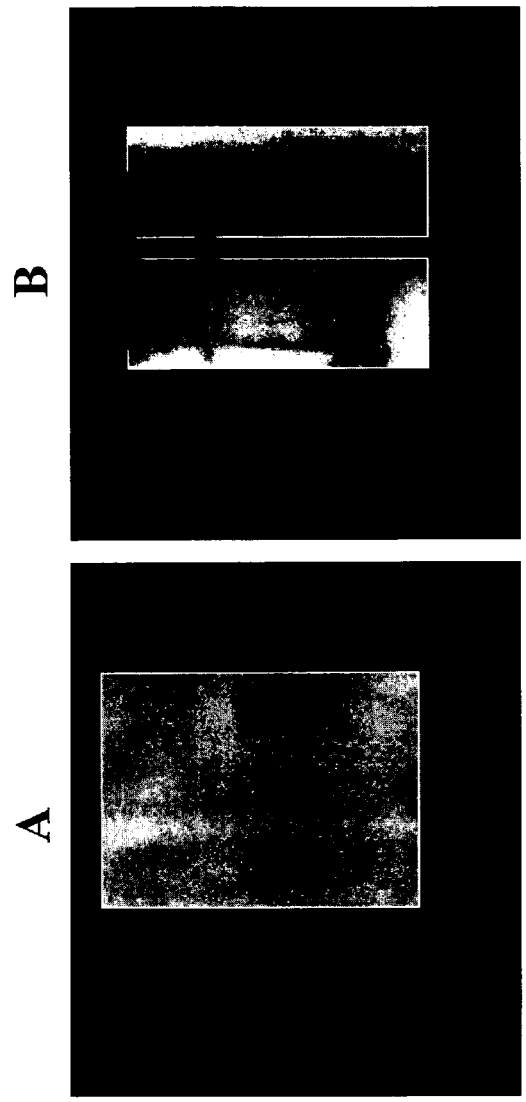
FIG. 21 are photographs of western blots differentiated endothelial cells (A) and smooth muscle like cells (B)
Figure 22:
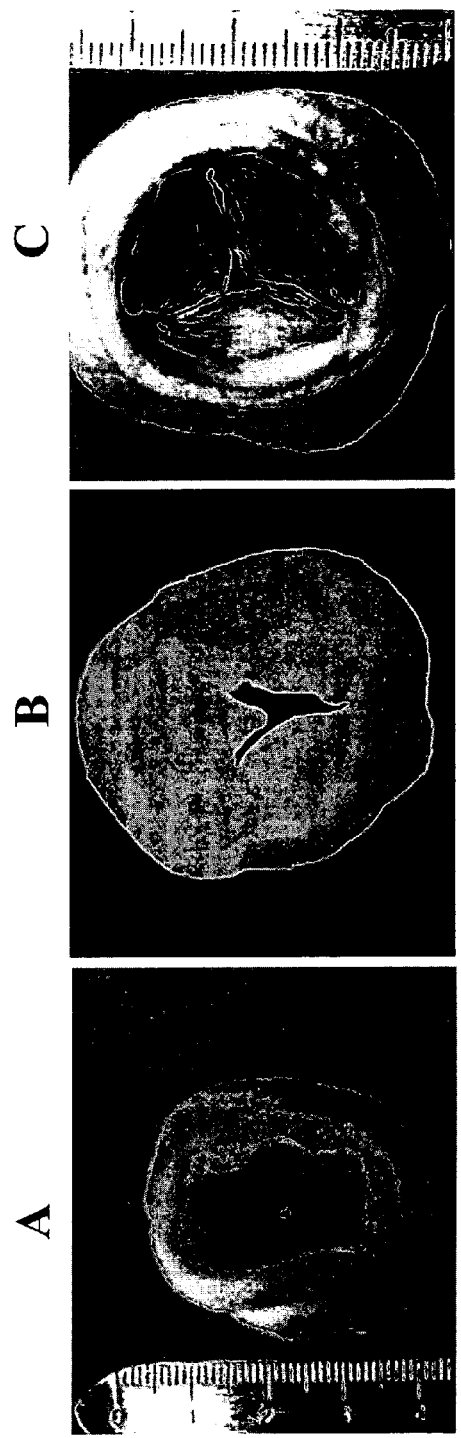
FIG. 22 are photographs of a porcine heart valve before decellularization (A), after decellularization (B) and after lyophillization (C)
Figure 23:
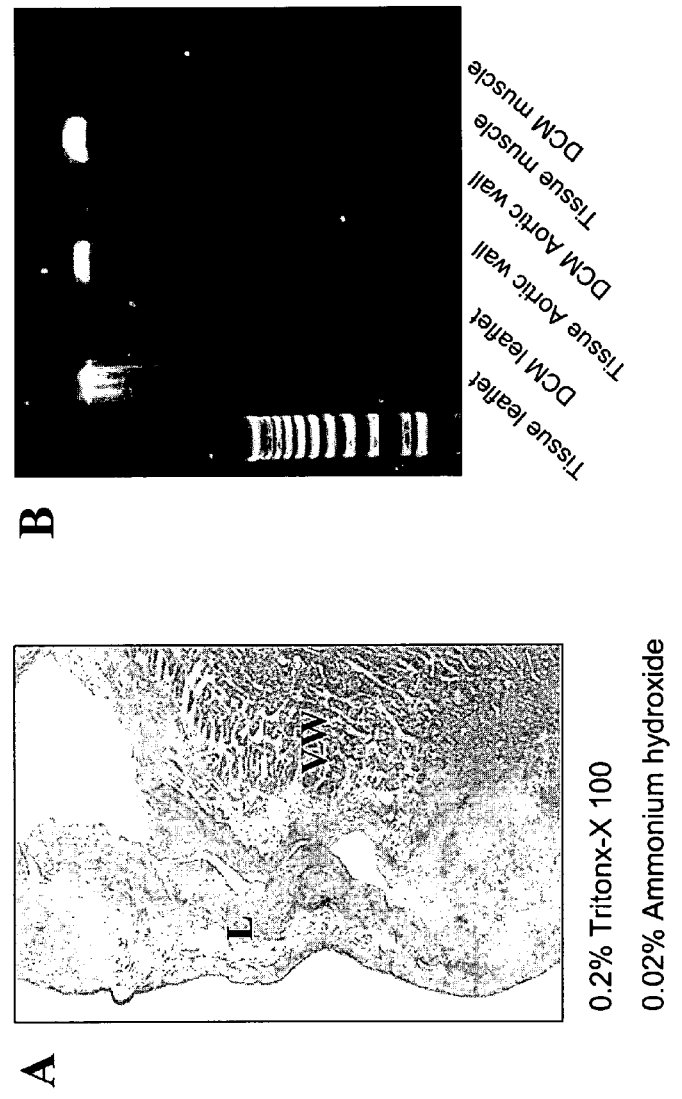
FIG. 23 shows an image of a porcine valve decellularized matrix (A) and an agarose gel showing a DNA assay of the decellularized matrix (B)
Figure 24:
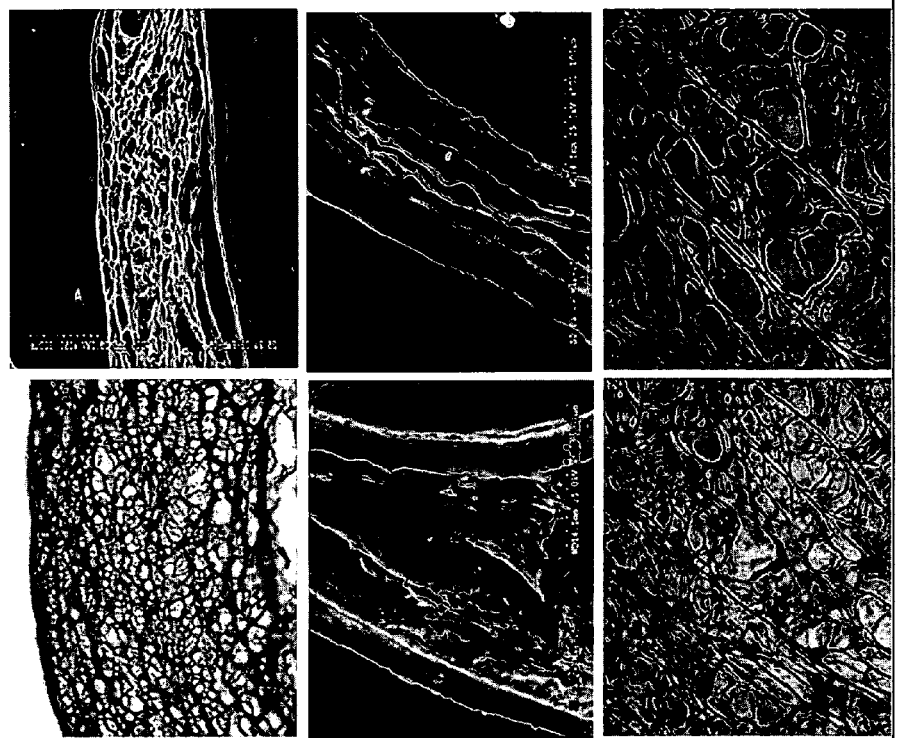
FIG. 24 are images of a porcine decellularized matrix.
Figure 25:
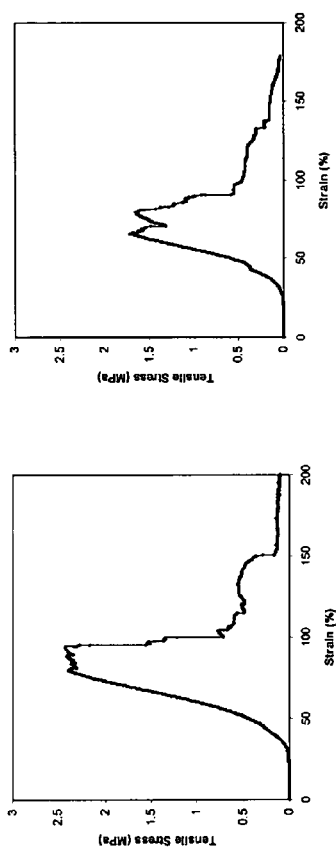
FIG. 25 are graphs showing the results of mechanical testing of the decellularized leaflet.

Decellularized vessel-seeded HSVEC secreted approximately 80 pg of 6-keto prostaglandin (PG) F1α in 3 days. This level was similar to the amount of 6-keto PG F1a secreted by a sub-confluent monolayer (100,000 cells) of HSVEC in a 75 mm2 tissue culture dish. The ability of HSVEC to produce NO was also examined using an organ-chamber methodology (FIG. 14B). Endothelium-denuded segments of guinea-pig aortas were contracted with Prostaglandin F2 alpha. The segments were exposed to increasing concentrations of the calcium ionophore A23187 that was perfused through HSVEC-seeded grafts in the same organ chamber. The guinea-pig aortic segments relaxed in a dose-dependent manner. This dose-dependent relaxation response to A23187 was significantly attenuated by adding $1\times10^{-3}$ M of the endothelial NO-synthase inhibitor L-NAME (75.0% versus 10.7%, $p<0.001$). When A23187 was perfused through grafts not seeded with HSVEC, the guinea-pig aortic segments remained fully contracted. Finally, exposing the aortic segments to increasing concentrations of sodium nitroprusside (SNP), an endothelial-independent NO donor, resulted in a dose-response relaxation, indicating normal smooth-muscle function in the guinea-pig aortic segments. These results indicate that HSVEC seeded on decellularized vessels are able to produce EC specific metabolites in response to physiologic stimulus.

These results show that small diameter vascular grafts can be created using matrices such as decellularized matrix or nanospin matrices seeded with endothelial cells and using the bioreactor chamber and methods of the invention. Small-caliber blood vessels for clinical use by coating decellularized arteries with endothelial cells from a human source. Human saphenous vein endothelial cells (HSVEC) were successfully isolated from discarded segments of saphenous vein and formed a monolayer on the decellularized vessels. These results suggest that human endothelial cells-seeded decellularized vessels can serve as a clinical alternative for small diameter blood vessels for surgical purposes.

The decellularized porcine arterial segments were the appropriate size-range for vascular surgery, without the need to tubularize sheet-like matrices. The decellularized vessel matrix is composed of layers of collagen surrounding a layer of elastin, as shown by Movat staining. The multiple collagen layers contributed to the mechanical strength of the decellularized vessels that resisted pressures of 1,900 mmHg without any noticeable leakage. The decellularization process did not alter the porosity of the vessel wall as demonstrated by SEM. The presence of an elastin layer on the lumen of the vessels enhanced the adherence and growth of endothelial cells.

The presence of a confluent endothelial cells monolayer on small-caliber prosthetic grafts is essential to provide protection from thrombus formation following implantation. To avoid the immune response to xenografts, largely due to high immunogenicity of the non-human endothelial cells, human endothelial cells were isolated from saphenous veins and used to seed the decellularized matrix. Saphenous vein-derived endothelial cells were isolated by enzymatic digestion and reached the critical amount of cells required for seeding a 5 cm long decellularized vessel (approximately $5 \times 10^6$ cells) after 10-14 days in-vitro. HSVEC maintained a typical endothelial cell monolayer for up to 12 passages and expressed endothelial cells markers such as CD31, vWF and KDR (VEGFR-2).

The bioreactor chamber of the invention was used to efficiently seed the cells onto the decellularized vessels. The cells adhered to the luminal side of the vessel and formed a continuous monolayer that was preserved after 7 days in vivo. These results indicate that the decellularization process resulted in a biocompatible matrix composed of collagen and elastin and that the native matrix can support HSVEC growth.

It was further demonstrated that the seeded HSVEC synthesized prostaglandin (PG) I2, as measured by levels of 6-keto PG F1a in the conditioned medium, and produced NO by an organ-chamber analysis. These potent vasodilators, specifically secreted by endothelial cells in response to biochemical and mechanical stimuli are essential to maintain long-term graft patency. The ability to synthesize vasoactive agents further indicates that HSVEC can serve as a functional layer to coat the decellularized vessel lumen. NO contributes to resting vascular tone, impairs platelet activation, and prevents leukocyte adhesion to the endothelium. These effects of NO on the vessel wall are important to protect the implanted graft against early thrombosis and later atherosclerosis. Thus, the methods of the invention are useful for the generation of functional blood vessels, particularly small-caliber blood vessels.

Example 26

Creation of Tissue Engineered Heart Valves

This example described the various techniques used to produce and precondition heart valves from circulating progenitor cells obtained from patients with vascular disease.

Circulating progenitor cells were isolated, grown and expanded from blood samples of patients with vascular disease. The cells were characterized with known cell specific markers. The expanded cells were induced into endothelial and smooth muscle cell lineages followed by cell characterization. The cells were seeded onto collagen-based porcine derived valve matrix. The valve matrices seeded with cells can be placed under dynamic flow conditions that mimic normal circulation. The valve constructs can be examined histologically, structurally and biomechanically over time.

Populations of circulating progenitor cells were successfully isolated, grown and expanded for the peripheral blood of patients with vascular disease. The progenitor cells were confirmed using multiple cell specific markers. The differentiated endothelial and muscle cells were characterized immunohistochemically using cell specific antibodies and with Western blot analyses. The cells seeded on valve matrices attached, proliferated and formed defined cell layers. The engineered valve tissue possessed similar biomechanical properties as normal valve tissues. The degree of coagulation was minimal on the cell covered valve surface, when compared to the controls without cells. The results of this study are shown in FIGS. 15 to 25.

This study shows that progenitor cells can be isolated and grown from the peripheral blood of patients with vascular disease. Endothelial and muscle cells differentiated from circulating progenitor cells are able to cover the valve surface and prevent coagulation. The valves were analyzed mechanically, biochemically, and morphologically. Plate deposition on the seeded matrices was identified with scanning electron microscopy after placing whole blood onto the matrix. The amount of platelets (white bead like figures in scanning electron microscopy) was observed under SEM. The use of this technology may improve the outcome of heart valve surgery by minimizing the occurrence of thrombosis formation.

The invention claimed is:
1. A method for producing a preconditioned heart valve, comprising:
   isolating progenitor cells comprising at least one of endothelial progenitor cells and smooth muscle progenitor cells;
   differentiating, ex vivo, the progenitor cells into endothelial cells or smooth muscle cells;
   seeding a matrix having a heart valve shape with the differentiated cells such that the cells attach to the matrix to form at least one cell layer;
   attaching the seeded matrix to an attachment element in a preconditioning chamber, wherein the attachment element has a channel that is fluidly coupled to a fluid flow system;
   preconditioning the seeded matrix prior to implantation with the flow system by moving a biological fluid through the seeded matrix, wherein a flow rate and a pulse rate of the biological fluid is controlled so that the seeded matrix is exposed to conditions that mimic flow of blood through a native heart valve, wherein the pulse rate induces a pressure in a range of about 60 mmHg to about 200 mmHg; and continuing exposure of the cells on the surface of the matrix to the flow rate and the pulse rate to allow the seeded cells to develop under fluid flow conditions;

wherein the matrix is an electrospun matrix comprising at least one natural component, at least one synthetic polymer component, and a therapeutic agent;

wherein the therapeutic agent is coupled to a quantum dot encapsulated in a polymer and the quantum dot is configured to release the coupled therapeutic agent when heated by radiation at a wavelength in the range of about 700 nm to about 1000 nm is applied.

2. The method of claim 1, wherein the quantum dot is configured to alter the ultrastructure of the at least one synthetic polymer component when heated by radiation at a wavelength in the range of about 700 nm to about 1000 nm.

* * * * *